US009827290B2

(12) United States Patent
Geng et al.

(10) Patent No.: US 9,827,290 B2
(45) Date of Patent: Nov. 28, 2017

(54) COMPOSITIONS AND METHODS RELATING TO INDUCTION OF INTESTINAL STEM CELL HOMEOGENESIS AND/OR REGENERATION

(71) Applicant: The Regents of the University of Michigan, Ann Arbor, MI (US)

(72) Inventors: Jian-Guo Geng, Saline, MI (US); Wei-Jie Zhou, Ann Arbor, MI (US); Li Ma, Saline, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/770,044

(22) PCT Filed: Feb. 25, 2014

(86) PCT No.: PCT/US2014/018318
§ 371 (c)(1),
(2) Date: Aug. 24, 2015

(87) PCT Pub. No.: WO2014/134038
PCT Pub. Date: Sep. 4, 2014

(65) Prior Publication Data
US 2016/0000865 A1 Jan. 7, 2016

Related U.S. Application Data

(60) Provisional application No. 61/770,812, filed on Feb. 28, 2013.

(51) Int. Cl.
| *A61K 38/17* | (2006.01) |
| *A61K 38/18* | (2006.01) |
| *A61P 1/04* | (2006.01) |
| *A61K 45/06* | (2006.01) |

(52) U.S. Cl.
CPC ............ *A61K 38/179* (2013.01); *A61K 38/18* (2013.01); *A61K 45/06* (2013.01)

(58) Field of Classification Search
None
See application file for complete search history.

(56) References Cited

U.S. PATENT DOCUMENTS

2010/0183749 A1 7/2010 Brey

OTHER PUBLICATIONS

Sludeja et al., Cell Stem Cell, 2015, vol. 17(6):663-674.*
Bach et al., carcinogenesis, 2000, vol. 21(3):469-476 (Abstract).*
Bhanja et al., PloS One, 2009, vol. 4(11):e8014, pp. 1-10.*
Zhao et al., PNAS, 2009, vol. 106(7):2331-2336.*
Albuquerque et al., "The 'just-right' signaling model: APC somatic mutations are selected based on a specific level of activation of the beta-catenin signaling cascade." 2002 Hum. Mel. Genet. 11, 1549-1560.
Altay et al., "Slit modulates cerebrovascular inflammation and mediates neuroprotection against global cerebral Ischemia." 2007 Exp. Neurol. 207, 186-194.
Andrews et al., "Robo1 regulates the development of major axon tracts and interneuron migration in the forebrain" (2006) Development 133, 2243-2252.
Barker et al., "Identification of stem cells in small intestine and colon by marker gene Lgr5." 2007 Nature 449, 1003-1007.
Beck and Stringer "The role of Cdx genes in the gut and in axial development." 2010 Biochem. Soc. Trans. 38, 353-357.
Bedell et al., "roundabout4 is essential for angiogenesis in vivo." 2005 Proc. Natl. Acad. Sci. USA 102, 6373-6378.
Bhanja et al. "Protective role of R-spondin1. An intestinal stem cell growth factor, against radiation-induced gastrointestinal syndrome in mice" Plos One, 2009, vol. 4, Issue 11, Article No. e8014, pp. 1-10.
Binnerts et al., "R-Spondin1 regulates Wnt signaling by inhibiting internalization of LRP6" 2007 Proc. Natl. Acad. Sci. USA 104, 14700-14705.
Borrell et al., "Slit/Robo Signaling Modulates the Proliferation of Central Nervous System Progenitors." 2012 Neuron 76, 338-352.
Burdelya L.G., et al., "An agonist of toll-like receptor 5 has radioprotective activity in mouse and primate models." (2008) Science 320, 226-230.
Carmon et al., "R-spondins function as ligands of the orphan receptors LGR4 and LGR5 to regulate Wnt/β-catenin signaling" 2011 Proc. Natl. Acad. Sci. USA. 108, 11452-11457.
Carmon et al., "LGR5 Interacts and Cointernalizes with Wnt Receptors to Modulate Wnt/β-Catenin Signaling." 2012 Mol. Cell. Biol. 32, 2054-2064.
Chen et al., "Cutting edge: bone morphogenetic protein antagonists Drm/Gremlin and Dan interact with Slits and act as negative regulators of monocyte chemotaxis." 2004 J. Immunol. 173, 5914-5917.
Clevers and Nusse, "Wnt/β-catenin signaling and disease." (2012) Cell 149, 1192-1205.
Clevers, H. "The Intestinal Crypt, A Prototype Stem Cell Compartment" 2013 Cell 154, 274-284.
Czajkowsky et al., "Fc-fusion proteins: new developments and future perspectives." 2012 EMBO Mol. Med. 4, 1015-1028.
De Lau et al., "Lgr5 homologues associate with Wnt receptors and mediate R-spondin signalling." (2011) Nature 476, 293-297.
Dickson and Gilestro "Regulation of commissural axon pathfinding by slit and its Robo receptors." 2006 Annu. Rev. Cell Dev. Biol. 22, 651-675.

(Continued)

*Primary Examiner* — Xiaozhen Xie
(74) *Attorney, Agent, or Firm* — Casimir Jones, SC

(57) ABSTRACT

The present invention relates to compositions and methods for inducing intestinal stem cell homeogenesis and/or regeneration within intestinal tissue expressing Robo1 through administration of a Rspo1 agent and a Slit2 agent. Administration of such agents results in, for example, binding of the Rspo1 agent and Slit2 agent with Robo1, resulting in, for example, binding of the CC3 motif of Robo1 with LRP6, resulting in phosphorylation of LRP6, and ultimately, induction of intestinal stem cell homeogenesis and/or regeneration. In certain embodiments, such administration of a Rspo1 agent and a Slit2 agent is used to protect and/or prevent intestinal tissue damage resulting from exposure to an intestinal tissue damaging event (e.g., radiation). The agents and related compositions additionally find use in diagnostic and research settings.

12 Claims, 32 Drawing Sheets

(56) References Cited

OTHER PUBLICATIONS

Dunaway et al., "Cooperative Signaling between Slit2 and Ephrin-A1 Regulates a Balance between Angiogenesis and Angiostasis." 2011 Mol. Cell. Biol. 31, 404-416.
Fish et al., 2011 "A Slit/miR-218/Robo regulatory loop is required during heart tube formation in zebrafish." Development 138, 1409-1419.
Glinka et al., "LGR4 and LGR5 are R-spondin receptors mediating Wnt/β-catenin and Wnt/PCP signalling." 2011 EMBO Rep. 12, 1055-1061.
Gong et al., "LGR6 Is a High Affinity Receptor of R-Spondins and Potentially Functions as a Tumor Suppressor." 2012 PLoS One 7, e37137.
Gracz et al., "CD24 and CD44 mark human intestinal epithelial cell populations with characteristics of active and faculatative stem cells" 2013 Stem Cells 31, 2024-2030.
Grieshammer et al., "SLIT2-Mediated ROBO2 Signaling Restricts Kidney Induction to a Single Site" 2004 Dev. Cell 6, 709-717.
Guan et al., Neuronal Repellent Slit2 Inhibits Dentritic Cell Migration and the Development of Immune Responses. 2003 J. Immunol. 171, 6519-6526.
Guijarro-Munoz et al., "The axonal repellent Slit2 inhibits pericyte migration: Potential implications in angiogenesis." 2012 Exp. Cell Res. 318, 371-378.
Guo et al., "Slit2 Overexpression Results in Increased Microvessel Density and Lesion Size in Mice With Induced Endometriosis." 2013 Reprod. Sci. 20, 285-298.
Liu et al., "Valproic Acid and Progestin Inhibit Lesion Growth and Reduce Hyperalgesia in Experimentally Induced Endometriosis in Rats" 2012 Reprod. Sci., 19(4): 360-373.
Haimovitz-Friedman et al., "Imaging Radiotherapy-Induced Apoptosis." 2012 Radiat. Res. 177, 467-482.
Han and Geng, "Over-expression of Slit2 induces vessel formation and changes blood vessel permeability in mouse brain." 2011 Acta Pharmacol. Sin. 32, 1327-1336.
Hao et al., "ZNRF3 promotes Wnt receptor turnover in an R-spondin-sensitive manner." 2012 Nature 485, 195-200.
Holland et al., "Wnt signaling in stem and cancer stem cells." 2013 Curr. Opin. Cell Biol. 25, 254-264.
Hua et al., "Crypt Base Columnar Stem Cells in Small Intestines of Mice Are Radioresistant" (2012) Gastroenterology 143, 1266-1276.
International Search Report and Written Opinion, International Patent Application No. PCT/US2014/018318, dated May 22, 2014.
Jones et al, "Robo4 stabilizes the vascular network by inhibiting pathologic angiogenesis and endothelial hyperpermeability." 2008 Nat. Med. 14, 448-453.
Jones et al., "Slit2—Robo4 signalling promotes vascular stability by blocking Arf6 activity." 2009 Nat. Cell Biol. 11, 1325-1331.
Jung et al., "Isolation and in vitro expansion of human colonic stem cells." 2011 Nat. Med. 17, 1225-1227.
Kanellis et al., "Modulation of Inflammation by Slit Protein in Vivo in Experimental Crescentic Glomerulonephritis." 2004 Am. J. Pathol. 165, 341-352.
Katoh et al., "CXCR2-expressing myeloid-derived suppressor cells are essential to promote colitis-associated tumorigenesis." 2013 Cancer Cell 24, 631-644.
Kazanskaya et al., "R-Spondin2 Is a Secreted Activator of Wnt/β-Catenin Signaling and Is Required for Xenopus Myogenesis." 2004 Dev. Cell 7, 525-534.
Khusial et al., "Src activates Abl to augment Robo1 expression in order to promote tumor cell migration." (2010) Oncotarget 1(3) 198-209.
Kim et al., "Mitogenic Influence of Human R-Spondin1 on the Intestinal Epithelium." 2005 Science 309, 1256-1259.
Kinzler and Vogelstein, "Lessons from hereditary colorectal cancer." 1996 Cell 87, 159-170.
Kontermann, "Strategies for extended serum half-life of protein therapeutics." 2011 Curr. Opin. Biotechnol. 22, 868-876.
Korinek V. et al., "Depletion of epithelial stem-cell compartments in the small intestine of mice lacking Tcf-4 . . . " (1998) Nat. Genet. 19, 379-383.
Kuhnert et al., "Essential requirement for Wnt signaling in proliferation of adult small intestine and colon revealed by adenoviral expression of Dickkopf-1." (2004) PNAS 101, 266-271.
Lepourcelet et al., "Small-molecule antagonists of the oncogenic Tcf/beta-catenin protein complex." 2004 Cancer cell 5, 91-102.
Long et al., "Conserved roles for Slit and Robo proteins in midline commissural axon guidance." 2004 Neuron 42, 213-223.
Macdonald et al., "Wnt/beta-catenin signaling: components, mechanisms, and diseases." 2009 Dev. Cell. 17, 9-26.
Macmullin and Jacobs, "Slit coordinates cardiac morphogenesis in *Drosophila*." 2006 Dev. Biol. 293, 154-164.
Ying et al., "The ground state of embryonic stem cell self-renewal." 2008 Nature 453, 519-523.
Ypsilanti et al., "Moving away from the midline: new developments for Slit and Robo." 2010 Development 137, 1939-1952.
Yuasa-Kawada et al., "Deubiquitinating enzyme USP33/VDU1 is required for Slit signaling in inhibiting breast cancer cell migration." 2009 Proc. Natl. Acad. Sci. USA 106, 14530-14535.
Zhang et al., "Repulsive axon guidance molecule Slit3 is a novel angiogenic factor." 2009 Blood 114, 4300-4309.
Zhao et al. "R-Spondin1 protects mice from chemotherapy or radiation-induced oral mucositis through the canonical Wnt/beta-catenin pathway."Proc Natl Acad Sci U S A. Feb. 17, 2009;106(7):2331-6.
Zhao et al., "R-Spondin1, a novel intestinotrophic mitogen, ameliorates experimental colitis in mice." 2007 Gastroenterology 132, 1331-1343.
Zhou et al. "Induction of intestinal stem cells by R-spondin 1 and Slit2 augments chemoradioprotection." Nature. 2013;501(7465):107-11.
Zhou et al. "Slit-Robo signaling induces malignant transformation through Hakai-mediated E-cadherin degradation during colorectal epithelial cell carcinogenesis." Cell Res. Apr. 2011;21(4):609-26.
Byun et al. "Slit2 Inactivates GSK3β to Signal Neurite Outgrowth Inhibition." PLoS One, 2012, 7, e51895.
Martin et al., "High-Dose 5-Fluorouracil with Delayed Uridine "Rescue" in Mice." (1982) Cancer Res. 42, 3964-3970.
Medioni et al., "Genetic control of cell morphogenesis during *Drosophila melanogaster* cardiac tube formation." 2008 J. Cell Biol. 182, 249-261.
Mertsch et al., "Slit2 involvement in glioma cell migration is mediated by Robot receptor." 2008 J. Neurooncol. 87, 1-7.
Metcalfe et al., "Lgr5+ Stem Cells Are Indispensable for Radiation-Induced Intestinal Regeneration." 2013 Cell Stem Cell vol. 14 Issue 2 149-159.
Mohrin et al., "Hematopoietic Stem Cell Quiescence Promotes Error-Prone DNA Repair and Mutagenesis." 2010 Cell Stem Cell, vol. 7, Issue 2, 174-185.
Morlot et al., "Structural insights into the Slit-Robo complex." 2007 Proc. Natl. Acad. Sci. USA 104, 14923-14928.
Nam et al., "Mouse Cristin/R-spondin Family Proteins Are Novel Ligands for the Frizzled 8 and LRP6 Receptors and Activate beta-Catenin-dependent Gene Expression" 2006 J. Biol. Chem. 281, 13247-13257.
Nelson and Nusse, "Convergence of Wnt, beta-catenin, and cadherin pathways." 2004 Science 303, 1483-1487.
Dotani et al., "Sustained in vitro intestinal epithelial culture within a Wnt-dependent stem cell niche." 2009 Nat. Med. 15, 701-706.
Phesse et al. "Responding to R-Spondin: Slit2 Potentiates Intestinal Regeneration" 2013 Cancer Stem Cell vol. 31(5) 512-514.
Pinto et al., "Canonical Wnt signals are essential for homeostasis of the intestinal epithelium." (2003) Genes. Dev. 17, 1709-1713.
Prasad et al., "Slit protein-mediated inhibition of CXCR4-induced chemotactic and chemoinvasive signaling pathways in breast cancer cells." 2004 J. Biol. Chem. 279, 9115-9124.
Prasad et al., "Pivotal Advance: Slit-2/Robo-1 modulates the CXCL12/CXCR4-induced chemotaxis of T cells." 2007 J. Leukoc. Biol. 82, 465-476.
Qian et al., "Slit and Robo control cardiac cell polarity and morphogenesis." 2005 Curr. Biol. 15, 2271-2278.

(56) References Cited

OTHER PUBLICATIONS

Rhee et al., "Activation of the repulsive receptor Roundabout inhibits N-cadherin-mediated cell adhesion."2002 Nat. Cell Biol. 4, 798-805.
Rhee et al., "Cables links Robo-bound Abl kinase to N-cadherin-bound bold beta-catenin to mediate Slit-induced nodulation of adhesion and transcription." 2007 Nat. Cell Biol. 9, 883-892.
Ring et al., "Selective glycogen synthase kinase 3 inhibitors potentiate insulin activation of glucose transport and utilization in vitro and in vivo." 2003 Diabetes 52, 588-595.
Rodrigues et al., "p53 mutations in colorectal cancer." 1990 Proc. Natl. Acad. Sci. USA 87, 7555-7559.
Roque et al., "Lack of a p21waf1/cip-Dependent G1/S Checkpoint in Neural Stem and Progenitor Cells After DNA Damage In Vivo." 2012 Stem Cells 30, 537-547.
Ruffner et al., "R-Spondin Potentiates Wnt/β-Catenin Signaling through Orphan Receptors LGR4 and LGR5." 2012 PLoS One 7, e40976.
Santiago-Martinez et al., "Lateral positioning at the dorsal midline: Slit and Roundabout receptors guide *Drosophila* heart cell migration." 2006 Proc. Natl. Acad. Sci. USA 103, 12441-12446.
Santiago-Martinez et al., "Repulsion by Slit and Roundabout prevents Shotgun/E-cadherin-mediated cell adhesion during *Drosophila* heart tube lumen formation." 2008 J. Cell Biol. 182, 241-248.
Sato et al., "Single Lgr5 stem cells build crypt-villus structures in vitro without a mesenchymal niche." 2009 Nature 459, 262-265.
Schuijers and Clevers, "Adult mammalian stem cells: the role of Wnt, Lgr5 and R-spondins." 2012 EMBO J. 31, 2685-2696.
Seshagiri et al., "Recurrent R-spondin fusions in colon cancer" (2012) Nature 488, 660-664.
Seth et al., "Magic roundabout, a tumor endothelial marker: expression and signaling." 2005 Biochem. Biophys. Res. Commun. 332, 533-541.
Snippert et al., "Intestinal crypt homeostasis results from neutral competition between symmetrically dividing Lgr5 stem cells." 2010 Cell 143, 134-44.
Solanas and Batlle "Control of cell adhesion and compartmentalization in the intestinal epithelium." (2011) Exp. Cell Research vol. 317(19):2695-2701.
Sotiropoulou et al., "Bcl-2 and accelerated DNA repair mediates resistance of hair follicle bulge stem cells to DNA-damage-induced cell death." 2010 Nature Cell Biol. 12, 572-582.
Spence et al., "Directed differentiation of human pluripotent stem cells into intestinal tissue in vitro." 2011 Nature 470, 105-109.
Stella et al., "The Slit/Robo System Suppresses Hepatocyte Growth Factor-dependent Invasion and Morphogenesis." 2009 Mol. Biol. Cell 20, 642-657.
Suchting et al., "Soluble Robo4 receptor inhibits in vivo angiogenesis and endothelial cell migration." 2004 FASEB J. 19, 121-123.
Takashima et al. "The Wnt agonist R-spondin1 regulates systemic graft-versus-host disease by protecting intestinal stem cells." The Journal of Experimental Medicine, 2011, vol. 208 No. 2 285-294.
Takeda et al., "Interconversion Between Intestinal Stem Cell Populations in Distinct Niches" 2011 Science 334, 1420-1424.
Tamai et al., "A mechanism for Wnt coreceptor activation." (2004) Mol. Cell 13 149-156.
Tian et al., "A reserve stem cell population in small intestine renders Lgr5-positive cells dispensable." 2011 Nature 478, 255-259.
Urbich et al., "HDAC5 is a repressor of angiogenesis and determines the angiogenic gene expression pattern of endothelial cells." 2009 Blood 113, 5669-5679.
Vogelstein et al., "Cancer genome landscapes." 2013 Science 339, 1546-1558.
Wang et al. "Induction of tumor angiogenesis by Slit-Robo signaling and inhibition of cancer growth by blocking Robo activity." Cancer Cell. Jul. 2003;4(1):19-29.
Wang et al., "P-selectin primes leukocyte integrin activation during inflammation." 2007 Nat. Immunol. 8, 882-892.
Wang et al., "Targeting Slit—Roundabout signaling inhibits tumor angiogenesis in chemical-induced squamous cell carcinogenesis." 2008 Cancer Sci. 99, 510-517.
Wang et al., "Isolation and characterization of intestinal stem cells based on surface marker combinations and colony-formation assay." 2013 Gastroenterology 145, 383-395.
Wang et al. "Induction of tumor angiogenesis by Slit-Robo signaling and inhibition of cancer growth by blocking Robo activity." (2003) Cancer Cell 4, 19-29.
Wei et al., "R-spondin1 is a high affinity ligand for LRP6 and induces LRP6 phosphorylation and beta-catenin signaling." 2007 J. Biol. Chem. 282, 15903-15911.
Wong et al., "Signal Transduction in Neuronal Migration: Roles of GTPase Activating Proteins and the Small GTPase Cdc42 in the Slit-Robo Pathway." (2001) Cell 107, 209-221.
Wu et al., "The neuronal repellent Slit inhibits leukocyte chemotaxis induced by chemotactic factors." 2001 Nature 410(6831) 948-952.
Wu et al., "RSPO2-LGR5 signaling has tumour-suppressive activity in colorectal cancer." 2014 Nat. Commun. 5, 3149.
Yan et al., "The intestinal stem cell markers Bmi1 and Lgr5 identify two functionally distinct populations." 2012 Proc. Natl. Acad. Sci. USA 109, 466-471.
Yang et al., "Slit-Robo signaling mediates lymphangiogenesis and promotes tumor lymphatic metastasis. Biochem. Biophys." 2010 Biochem. Biophys. Res. Commun. 396, 571-577.
Ye et al., Slit2 Regulates Attractive Eosinophil and Repulsive Neutrophil Chemotaxis through Differential srGAP1 Expression during Lung Inflammation. 2010 J. Immun. 185(10) 6294-6305.

* cited by examiner

| | Pro-A Beads | | | 5%input | | |
|---|---|---|---|---|---|---|
| hIgG: | + | - | - | + | - | - |
| Robo1-Fc: | - | + | + | - | + | + |
| Slit2: | + | + | + | + | + | + |
| Rspo1: | - | - | + | - | - | + |
| Slit2 | | | | | | |

B

| | Pro-A Beads | | | 5%input | | |
|---|---|---|---|---|---|---|
| hIgG: | + | - | - | + | - | - |
| Robo1-Fc: | - | + | + | - | + | + |
| Slit2: | - | - | + | - | - | + |
| Rspo1: | + | + | + | + | + | + |
| Rspo1 | | | | | | |

```
                              SEQUENCE LISTING

<160> NUMBER OF SEQ ID NOS: 40

<210> SEQ ID NO 1
<211> LENGTH: 38
<212> TYPE: DNA
<213> ORGANISM: Artificial Sequence
<220> FEATURE:
<223> OTHER INFORMATION: Synthetic

<400> SEQUENCE: 1
aaaggatcca atgggggccg tcctgaggag cctcctgg                            38

<210> SEQ ID NO 2
<211> LENGTH: 45
<212> TYPE: DNA
<213> ORGANISM: Artificial Sequence
<220> FEATURE:
<223> OTHER INFORMATION: Synthetic

<400> SEQUENCE: 2
aaagtcgact caggaggagt ctgtacaggg agagggtggc ggtgg                    45

<210> SEQ ID NO 3
<211> LENGTH: 37
<212> TYPE: DNA
<213> ORGANISM: Artificial Sequence
<220> FEATURE:
<223> OTHER INFORMATION: Synthetic

<400> SEQUENCE: 3
aaggatccat ggacacctcc cggctcggtg tgctcct                             37

<210> SEQ ID NO 4
<211> LENGTH: 43
<212> TYPE: DNA
<213> ORGANISM: Artificial Sequence
<220> FEATURE:
<223> OTHER INFORMATION: Synthetic

<400> SEQUENCE: 4
ggctcgagga gacatgggac aaatgccaca gaggaaagat ggc                      43

<210> SEQ ID NO 5
<211> LENGTH: 39
<212> TYPE: DNA
<213> ORGANISM: Artificial Sequence
<220> FEATURE:
<223> OTHER INFORMATION: Synthetic

<400> SEQUENCE: 5
aaaggatcca tgaaatggaa acatgttcct tttttggtc                           39

<210> SEQ ID NO 6
<211> LENGTH: 33
<212> TYPE: DNA
<213> ORGANISM: Artificial Sequence
<220> FEATURE:
<223> OTHER INFORMATION: Synthetic

<400> SEQUENCE: 6
aaactcgagt catgcattgt ggctcacagc ctc                                 33
```

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
aaaggatcct cgctggaagt agccatactt cgg                33

<210> SEQ ID NO 8
<211> LENGTH: 36
<212> TYPE: DNA
<213> ORGANISM: Artificial Sequence
<220> FEATURE:
<223> OTHER INFORMATION: Synthetic

<400> SEQUENCE: 8
aaactcgagt caagtcagct cggctacttc actctc             36

<210> SEQ ID NO 9
<211> LENGTH: 41
<212> TYPE: DNA
<213> ORGANISM: Artificial Sequence
<220> FEATURE:
<223> OTHER INFORMATION: Synthetic

<400> SEQUENCE: 9
aaaggatccg tcttagagag accatcattt gtgaagagac c        41

<210> SEQ ID NO 10
<211> LENGTH: 39
<212> TYPE: DNA
<213> ORGANISM: Artificial Sequence
<220> FEATURE:
<223> OTHER INFORMATION: Synthetic

<400> SEQUENCE: 10
aaactcgagt caaacagtca gagtagcaga tgcttcagc           39

<210> SEQ ID NO 11
<211> LENGTH: 38
<212> TYPE: DNA
<213> ORGANISM: Artificial Sequence
<220> FEATURE:
<223> OTHER INFORMATION: Synthetic

<400> SEQUENCE: 11
aaaggatccc aagaacctcc acatttttgt gtgaaacc            38

<210> SEQ ID NO 12
<211> LENGTH: 39
<212> TYPE: DNA
<213> ORGANISM: Artificial Sequence
<220> FEATURE:
<223> OTHER INFORMATION: Synthetic

<400> SEQUENCE: 12
aaactcgagt catccagcaa catttaaagt ctggcagat           39

<210> SEQ ID NO 13
<211> LENGTH: 41
<212> TYPE: DNA
<213> ORGANISM: Artificial Sequence
<220> FEATURE:

<223> OTHER INFORMATION: Synthetic

<400> SEQUENCE: 13
aaaggatcca gcatcatcac aaaggcatat ttggaagtta c                41

<210> SEQ ID NO 14
<211> LENGTH: 42
<212> TYPE: DNA
<213> ORGANISM: Artificial Sequence
<220> FEATURE:
<223> OTHER INFORMATION: Synthetic

<400> SEQUENCE: 14
aaactcgagt cactgaactg gaactccaaa ttcttgaact tc               42

<210> SEQ ID NO 15
<211> LENGTH: 40
<212> TYPE: DNA
<213> ORGANISM: Artificial Sequence
<220> FEATURE:
<223> OTHER INFORMATION: Synthetic

<400> SEQUENCE: 15
aaaggatcca tgcgccggga taaagaacgc caggccaaac                  40

<210> SEQ ID NO 16
<211> LENGTH: 39
<212> TYPE: DNA
<213> ORGANISM: Artificial Sequence
<220> FEATURE:
<223> OTHER INFORMATION: Synthetic

<400> SEQUENCE: 16
aaactcgagg tcatcacctc caccatacat gtcagcaag                   39

<210> SEQ ID NO 17
<211> LENGTH: 38
<212> TYPE: DNA
<213> ORGANISM: Artificial Sequence
<220> FEATURE:
<223> OTHER INFORMATION: Synthetic

<400> SEQUENCE: 17
attggatccg gatcctacaa cagctcagac cggggcag                    38

<210> SEQ ID NO 18
<211> LENGTH: 38
<212> TYPE: DNA
<213> ORGANISM: Artificial Sequence
<220> FEATURE:
<223> OTHER INFORMATION: Synthetic

<400> SEQUENCE: 18
attctcgagc tagccagcag catcctgcat ttgccgtc                    38

<210> SEQ ID NO 19
<211> LENGTH: 31
<212> TYPE: DNA
<213> ORGANISM: Artificial Sequence
<220> FEATURE:
<223> OTHER INFORMATION: Synthetic

<400> SEQUENCE: 19
attggatccc gtcgacattt tcatgcgtct c                           31

<210> SEQ ID NO 20
<211> LENGTH: 45
<212> TYPE: DNA
<213> ORGANISM: Artificial Sequence
<220> FEATURE:
<223> OTHER INFORMATION: Synthetic

<400> SEQUENCE: 20
ccgctcgagt cagctttcag tttcctctaa ttcttcatta ttatc        45

<210> SEQ ID NO 21
<211> LENGTH: 35
<212> TYPE: DNA
<213> ORGANISM: Artificial Sequence
<220> FEATURE:
<223> OTHER INFORMATION: Synthetic

<400> SEQUENCE: 21
aaaggatcca tgcggcttgg gctgtgtgtg gtggc        35

<210> SEQ ID NO 22
<211> LENGTH: 37
<212> TYPE: DNA
<213> ORGANISM: Artificial Sequence
<220> FEATURE:
<223> OTHER INFORMATION: Synthetic

<400> SEQUENCE: 22
aaactcgagc atggtgccat tggcagctga ggagccc        37

<210> SEQ ID NO 23
<211> LENGTH: 42
<212> TYPE: DNA
<213> ORGANISM: Artificial Sequence
<220> FEATURE:
<223> OTHER INFORMATION: Synthetic

<400> SEQUENCE: 23
cccggatcca tggagtgcag tagtcctgcg caatgtgaaa tg        42

<210> SEQ ID NO 24
<211> LENGTH: 36
<212> TYPE: DNA
<213> ORGANISM: Artificial Sequence
<220> FEATURE:
<223> OTHER INFORMATION: Synthetic

<400> SEQUENCE: 24
aaactcgagg gcaggccctg cagatgtgag tggccc        36

<210> SEQ ID NO 25
<211> LENGTH: 40
<212> TYPE: DNA
<213> ORGANISM: Artificial Sequence
<220> FEATURE:
<223> OTHER INFORMATION: Synthetic

<400> SEQUENCE: 25
aaaggatcct actttatctg ccagaggatg ttgtgtccac        40

<210> SEQ ID NO 26
<211> LENGTH: 41
<212> TYPE: DNA
<213> ORGANISM: Artificial Sequence
<220> FEATURE:
<223> OTHER INFORMATION: Synthetic

<400> SEQUENCE: 26
aaactcgagt caagacattc ctggaagaga tcctgacaaa g                     41

<210> SEQ ID NO 27
<211> LENGTH: 42
<212> TYPE: DNA
<213> ORGANISM: Artificial Sequence
<220> FEATURE:
<223> OTHER INFORMATION: Synthetic

<400> SEQUENCE: 27
aaaggatcct atgaccgagc ccatgttaca ggagcatcat ca                    42

<210> SEQ ID NO 28
<211> LENGTH: 32
<212> TYPE: DNA
<213> ORGANISM: Artificial Sequence
<220> FEATURE:
<223> OTHER INFORMATION: Synthetic

<400> SEQUENCE: 28
aaactcgagt cagctgcagg gtgtggtggg gg                               32

<210> SEQ ID NO 29
<211> LENGTH: 45
<212> TYPE: DNA
<213> ORGANISM: Artificial Sequence
<220> FEATURE:
<223> OTHER INFORMATION: Synthetic

<400> SEQUENCE: 29
aaaggatcca cagatgtttg tgacagtgac tatgctccta gtcgg                 45

<210> SEQ ID NO 30
<211> LENGTH: 40
<212> TYPE: DNA
<213> ORGANISM: Artificial Sequence
<220> FEATURE:
<223> OTHER INFORMATION: Synthetic

<400> SEQUENCE: 30
aaactcgagt caggaggagt ctgtacaggg agagggtggc                       40

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
ttgcggccgc atgcggcttg ggctgtg                                     27

<210> SEQ ID NO 32
<211> LENGTH: 34
<212> TYPE: DNA
<213> ORGANISM: Artificial Sequence
<220> FEATURE:
<223> OTHER INFORMATION: Synthetic

<400> SEQUENCE: 32
gggaattcgg caggccctgc agatgtgagt ggcc                             34

<210> SEQ ID NO 33
<211> LENGTH: 25

```
<212> TYPE: DNA
<213> ORGANISM: Artificial Sequence
<220> FEATURE:
<223> OTHER INFORMATION: Synthetic

<400> SEQUENCE: 33
tagcggccgc atggagcgct gcccc                                        25

<210> SEQ ID NO 34
<211> LENGTH: 36
<212> TYPE: DNA
<213> ORGANISM: Artificial Sequence
<220> FEATURE:
<223> OTHER INFORMATION: Synthetic

<400> SEQUENCE: 34
gggaattcgc acgagcactt gcactcggaa tgatgg                            36

<210> SEQ ID NO 35
<211> LENGTH: 34
<212> TYPE: DNA
<213> ORGANISM: Artificial Sequence
<220> FEATURE:
<223> OTHER INFORMATION: Synthetic

<400> SEQUENCE: 35
aaccgtgcgg ccgctgttgt gacaaaactc acac                              34

<210> SEQ ID NO 36
<211> LENGTH: 37
<212> TYPE: DNA
<213> ORGANISM: Artificial Sequence
<220> FEATURE:
<223> OTHER INFORMATION: Synthetic

<400> SEQUENCE: 36
cgcggagatc ttcatttacc cggagacagg gagaggc                           37

<210> SEQ ID NO 37
<211> LENGTH: 33
<212> TYPE: DNA
<213> ORGANISM: Artificial Sequence
<220> FEATURE:
<223> OTHER INFORMATION: Synthetic

<400> SEQUENCE: 37
ggcggcctct agaatgaaat ggaaacatgt tcc                               33

<210> SEQ ID NO 38
<211> LENGTH: 34
<212> TYPE: DNA
<213> ORGANISM: Artificial Sequence
<220> FEATURE:
<223> OTHER INFORMATION: Synthetic

<400> SEQUENCE: 38
ctataagcgg ccgccaatgt aagcactcca tgtt                              34

<210> SEQ ID NO 39
<211> LENGTH: 35
<212> TYPE: DNA
<213> ORGANISM: Artificial Sequence
<220> FEATURE:
<223> OTHER INFORMATION: Synthetic

<400> SEQUENCE: 39
```

```
aagaattcat gcgacatttt catgcgtctc agtgc                          35
```

<210> SEQ ID NO 40
<211> LENGTH: 35
<212> TYPE: DNA
<213> ORGANISM: Artificial Sequence
<220> FEATURE:
<223> OTHER INFORMATION: Synthetic

<400> SEQUENCE: 40

```
aactcgagtc agctttcagt ttcctctaat tcttc                          35
```

COMPOSITIONS AND METHODS RELATING TO INDUCTION OF INTESTINAL STEM CELL HOMEOGENESIS AND/OR REGENERATION

CROSS-REFERENCE TO RELATED APPLICATIONS

The present application is a 371 U.S. National Phase Entry of International Application No. PCT/US2014/018318, filed Feb. 25, 2014, which claims priority to U.S. Provisional Patent Application No. 61/770,812, filed Feb. 28, 2013, the contents of which are incorporated by reference in their entireties.

STATEMENT REGARDING FEDERALLY SPONSORED RESEARCH OR DEVELOPMENT

This invention was made with government support under CA126897 awarded by the National Institutes of Health. The government has certain rights in the invention.

FIELD OF THE INVENTION

The present invention relates to compositions and methods for inducing intestinal stem cell homeogenesis and/or regeneration within intestinal tissue expressing Robo1 through administration of a Rspo1 agent and a Slit2 agent. Administration of such agents results in, for example, binding of the Rspo1 agent and Slit2 agent with Robo1, resulting in, for example, binding of the CC3 motif of Robo1 with LRP6, resulting in phosphorylation of LRP6, and ultimately, induction of intestinal stem cell homeogenesis and/or regeneration. In certain embodiments, such administration of a Rspo1 agent and a Slit2 agent is used to protect and/or prevent intestinal tissue damage resulting from exposure to an intestinal tissue damaging event (e.g., radiation). The agents and related compositions additionally find use in diagnostic and research settings.

BACKGROUND OF THE INVENTION

The intestine is particularly susceptible to chemoradiation due to a continuous requirement for tissue maintenance by actively cycling intestinal stem cells (ISCs). ISC death is a major side effect of chemoradiotherapy disrupting intestinal homeostasis and causing a loss of intestinal tissue. A major clinical challenge concerns whether a way to drastically reduce this devastating and sometimes lethal intestinal injury caused by intensive chemoradiotherapy during treatment of late-staged cancer with systemic metastasis can be determined. Identification of novel therapeutics that enable ISC survival and function during chemoradiotherapy could greatly increase the range of treatment options, while decreasing catastrophic tissue and organ damage that leads to ultimate death of cancer patients.

SUMMARY

How to reduce lethal tissue damage caused by intensive chemoradiotherapy for treating metastatic cancers remains an enigma. Experiments conducted during the course of developing embodiments for the present invention tested whether induction of tissue-specific stem cells mitigates chemoradiation-induced tissue injury and prolongs overall survival. It was found that intestinal stem cells (ISCs) expressed a transmembrane receptor Roundabout 1 (Robo1). In addition, it was found that R-spondin 1 (Rspo1; a Wnt agonist) and Slit2 (a guidance cue) bound to the extracellular domains of Robo1 at distinctive sites, whereas the cytoplasmic CC3 motif of Robo1 bound to LRP6 and promoted LRP6 phosphorylation and association with LGR5, leading to synergistic activation of canonical Wnt signaling and cooperative induction of ISCs for intestinal homeostasis and regeneration. Indeed, such experiments resulted in the discovery that ISCs and proliferating TA cells residing at the crypt of small intestine express Slit2 and Robo1. Engagement of Robo1 by Slit2 was shown to induce LRP6 phosphorylation and association with LGR5, β-catenin translocation, TCF/LEF promoter activation and canonical Wnt targeting gene expression (FIG. 24). Even a partial genetic deletion of Robo1/2 was shown to be sufficient to reduce ISCs, TA cells and enterocytes, leading to villus hypotrophy, which were further verified by treating Wt mice with R5 to transiently inhibit Slit2 binding to Robo1. In contrast, Slit2 transgene was shown to augment the numbers of ISCs, TA cells and enterocytes, leading to villus hypertrophy and enhanced resistance to chemotherapy (FIG. 24). Mechanistically, Robo1/2 partial deficiency, R5 treatment or ectopic expression of the cytoplasmic CC3 motif of Robo1 was shown to inactivate β-catenin for suppressing the expression of canonical Wnt targeting genes, whereas Slit2 transgene was shown to be capable of activating β-catenin for inducing the expression of canonical Wnt targeting genes. The successful "rescue" of the Robo1$^{-/+}$/2$^{-/+}$ intestinal organoids by adenoviral β-catenin demonstrates the importance of Slit-Robo signaling, at the upstream of β-catenin activation, in intestinal homeostasis and regeneration.

Moreover, it was shown that upon lethal dosages of chemoradiation, administering a short pulse of Rspo1 plus Slit2 reduced ISC loss, mitigated intestinal impairment and protected animals from death, without concomitantly decreasing the sensitivity of intestinal cancer to chemotherapy. As such, by optimal induction of ISCs, Rspo1 and Slit2 serve as therapeutic adjuvants to increase host tolerance to chemoradiotherapy.

Additionally, experiments conducted during the course of developing embodiments for the present invention demonstrated that (1) Robo1 acts as a cognate receptor for both Rspo1 and Slit2 (FIG. 24A; see FIG. 29); (2) Rspo1 and Slit2 binding to Robo1 induces formation of Robo1-Lrp6-Lgr5 complex for activation of Wnt/β-catenin signaling (FIG. 24A; see FIG. 30); (3) Wnt/β-catenin activation elicited by Rspo1 and Slit2 transcriptionally represses p53 expression and consequently inhibits p53-mediated ISC apoptosis (FIG. 24A; see FIG. 31); (4) Slit-Robo signaling not only induces ISC proliferation (Zhou et al., 2013 Nature 501, 107-111), but also reduces p53-mediated ISC apoptosis (see FIGS. 25-28); cumulating in accelerated repair of acute gut injury (FIG. 24C).

Such findings indicate that, for example, induction of adult stem cell-mediated tissue repair by soluble Wnt/β-catenin agonists enhance host tolerance to intensive chemoradiotherapy for selective targeting of ICSCs carrying the APC and TP53 loss-of-function mutations, especially for treating late-staged cancer patients with systemic metastasis.

Accordingly, the present invention relates to compositions and methods for inducing intestinal stem cell homeogenesis and/or regeneration within intestinal tissue expressing Robo1 through administration of a Rspo1 agent and a Slit2 agent. Administration of such agents results in, for example, binding of the Rspo1 agent and Slit2 agent with Robo1, resulting in, for example, binding of the CC3 motif of Robo1 with LRP6, resulting in phosphorylation of LRP6, and ultimately, induction of intestinal stem cell homeogenesis and/or regeneration. In certain embodiments, such administration of a Rspo1 agent and a Slit2 agent is used to protect and/or prevent intestinal tissue damage resulting from exposure to an intestinal tissue damaging event (e.g., radiation). The agents and related compositions additionally find use in diagnostic and research settings.

For example, in certain embodiments, the present invention provides methods for treating and/or preventing intestinal tissue damage resulting from exposure to an intestinal stem cell damaging event. The present invention is not limited to particular methods for treating and/or preventing intestinal tissue damage resulting from exposure to an intestinal stem cell damaging event. In some embodiments, the methods comprise administering to a subject a composition comprising a Rspo1 agent and a Slit2 agent, wherein the intestinal tissue comprises Robo1 expression. In some embodiments, the Rspo1 agent is capable of binding the location on Robo1 where endogenous Rspo1 binds Robo1. In some embodiments, the Slit2 agent is capable of binding the location on Robo1 where endogenous Slit2 binds Robo1. In some embodiments, the administering of the composition results in induction of intestinal stem cell homeogenesis and/or regeneration. In some embodiments, the administering is a short-pulse administration (e.g., a three day short-pulse administration of a Rspo1 agent and a Slit2 agent). In some embodiments, the subject is a human being. In some embodiments, the human being is undergoing cancer undergoing radiation treatment.

The methods are not limited to a particular manner of treating and/or preventing intestinal tissue damage resulting from exposure to an intestinal stem cell damaging event. In some embodiments, the administering of the composition comprising a Rspo1 agent and a Slit2 agent results in binding of the Rspo1 agent with Robo1 and binding of the Slit2 agent with Robo1 within the intestinal tissue. In some embodiments, the binding of the Rspo1 agent with Robo1 and the binding of the Slit2 agent with Robo1 results in binding of Robo1 with LRP6. In some embodiments, the binding of Robo1 with LRP6 occurs at the CC3 motif within Robo1. In some embodiments, the binding of Robo1 with LRP6 results in phosphorylation of the LRP6. In some embodiments, the binding of the Rspo1 agent with Robo1 and the binding of the Slit2 agent with Robo1 results in association of Robo1 with LRG5. In some embodiments, the binding of the Rspo1 agent with Robo1 and the binding of the Slit2 agent with Robo1 results in β-catenin translocation. In some embodiments, the binding of the Rspo1 agent with Robo1 and the binding of the Slit2 agent with Robo1 results in activation of canonical Wnt signaling within the intestinal tissue. In some embodiments, binding of Rspo1 and Slit2 to Robo1 induces formation of Robo1-Lrp6-Lgr5 complex for activation of Wnt/β-catenin signaling. In some embodiments, such activation of Wnt/β-catenin signaling transcriptionally represses p53 expression and consequently inhibits p53-mediated ISC apoptosis.

In some embodiments, the composition comprising a Rspo1 agent and a Slit2 agent is administered concurrently with exposure to the intestinal stem cell damaging event. In some embodiments, the composition comprising a Rspo1 agent and a Slit2 agent is administered prior to exposure to the intestinal stem cell damaging event. In some embodiments, the composition comprising a Rspo1 agent and a Slit2 agent is administered after exposure to the intestinal stem cell damaging event. In some embodiments, the composition comprising a Rspo1 agent and a Slit2 agent is administered prior to, concurrently with, and/or after exposure to the intestinal stem cell damaging event.

The methods are not limited to a particular type of intestinal tissue. In some embodiments, the intestinal tissue is small intestinal tissue. In some embodiments, the intestinal tissue is the crypt region of the small intestine.

The methods are not limited to a particular type of intestinal stem cell damaging event. In some embodiments, the intestinal stem cell damaging event is an exposure to radiation. In some embodiments, the radiation is medical procedure related radiation. In some embodiments, medical procedure related radiation is selected from the group consisting of photon radiotherapy, particle beam radiation therapy, brachytherapy, interstitial irradiation, intracavity irradiation, radioimmunotherapy, and ionizing (electromagnetic) radiotherapy.

The methods are not limited to particular types of Rspo1 agents and/or Slit2 agents. In some embodiments, the Rspo1 agent is recombinant Rspo1 (see, e.g., Zhou, W. J., 2013 Nature 501: 107-111). In some embodiments, the Rspo1 agent is rRspo1-Fc (see, FIG. 32). In some embodiments, the recombinant Rspo1 agent is any type, kind or variant of a commercially available and/or empirically developed recombinant Rspo1. In some embodiments, the Slit2 agent is recombinant Slit2 (see, e.g., Zhou, W. J., et al., 2011 Cell Res. 21, 609-626). In some embodiments, the recombinant Slit2 agent is any type, kind or variant of a commercially available and/or empirically developed recombinant Slit2. In some embodiments, the Slit2 agent is rSlit2-Fc (see, FIG. 32).

In certain embodiments, the present invention provides methods for treating a subject having a disorder, comprising administering to the subject a medical procedure involving radiation, and further administering during the course of the medical procedure a composition comprising a Rspo1 agent and a Slit2 agent. In some embodiments, the administration of the composition treats and/or prevents intestinal tissue damage resulting from the medical procedure, wherein the intestinal tissue comprises Robo1 expression. In some embodiments, the Rspo1 agent is capable of binding the location on Robo1 where endogenous Rspo1 binds Robo1. In some embodiments, the Slit2 agent is capable of binding the location on Robo1 where endogenous Slit2 binds Robo1. In some embodiments, the administering is a short-pulse administration (e.g., a three day short-pulse administration of a Rspo1 agent and a Slit2 agent). In some embodiments, the subject is a human being (e.g., a human being undergoing radiation treatment). In some embodiments, the disorder is cancer. In some embodiments, the disorder is colon cancer. In some embodiments, the disorder is colorectal cancer.

In some embodiments, the administering of the composition results in induction of intestinal stem cell homeogenesis and/or regeneration. The methods are not limited to a particular manner of inducing intestinal stem cell homeogenesis and/or regeneration. In some embodiments, administering of the composition comprising a Rspo1 agent and a Slit2 agent results in binding of the Rspo1 agent with Robo1 and binding of the Slit2 agent with Robo1 within the intestinal tissue. In some embodiments, the binding of the Rspo1 agent with Robo1 and the binding of the Slit2 agent with Robo1 results in binding of Robo1 with LRP6. In some embodiments, the binding of Robo1 with LRP6 occurs at the CC3 motif within Robo1. In some embodiments, the binding of Robo1 with LRP6 results in phosphorylation of the LRP6. In some embodiments, the binding of the Rspo1 agent with Robo1 and the binding of the Slit2 agent with Robo1 results in association of Robo1 with LRG5. In some embodiments, the binding of the Rspo1 agent with Robo1 and the binding of the Slit2 agent with Robo1 results in β-catenin translocation. In some embodiments, the binding of the Rspo1 agent with Robo1 and the binding of the Slit2 agent with Robo1 results in activation of canonical Wnt signaling within the intestinal tissue. In some embodiments, binding of Rspo1 and Slit2 to Robo1 induces formation of Robo1-Lrp6-Lgr5 complex for activation of Wnt/β-catenin signaling. In some embodiments, such activation of Wnt/β-catenin signaling transcriptionally represses p53 expression and consequently inhibits p53-mediated ISC apoptosis.

The methods are not limited to a particular type of intestinal tissue. In some embodiments, the intestinal tissue is small intestinal tissue. In some embodiments, the intestinal tissue is the crypt region of the small intestine.

The methods are not limited to a particular type of medical procedure involving radiation. In some embodiments, the medical procedure involving radiation is selected from the group consisting of photon radiotherapy, particle beam radiation therapy, brachytherapy, interstitial irradiation, intracavity irradiation, radioimmunotherapy, and ionizing (electromagnetic) radiotherapy.

The methods are not limited to particular types of Rspo1 agents and/or Slit2 agents. In some embodiments, the Rspo1 agent is recombinant Rspo1 (see, e.g., Zhou, W. J., 2013 Nature 501: 107-111). In some embodiments, the Rspo1 agent is rRspo1-Fc (see, FIG. 32). In some embodiments, the recombinant Rspo1 agent is any type, kind or variant of a commercially available and/or empirically developed recombinant Rspo1. In some embodiments, the Slit2 agent is recombinant Slit2 (see, e.g., Zhou, W. J., et al., 2011 Cell Res. 21, 609-626). In some embodiments, the recombinant Slit2 agent is any type, kind or variant of a commercially available and/or empirically developed recombinant Slit2. In some embodiments, the Slit2 agent is rSlit2-Fc (see, FIG. 32).

In certain embodiments, the present invention provides methods for inducing intestinal stem cell homeogenesis and/or regeneration within an intestinal tissue sample, comprising exposing to the intestinal tissue sample a composition comprising a Rspo1 agent and a Slit2 agent, wherein the intestinal tissue sample comprises Robo1 expression. In some embodiments, the Rspo1 agent is capable of binding the location on Robo1 where endogenous Rspo1 binds Robo1, and wherein the Slit2 agent is capable of binding the location on Robo1 where endogenous Slit2 binds Robo1. In some embodiments, the exposing is a short-pulse administration (e.g., a three day short-pulse administration of a Rspo1 agent and a Slit2 agent).

In some embodiments, the intestinal tissue sample is an in vivo sample. In some embodiments, the intestinal tissue sample is an in vitro sample. In some embodiments, the intestinal tissue sample is within a human subject. In some embodiments, the intestinal tissue sample is an ex vivo sample.

In some embodiments, the exposure of the composition to the intestinal tissue sample results in binding of the Rspo1 agent with Robo1, and binding of the Slit2 agent with Robo1. In some embodiments, the binding of the Rspo1 agent with Robo1, and binding of the Slit2 agent with Robo1 results in induction of intestinal stem cell homeogenesis and/or regeneration. In some embodiments, the binding of the Rspo1 agent with Robo1 and the binding of the Slit2 agent with Robo1 results in binding of Robo1 with LRP6. In some embodiments, the binding of Robo1 with LRP6 occurs at the CC3 motif within Robo1. In some embodiments, the binding of Robo1 with LRP6 results in phosphorylation of the LRP6. In some embodiments, the binding of the Rspo1 agent with Robo1 and the binding of the Slit2 agent with Robo1 results in association of Robo1 with LRG5. In some embodiments, the binding of the Rspo1 agent with Robo1 and the binding of the Slit2 agent with Robo1 results in β-catenin translocation. In some embodiments, the binding of the Rspo1 agent with Robo1 and the binding of the Slit2 agent with Robo1 results in activation of canonical Wnt signaling within the intestinal tissue. In some embodiments, binding of Rspo1 and Slit2 to Robo1 induces formation of Robo1-Lrp6-Lgr5 complex for activation of Wnt/β-catenin signaling. In some embodiments, such activation of Wnt/β-catenin signaling transcriptionally represses p53 expression and consequently inhibits p53-mediated ISC apoptosis.

The methods are not limited to a particular type of intestinal tissue within the intestinal tissue sample. In some embodiments, the intestinal tissue sample comprises small intestinal tissue. In some embodiments, the intestinal tissue sample comprises the crypt region of the small intestine.

The methods are not limited to particular types of Rspo1 agents and/or Slit2 agents. In some embodiments, the Rspo1 agent is recombinant Rspo1 (see, e.g., Zhou, W. J., 2013 Nature 501: 107-111). In some embodiments, the Rspo1 agent is rRspo1-Fc (see, FIG. 32). In some embodiments, the recombinant Rspo1 agent is any type, kind or variant of a commercially available and/or empirically developed recombinant Rspo1. In some embodiments, the Slit2 agent is recombinant Slit2 (see, e.g., Zhou, W. J., et al., 2011 Cell Res. 21, 609-626). In some embodiments, the recombinant Slit2 agent is any type, kind or variant of a commercially available and/or empirically developed recombinant Slit2. In some embodiments, the Slit2 agent is rSlit2-Fc (see, FIG. 32).

Additional embodiments will be apparent to persons skilled in the relevant art based on the teachings contained herein.

BRIEF DESCRIPTION OF THE DRAWINGS

FIG. 18 describes how Slit2 fails to increase Rsop1 binding to Robo1 while Rspo1 fails to increase Slit2 binding to Robo1. Pro-A beads were first incubated with hIgG and Robo1-Fc. After washing, they were incubated with rSlit2 and/or rRspo1, followed by immunoblotting for rSlit2 (A) and rRspo1 (B). 5% of total inputs were also directed immunoblotted for rSlit2 (A) and rRspo1 (B). Results are representatives of more than three separate experiments.

Figure 1:
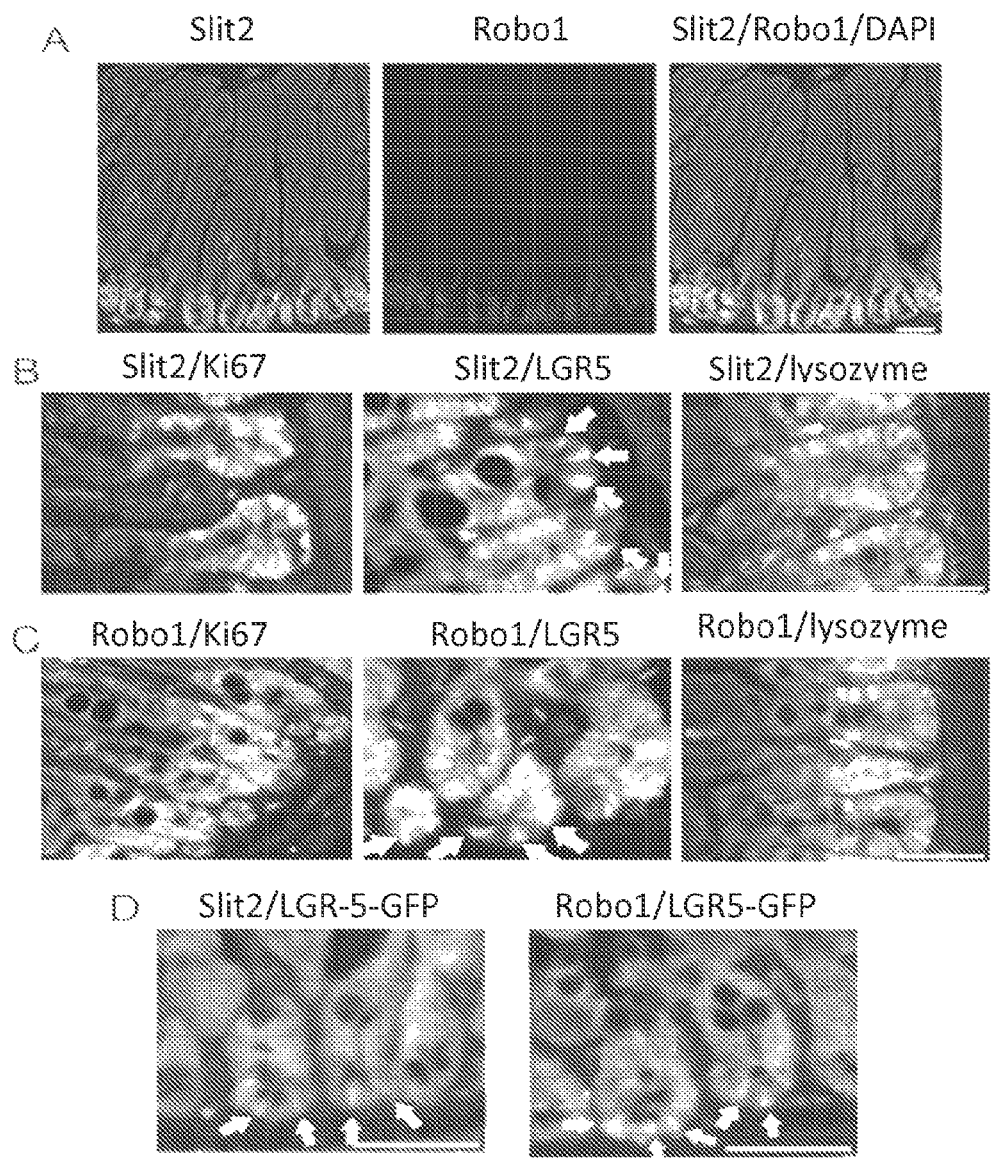
FIG. 1 describes expression of Slit2 and Robo1 in mouse small intestine. (A) Expression and co-localization of Slit2 and Robo1 mRNAs in the crypt of small intestine. Slit2 and Robo1 mRNAs in the Wt small intestines were detected by using the DIG- or biotin-conjugated antisense Slit2 and Robo1 mRNA probes. Slides were counterstained with DAPI. Immunofluorescent images were observed under a laser scanning confocal microscope, and the recorded fluorescent images were then merged. (B-D) Cellular distribution of mRNAs for Slit2 (B and D) and Robo1 (C and D). Slit2, Robo1, Ki67 (a marker for proliferating TA cells), LGR5 (a marker for ISCs), and lysozyme (a marker for Paneth cells) were found at the crypt of small intestines using FISH (Slit2 and Robo1) and immunofluorescent staining with their respective Abs (Ki67, LGR5, lysozyme and GFP). Alternatively, the intestinal tissues isolated from LGR5-GFP mice (Barker et al., 2007 Nature 449, 1003-1007) were stained by the anti-GFP Ab for LGR5-positive cells (D). White arrows indicate LGR5-positive cells co-localized with Slit2 or Robo1 mRNA (B and C). Results represent at least three separate experiments. Bars, 50 µm for A-C.

Rspo1/Slit2 ameliorates IR-mediated inhibition of intestinal organoids. On day 1, Lgr5$^{high}$ ISCs were cultured the standard stem cell culture medium contains 0.5 µg/ml rRspo1 without rSlit2 (−) or 1 µg/ml rRspo1 plus 1 µg/ml rSlit2 (rRspo1/rSlit2). On day 2, they received 12 Gy IR in the presence or absence of added rRspo1/rSlit2. The numbers and sizes of intestinal organoids were determined on day 14. Results represent three or more separate experiments (A, C, H, J, K, M, N) or the mean±S.D. of three or more separate experiments (B, D-G, I, L, N). Bars, 200 µm for N. *, p<0.05 (Mann-Whitney test).

Figure 32:
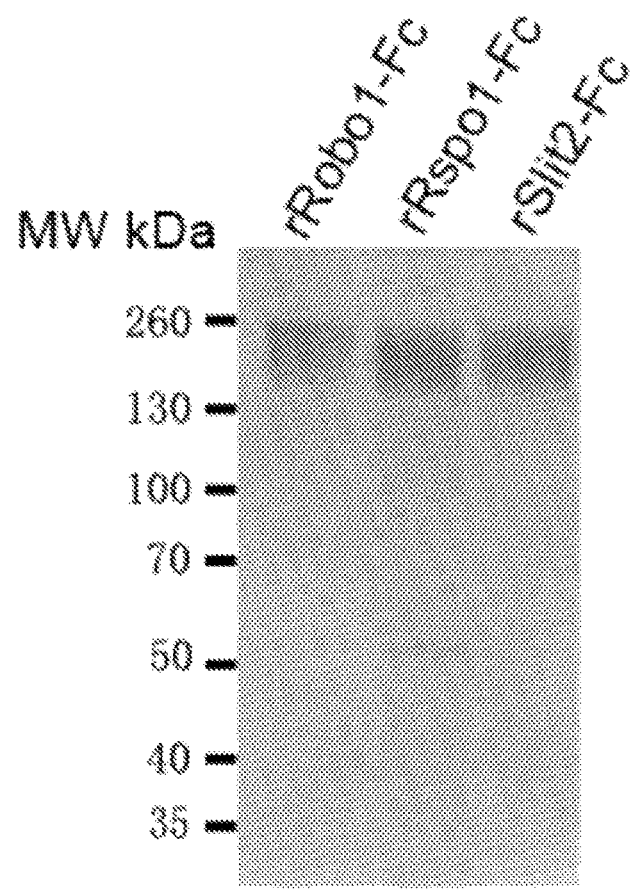

FIG. 32 shows purification of recombinant Fc-fusion chimeras. Coomassie blue staining of purified rRobo1-Fc, rRspo1-Fc and rSlit2-Fc. Samples were run under-non-reducing conditions. Results are representative of three or more separate protein preparations.

DEFINITIONS

To facilitate an understanding of the present invention, a number of terms and phrases are defined below.

As used herein, the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

The term "derivative" of a small molecule, as used herein, refers to a chemically modified small molecule wherein the chemical modification takes place either at a functional group of the small molecule (e.g., compound) or on the aromatic ring.

As used herein, the term "subject" refers to organisms to be treated by the methods and agents of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a Rspo1 agent and a Slit2 agent and optionally one or more other agents) for purposes of inducing ISC homeogenesis and/or regeneration (e.g., for purposes of preventing and/or treating intestinal tissue damage resulting from an intestinal tissue damaging event (e.g., radiation exposure)).

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

In some embodiments, the "target cells" of the compositions and methods of the present invention include, refer to, but are not limited to, lymphoid cells or cancer cells. Lymphoid cells include B cells, T cells, and granulocytes. Granulocyctes include eosinophils and macrophages. In some embodiments, target cells are continuously cultured cells or uncultered cells obtained from patient biopsies.

As used herein, the term "co-administration" refers to the administration of at least two agent(s) (e.g., an agent of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the terms "non-specific binding" and "background binding" when used in reference to the interaction of a molecule with a protein or enzyme refers to an interaction that is not dependent on the presence of a particular structure.

As used herein, the term "modulate" refers to the activity of an agent (e.g., a peptide or small molecule of the present invention) to affect (e.g., to promote or retard) an aspect of cellular function, including, but not limited to, enzymatic activity, maturation, cell growth, replication, proliferation, and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

The present invention relates to compositions and methods for inducing intestinal stem cell homeogenesis and/or regeneration within intestinal tissue expressing Robo1 through administration of a Rspo1 agent and a Slit2 agent. Administration of such agents results in, for example, binding of the Rspo1 agent and Slit2 agent with Robo1, resulting in, for example, binding of the CC3 motif of Robo1 with LRP6, resulting in phosphorylation of LRP6, and ultimately, induction of intestinal stem cell homeogenesis and/or regeneration. In certain embodiments, such administration of a Rspo1 agent and a Slit2 agent is used to protect and/or prevent intestinal tissue damage resulting from exposure to an intestinal tissue damaging event (e.g., radiation). The agents and related compositions additionally find use in diagnostic and research settings.

Exemplary compositions and methods of the present invention are described in more detail in the following sections: I. Induction of Intestinal Stem Cell Homeogenesis/Regeneration; II. Exemplary Agents; III. Therapeutic Applications; IV. Pharmaceutical Compositions, Formulations, and Exemplary Administration Routes and Dosing Considerations; and V. Drug Screens.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Induction of Intestinal Stem Cell Homeogenesis/Regeneration

The epithelium of small intestine is organized into two morphologically and functionally distinct regions called the crypt and the villus. The crypt consists of intestinal stem cells (ISCs) and proliferating transit amplifying (TA) cells, which are essential for the astonishingly fast and continuous renewal of differentiated progeny cells and for maintaining homeostasis of intestinal epithelium. ISCs include a fast-cycling subpopulation, called crypt base columnar (CBC) cells, expressing leucine-rich repeat containing G protein-coupled receptor 5 (LGR5), CD133 and Sox9 at the bottom of the crypt (see, e.g., Tian et al., 2011 Nature 478, 255-259; Takeda et al., 2011 Science 334, 1420-1424; Yan et al., 2012 Proc. Natl. Acad. Sci. USA 109, 466-471). TA cells, located above the +4 position, proliferate and expand rapidly and migrate along the inner surface of the crypt where they differentiate into either granular secretory cells (Paneth, goblet and enteroendocrine) or columnar absorptive enterocytes. Whereas other differentiated cells proliferate and migrate toward the villus, Paneth cells migrate toward the bottom of the intestinal crypt, where they intercalate with LGR5-positive ISCs. Extensive efforts have been made to identify the regulatory molecules that ensure the long-term self-renewal of ISCs (see, e.g., Clevers and Nusse, 2012 Cell 149, 1192-1205).

Wnt/β-catenin signal transduction is a main driving force for intestinal morphogenesis and homeostasis (see, e.g., Schuijers and Clevers, 2012 EMBO J. 31, 2685-2696; Clevers and Nusse, 2012 Cell 149, 1192-1205). In the absence of Wnts, cytoplasmic β-catenin is kept at low levels by its binding to the cytoplasmic segment of E-cadherin enriched at adherens junctions and by its degradation through a destruction complex consisting of axin, glycogen synthase kinase 3 (GSK3), adenomatous polyposis coli (APC), casein kinase Iα (CKIα) and β-catenin itself (see, e.g., MacDonald et al., 2009 Dev. Cell. 17, 9-26). Binding of Wnt ligands, such as Wnt3a, to the 7-span transmembrane Frizzled receptors (Fzd) recruits the co-receptors of single-span LRP5/6. The Wnt3a-Fzd-LRP5/6 complex activates Dishevelled (Dvl) and promotes LRP6 phosphorylation, including threonine$^{1493}$ (T$^{1493}$) by CK1γ and serine$^{1490}$ (S$^{1490}$) by GSK3β. Through its five reiterated docking sites PPPSPxS (P, proline; S, serine or threonine; x, a variable residue), phosphorylated LRP6 engages with axin and destabilizes the destruction complex for cytoplasmic accumulation and nuclear translocation of β-catenin, where the later displaces Groucho, a transcriptional repressor, and activates the family of T-cell specific transcription factors/lymphoid enhancer-binding factors (TCF/LEF) for transcriptional up-regulation of such target genes as c-Myc, ephB2, ephB3, and Caudal type homeobox (Cdx) 1 and 2 (see, e.g., Beck and Stringer, 2010 Biochem. Soc. Trans. 38, 353-357). Notably, subtle alteration in the intensity, amplitude, location and duration of canonical Wnt signaling fundamentally affects intestinal development and regeneration (see, e.g., Nelson and Nusse, 2004 Science 303, 1483-1487).

The R(oof plate-specific) spondin family of Wnt agonists includes Rspo1-4 in all vertebrates, which share the common domain architecture, including two furin-like cysteine-rich repeats near the amino terminus followed by one thrombospondin type 1-like repeat (TSR) and a carboxyl-terminus with positively charged amino acid residues (see, e.g., Schuijers and Clevers, 2012 EMBO J. 31, 2685-2696). Rspo1, a secreted ~35 kDa molecule, synergizes with soluble Wnt3a to induce LRP6 phosphorylation and to promote cytoplasmic stabilization and nuclear accumulation of β-catenin for cellular proliferation, differentiation and stem cell maintenance (see, e.g., de Lau et al., 2011 Nature 476, 293-297; Glinka et al., 2011 EMBO Rep. 12, 1055-1061; Carmon et al., 2011 Proc. Natl. Acad. Sci. USA. 108, 11452-11457; Carmon et al., 2012 Mol. Cell. Biol. 32, 2054-2064; Gong et al., 2012 PLoS One 7, e37137). Rspo1 transgene induces a robust enlargement of small and larger intestines (see, e.g., Kim et al., 2005 Science 309, 1256-1259), whereas administration of recombinant or adenoviral Rspo1 alleviates intestinal injury and oral mucositis induced by chemoradiotherapy (see, e.g., Kim et al., 2005 Science 309, 1256-1259; Zhao et al., 2009 Proc. Natl. Acad. Sci. USA 106, 2331-2336; Bhanja et al., 2009 PLoS One 4, e8014), experimental colitis (Zhao et al., 2007 Gastroenterology 132, 1331-1343), and systemic graft-versus-host disease (GVHD) (see, e.g., Takashima et al., 2011 J. Exp. Med. 208, 285-294). In the presence of Wnt3a, Rspo1 is absolutely required for in vitro culture of intestinal organoids derived from isolated intestinal crypts and LGR5$^+$ ISCs (see, e.g., Sato et al., 2009; Nature 459, 262-265; Ootani et al., 2009 Nature Medicine 15, 701-706; Jung et al., 2011 Nat. Med. 17, 1225-1227) or pluripotent stem cells (see, e.g., Spence et al., 2011 Nature. 470, 105-109). Mechanistically, R-spondin proteins act synergistically with Wnt, Fzd, LRP6 and LGR4-6 (see, e.g., Kazanskaya et al., 2004 Dev. Cell 7, 525-534; Kim et al., 2005 Science 309, 1256-1259; Nam et al., 2006 J. Biol. Chem. 281, 13247-13257; Wei et al., 2007 J. Biol. Chem. 282, 15903-15911; Binnerts et al., 2007 Proc. Natl. Acad. Sci. USA 104, 14700-14705; de Lau et al., 2011 Nature 476, 293-297; Glinka et al., 2011 EMBO Rep. 12, 1055-1061; Carmon et al., 2011 Proc. Natl. Acad. Sci. USA. 108, 11452-11457; Carmon et al., 2012 Mol. Cell. Biol. 32, 2054-2064; Gong et al., 2012 PLoS One 7, e37137; Ruffner et al., 2012 PLoS One 7, e40976). For example, Rspo1 binds to LGR4-6 with high affinity and enhances LRP6 phosphorylation at serine 1490 (pS$^{1490}$ LRP6) (see, e.g., de Lau et al., 2011 Nature 476, 293-297; Glinka et al., 2011 EMBO Rep. 12, 1055-1061; Carmon et al., 2011 Proc. Natl. Acad. Sci. USA. 108, 11452-11457; Carmon et al., 2012 Mol. Cell. Biol. 32, 2054-2064; Gong et al., 2012 PLoS One 7, e37137; Ruffner et al., 2012 PLoS One 7, e40976). Rspo1 also competes with ZNRF3, an E3 ubiquitin ligase, for reducing ZNRF3-mediated degradation of cell-surface Fzd and LRP6 (see, e.g., Binnerts et al., 2007 Proc. Natl. Acad. Sci. USA 104, 14700-14705; Hao et al., 2012 Nature 485, 195-200). Importantly, conditional deletion of Lgr4/5 in the intestinal epithelium reduces intestinal crypts and retards villus repopulation (see, e.g., de Lau et al., 2011 Nature 476, 293-297). However, it is unknown whether Rspo1 administration can rescue intestinal atrophy in the conditional Lgr4/5-deficient mice as well as how Rspo1 potentiates LRP6 phosphorylation.

Acting as "a guardian of the genome", tumor suppressor protein p53, also known as TP53 in humans and Trp53 in mice, maintains the genome integrity and stability (Wade et al., 2013 Cancer 13, 83-96). Mice lacking p53 (Trp53$^{-/-}$) spontaneously develop numerous types of lymphoma, leukemia, sarcoma and carcinoma within 6 months (Jackson and Lozano, 2013 Oncogene 32, 4325-4330). Loss-of-function mutations of TP53 exist in >50% of all human cancers (Kinzler and Vogelstein, 1996 Cell 87, 159-170; Vogelstein et al., 2013 Science 339, 1546-1558). In unstressed conditions, p53 forms a heterodimer with Mdm2 protein, an important negative regulator, which functions as an E3 ubiquitin ligase for p53 constitutive ubiquitination and degradation. However, cellular stimuli stabilize p53 to transactivate its targeting genes, such as PUMA, Bax and Noxa, for induction of cellular apoptosis. In addition, a variety of transcription factors, miRNAs, DNA methylation and insulator proteins also tightly regulate the transcriptional expression of p53 (Saldaña-Meyer and Recillas-Targa, 2011 Epigenetics 6, 1068-1077). Importantly, small molecule inhibitors for p53-mediated apoptosis are being clinically tested to treat cancers (Bai and Wang, 2014 Annu Rev. Med. 65, 139-155).

The Slit family of guidance cues interacts with the Robo family of single-span transmembrane receptors in a wide variety of physiological processes requiring cell migration. There are three members of Slit (Slit1, 2 and 3) and four members of Robo (Robo1, 2, 3 and 4) in mammals. Slit-Robo signaling regulates neuronal migration and axon pathfinding (see, e.g., Dickson and Gilestro 2006 Annu Rev. Cell Dev. Biol. 22, 651-675; Ypsilanti et al., 2010 Development 137, 1939-1952), leukocyte chemotaxis (see, e.g., Wu et al., 2001 Nature 410, 948-952; Guan et al., 2003 J. Immunol. 171, 6519-6526; Kanellis et al., 2004 Am. J. Pathol. 165, 341-352; Chen et al., 2004 J. Immunol. 173, 5914-5917; Prasad et al., 2007 J. Leukoc. Biol. 82, 465-476; Altay et al., 2007 Exp. Neurol. 207, 186-194; Ye et al., 2010 J. Immunol. 185, 6294-6305), tumor cell migration (see, e.g., Prasad et al., 2004 J. Biol. Chem. 279, 9115-9124; Mertsch et al., 2008 J. Neurooncol. 87, 1-7; Stella et al., 2009 Mol. Biol. Cell 20, 642-657; Yuasa-Kawada et al., 2009 Proc. Natl. Acad. Sci. USA 106, 14530-14535), and angiogenesis and/or angiostasis (see, e.g., Wang et al., 2003 Cancer Cell 4, 19-29; Bedell et al., 2005 Proc. Natl. Acad. Sci. USA 102, 6373-6378; Seth et al., 2005 Biochem. Biophys. Res. Commun. 332, 533-54; Suchting et al., 2005 FASEB J. 19, 121-123; Wang et al., 2008 Cancer Sci. 99, 510-517; Jones et al, 2008 Nat. Med. 14, 448-453; Jones et al., 2009 Nat. Cell Biol. 11, 1325-1331; Zhang et al., 2009 Blood 114, 4300-4309; Urbich et al., 2009 Blood 113, 5669-5679; Yang et al., 2010 Biochem. Biophys. Res. Commun. 396, 571-577; Dunaway et al., 2011 Mol. Cell. Biol. 31, 404-416; Han and Geng, 2011 Acta Pharmacol. Sin. 32, 1327-1336; Guijarro-Muñoz et al., 2012 Exp. Cell Res. 318, 371-378; Guo et al., 2012 Reprod. Sci. [Epub ahead of print]). Slit-Robo signaling also inhibits E-cadherin-mediated cell adhesion during the lumen formation between apical cardioblasts (see, e.g., Qian et al., 2005 Curr. Biol. 15, 2271-2278; MacMullin and Jacobs, 2006 Dev. Biol. 293, 154-164; Santiago et al., 2006 Proc. Natl. Acad. Sci. USA 103, 12441-12446; Santiago et al., 2008 J. Cell Biol. 182, 241-248; Medioni et al., 2008 J. Cell Biol. 182, 249-261; Fish et al., 2011 Development 138, 1409-1419) and induces malignant transformation in colorectal and embryonic kidney epithelial cells (see, e.g., Zhou et al., 2011 Cell Res. 21, 609-626).

The gastrointestinal epithelium constantly renews every 3-5 days in adults. Acting preferentially upon proliferating ISCs (CBCs) residing at the intestinal crypts, cytotoxic agents and ionizing irradiation, caused by intensive chemoradiotherapy for cancer eradication, radiation accidents and possible terrorist attacks, prevent the constant epithelialization of the intestinal villi and elicit malabsorption, electrolyte imbalance, diarrhea, weight loss, bacteremia, aberrant inflammatory leukocytes, cytokine cascades and ultimately death. For example, endotoxin, in the outer leaflet of the outer membrane of Gram-negative bacteria that colonize the intestinal tract in a large quantity, translocates into the bloodstream after chemoradiation-induced mucosal injury, causing cardiovascular collapse, respiratory failure, coagulopathy and systemic inflammation during endotoxinemia. Notably, a combination therapy of bactericidal/permeability-increasing protein (BPI) that binds and neutralizes endotoxin plus a wide-spectrum antibiotics fluoroquinolone that inhibits intestinal bacteria has been shown to moderately improve overall survival after sub-lethal doses of radiation (see, e.g., Guinan et al., 2011 Sci. Transl. Med. 3, 110ra118). Although flagellin, a bacterial protein that activates nuclear factor-κB signaling through Toll-like receptor 5, is radio-protective in mouse and primate models (see, e.g., Burdelya et al., 2008 Science 320, 226-230), the physiologic roles and significance of nuclear factor-κB signaling in intestinal development and homeostasis are less well understood.

Figure 24:
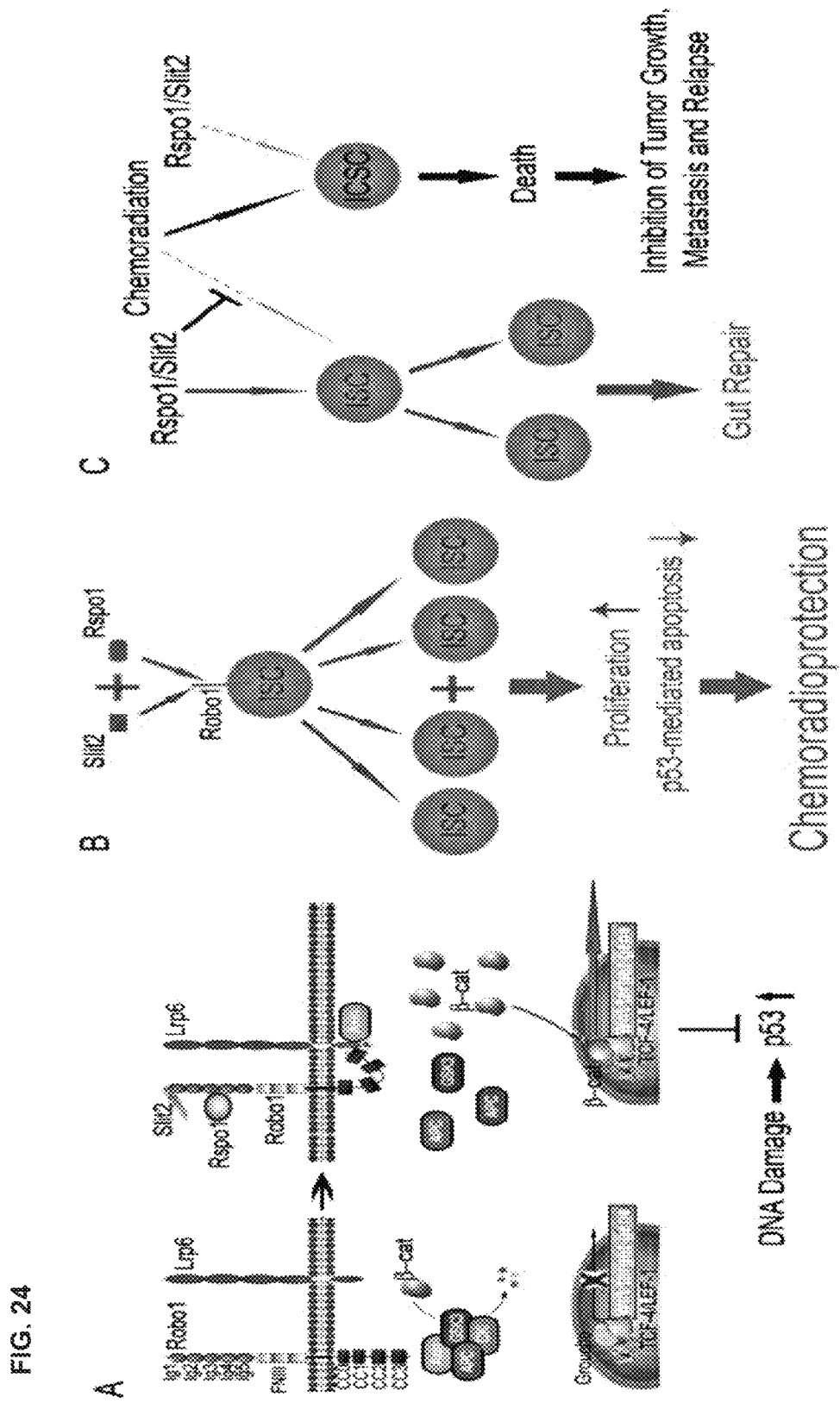
FIG. 24 shows a schematic showing Slit2 and Rspo1 binding to Robo1 acts LRP6 for synergistic activation of canonical Wnt signaling (A), which cooperatively increases the number of ISCs for accelerated gut repair and enhanced resistance to chemoradiation (B), and gut repair, inhibition of tumor growth, metastasis and relapse (C).
Figure 25:
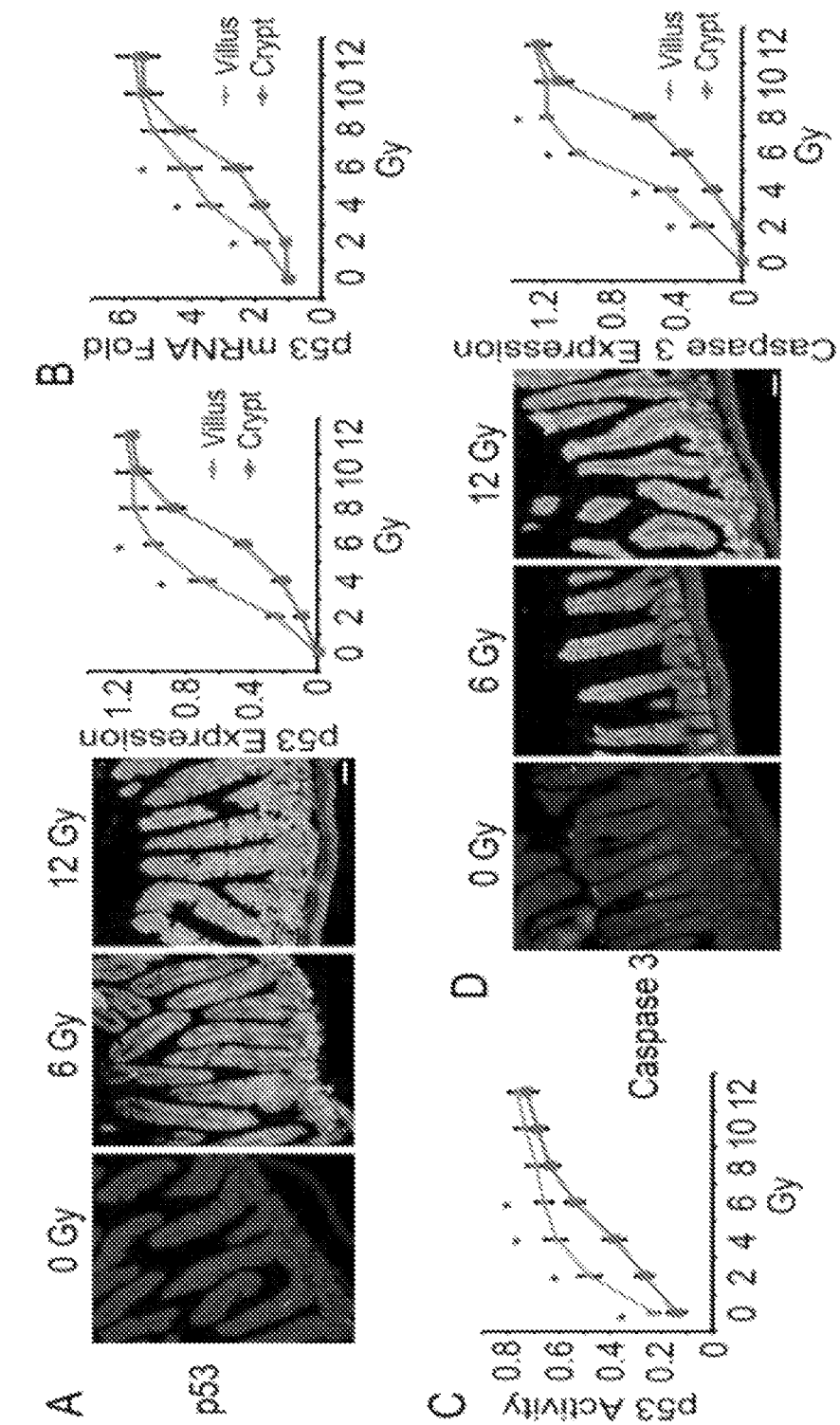
FIG. 25 shows that IR induces the intestinal expression of p53 and active caspase 3. On day 1, wild-type C57 mice received whole body IR at 0, 2, 4, 6, 8, 10 or 12 Gy. On day 3, they were euthanized and the small intestinal tissues were stained for p53 (A) and active caspase 3 (D). In addition, the intestinal villi and crypts were isolated for determination of the p53 mRNA (B) and the p53 transcriptional activity (C). Slides were counterstained with DAPI to delineate the nuclei. Results are representative images and the mean±S.D. of 10 tissue sections/mouse (8 weeks old; 3 mice/group). Bars, 50 μm for A, and D. *, $p<0.05$ (Kruskal-Wallis test).

Experiments conducted during the course of developing embodiments for the present invention tested whether induction of tissue-specific stem cells mitigates chemoradiation-induced tissue injury and prolongs overall survival. It was found that intestinal stem cells (ISCs) expressed a transmembrane receptor Roundabout 1 (Robo1). In addition, it was found that R-spondin 1 (Rspo1; a Wnt agonist) and Slit2 (a guidance cue) bound to the extracellular domains of Robo1 at distinctive sites, whereas the cytoplasmic CC3 motif of Robo1 bound to LRP6 and promoted LRP6 phosphorylation and association with LGR5, leading to synergistic activation of canonical Wnt signaling and cooperative induction of ISCs for intestinal homeostasis and regeneration. Indeed, such experiments resulted in the discovery that ISCs and proliferating TA cells residing at the crypt of small intestine express Slit2 and Robo1. Engagement of Robo1 by Slit2 was shown to induce LRP6 phosphorylation and association with LGR5, β-catenin translocation, TCF/LEF promoter activation and canonical Wnt targeting gene expression (FIG. 24). Even a partial genetic deletion of Robo1/2 was shown to be sufficient to reduce ISCs, TA cells and enterocytes, leading to villus hypotrophy, which were further verified by treating Wt mice with R5 to transiently inhibit Slit2 binding to Robo1. In contrast, Slit2 transgene was shown to augment the numbers of ISCs, TA cells and enterocytes, leading to villus hypertrophy and enhanced resistance to chemotherapy (FIG. 24). Mechanistically, Robo1/2 partial deficiency, R5 treatment or ectopic expression of the cytoplasmic CC3 motif of Robo1 was shown to inactivate β-catenin for suppressing the expression of canonical Wnt targeting genes, whereas Slit2 transgene was shown to be capable of activating β-catenin for inducing the expression of canonical Wnt targeting genes. The successful "rescue" of the Robo1$^{-/+}$/2$^{-/+}$ intestinal organoids by adenoviral β-catenin demonstrates the importance of Slit-Robo signaling, at the upstream of β-catenin activation, in intestinal homeostasis and regeneration. Such experiments demonstrated the significance of functional cooperation between Rspo1 and Slit2 for optimal activation of Wnt/β-catenin signaling in Robo1-expressing ISCs for intestinal repair and chemoradioprotection, without concomitantly decreasing the sensitivity of intestinal cancer to chemotherapy. Moreover, engagement of Robo1 by Rspo1/Slit2 was shown to transcriptionally suppressed ionizing radiation (IR)-induced p53 expression and its apoptotic activity in Lgr5$^{high}$ ISCs, leading to reduced gut injury in response to IR.

Figure 29:
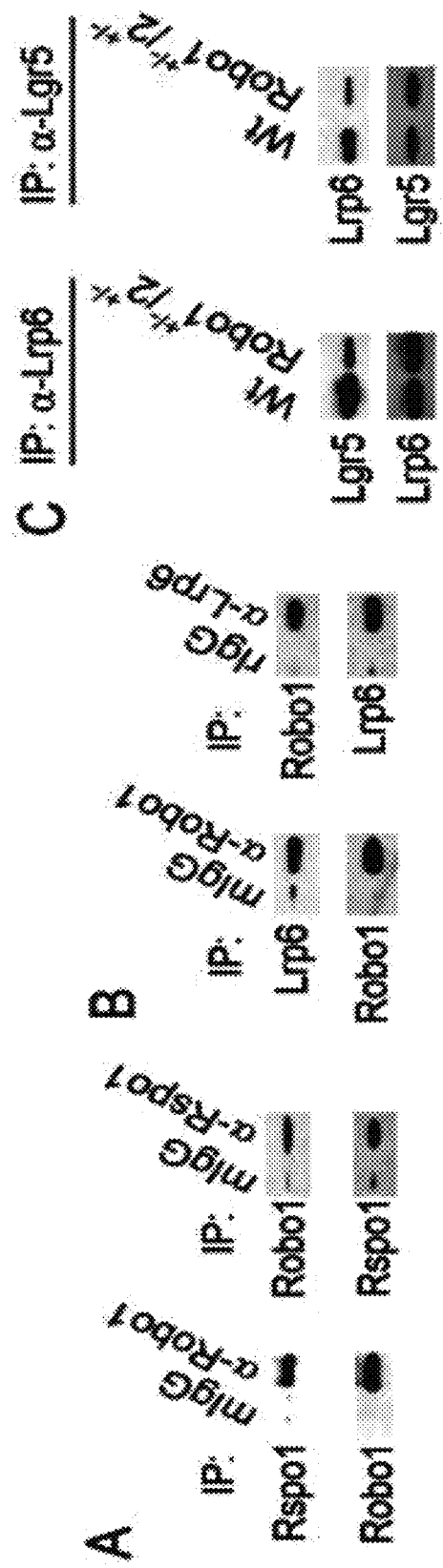
FIG. 29 demonstrates that Rspo1 binds to Robo1 and promotes formation of Robo1-Lrp6-Lgr5 complex. (A) Robo1 associates with Rspo1. Robo1 or Rspo1 was immunoprecipitated from the Wt crypt lysates, followed by immunoblotting for Rspo1 (~35 kDa) and Robo1 (~200 kDa). (B) Robo1 associates with Lrp6. Robo1 or Lrp6 was immunoprecipitated from the Wt crypt lysates, followed by immunoblotting for Lrp6 (~200 kDa) and Robo1. (C) Robo1 promotes Lrp6 association with Lgr5. Lrp6 and Lgr5 in the lysates of wild-type and Robo1/2 mutant intestinal crypts were immunoprecipitated, followed by immunoblotting for them. Results represent three or more separate experiments.
Figure 30:
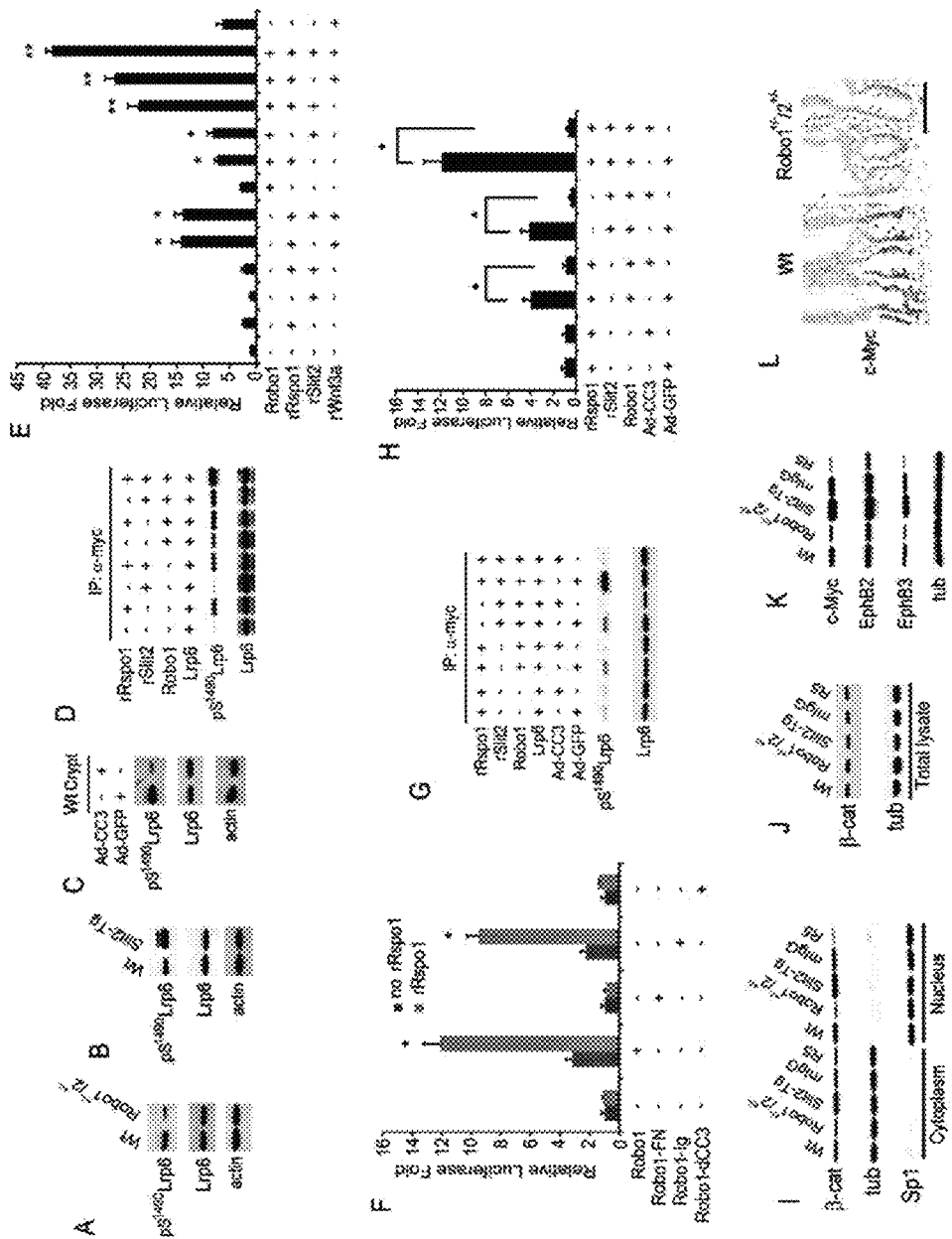
FIG. 30 demonstrates the significance of Robo1-Lrp6 complex in canonical Wnt activation. (A to C) Slit-Robo signaling modulates Lrp6 phosphorylation. The intestinal crypt lysates of wild-type littermates (Wt) and Robo1$^{-/+}$/2$^{-/+}$ mice (A) and wild-type C57 (Wt) and Slit2-Tg mice (B) were immunoblotted for pS$^{1490}$Lrp6, Lrp6 and β-actin (actin). Alternatively, the intestinal crypts isolated from wild-type C57 mice (Wt; C) were infected with Ad-GFP or Ad-CC3 and the lysates were immunoblotted as above. (D) Slit2 potentiates Rspo1-induced Lrp6 phosphorylation. 293 cells, transfected with Lrp6 and/or Robo1 plasmids, were incubated with rRspo1 and/or rSlit2. Their lysates were immunoprecipitated for Lrp6 (myc), followed by immunoblotting for pS$^{1490}$Lrp6 and Lrp6. (E and F) Slit2 potentiates Tcf/Lef promoter activity elicited by Rspo1 and/or Wnt3a. 293 cells were co-transfected with the plasmids of Tcf/Lef promoter luciferase reporter, β-gal, Robo1 (E), Robo1-FN, Robo1-Ig or Robo1-dCC3 (F). Following incubation with rRspo1 in the presence or absence of rSlit2 and/or rWnt3a (5036-WN-010, R&D Systems), the luciferase activities of the Tcf/Lef promoter in the cell lysates were determined and normalized to β-gal for expression efficiency. (G and H) CC3 suppresses Rspo1/Slit2-induced Lrp6 phosphorylation and Tcf/Lef promoter activity. 293 cells were transfected with Lrp6 and Robo1 plasmids, infected with Ad-GFP or Ad-CC3, and incubated with rRspo1 and/or rSlit2. Cell lysates were immunoprecipitated for Lrp6 (myc), followed by immunoblotting for pS$^{1490}$Lrp6 and Lrp6 (G). Alternatively, 293 cells were co-transfected with the plasmids for Tcf/Lef promoter luciferase reporter, β-gal and Robo1 and infected by Ad-GFP or Ad-CC3. Following incubation with rRspo1 and/or rSlit2, the luciferase activities of Tcf/Lef promoter were measured (H). (I and J) Slit-Robo signaling modulates β-catenin translocation. Small intestines were obtained from Wt littermates, Robo1$^{-/+}$/2$^{-/+}$ and Slit2-Tg mice or mIgG and R5-treated Wt mice. The intestinal lysates were fractionated and immunoblotted for β-catenin (~90 kDa), α-tubulin (tub; a cytoplasmic marker) and Sp1 (a nucleus marker; I). Alternatively, the total lysates were immunoblotted for β-catenin and α-tubulin (J). (K and L) Slit-Robo signaling regulates canonical Wnt signaling. The total small intestinal lysates of Wt littermates and Robo1$^{-/+}$/2$^{-/+}$ mice were immunoblotted for c-Myc, EphB2 and EphB3 (K). Alternatively, the intestinal tissue specimens obtained from Wt littermates, Robo1$^{-/+}$/2$^{-/+}$ and Slit2-Tg mice or mIgG and R5-treated Wt mice were immunohistochemically stained for c-Myc (L). Results are representatives of three or more separate experiments (A-D, G, I-K, L) the mean±S.D. of three or more independent experiments (E, F, H). All mice used were 8 weeks old. Bar, 50 μm for L. *, p<0.05; **, p<0.01 (Mann-Whitney test).
Figure 31:
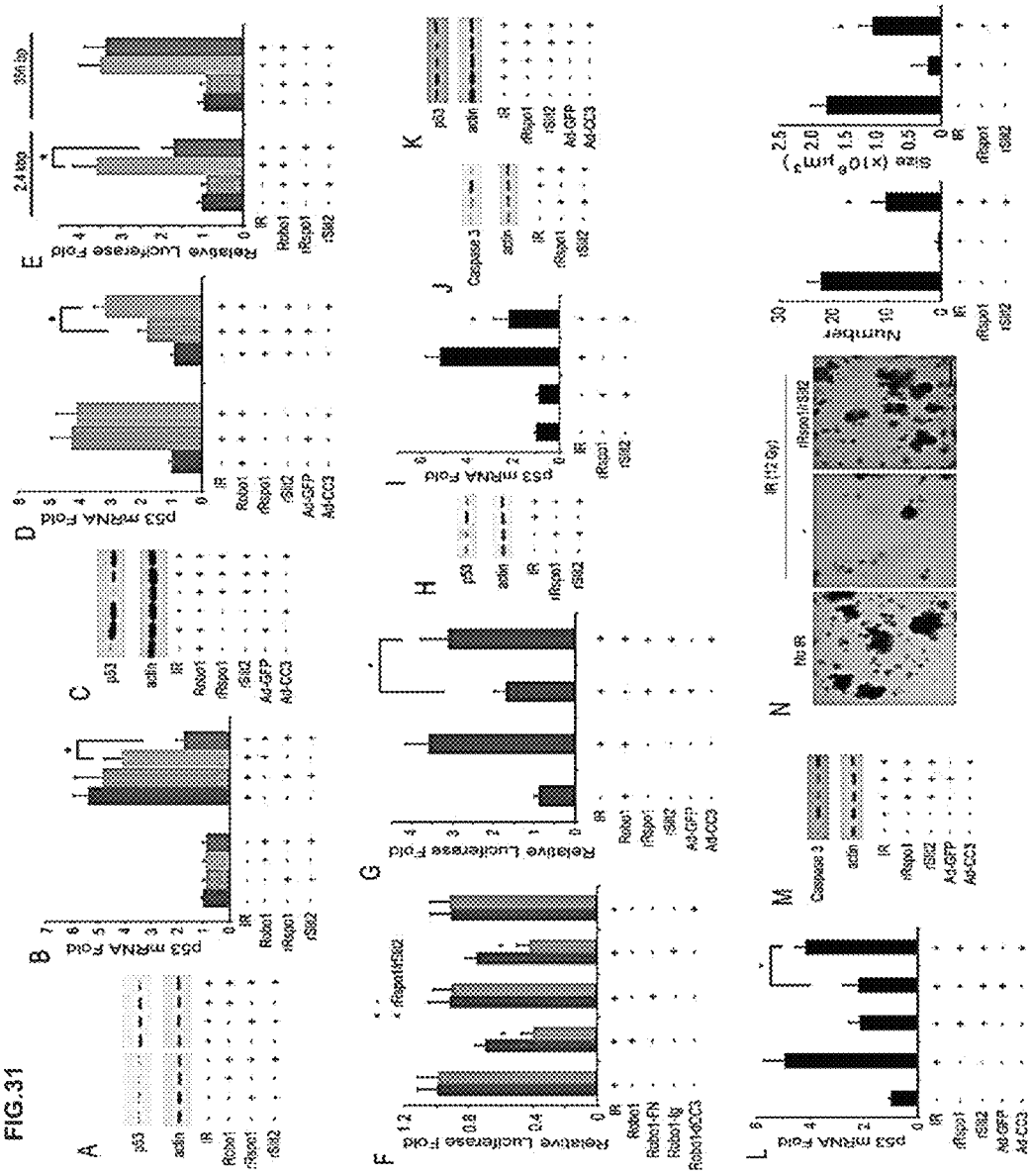
FIG. 31 demonstrates transcriptional regulation of p53 by canonical Wnt activation. (A-D) Treatment with Rspo1/Slit2 inhibits p53 expression in Robo1-expressing 293 cells. 293 cells were transfected with the Robo1 plasmid. Following incubation with rRspo1/rSlit2 and exposure to IR, the expression of p53 protein (A, C) and mRNA (B, D) was determined, in the absence (A, B) or presence of Ad-GFP and Ad-CC3 (A, D). (E-G) Effects of Rspo1/Slit2 on the p53 promoter activity. 293 cells were co-transfected with the plasmids of p53 promoter luciferase reporter (2.4 kb or 356 bp), β-gal, Robo1 (E-G), Robo1-FN, Robo1-Ig or Robo1-dCC3 (F). Following incubation with rRspo1/rSlit2 and exposure to IR, the luciferase activities of p53 promoters were determined and normalized against β-gal for expression efficiency, in the absence (E, F) or presence of Ad-GFP and Ad-CC3 (G). (H-M) Rspo1/Slit2 suppresses p53 and active caspase 3 expression in Lgr5$^{high}$ ISCs. The intestinal crypts were isolated from Lgr5-GFP mice and Lgr5$^{high}$ ISCs were sorted by flow cytometry. They received 12 Gy IR in the presence or absence of added rRspo1/rSlit2 (H-J) and Ad-GFP or Ad-CC3 (K-M). Notably, the standard stem cell culture medium contains 0.5 μg/ml rRspo1 without rSlit2 (−), whereas the standard stem cell culture medium contains the final concentrations of 1 μg/ml rRspo1 plus 1 μg/ml rSlit2 (rRspo1+ plus rSlit2+). The expression of p53 protein and mRNA and active caspase 3 was determined. (N)

Additionally, experiments conducted during the course of developing embodiments for the present invention demonstrated that (1) Robo1 acts as a cognate receptor for both Rspo1 and Slit2 (FIG. 24A; see FIG. 29); (2) Rspo1 and Slit2 binding to Robo1 induces formation of Robo1-Lrp6-Lgr5 complex for activation of Wnt/β-catenin signaling (FIG. 24A; see FIG. 30); (3) Wnt/β-catenin activation elicited by Rspo1 and Slit2 transcriptionally represses p53 expression and consequently inhibits p53-mediated ISC apoptosis (FIG. 24A; see FIG. 31); (4) Slit-Robo signaling not only induces ISC proliferation (Zhou et al., 2013 Nature 501, 107-111), but also reduces p53-mediated ISC apoptosis (see FIGS. 25-28); cumulating in accelerated repair of acute gut injury (FIG. 24C).

Accordingly, in certain embodiments, the present invention provides compositions and methods for inducing ISC homeogenesis and/or regeneration. The present invention is not limited to a particular manner of inducing ISC homeogenesis and/or regeneration.

In some embodiments, induction of ISC homeogenesis and/or regeneration is accomplished within the small intestine. In some embodiments, induction of ISC homeogenesis and/or regeneration is accomplished within the epithelium of the small intestine. In some embodiments, induction of ISC homeogenesis and/or regeneration is accomplished within the crypt region of the small intestine. In some embodiments, induction of ISC homeogenesis and/or regeneration is accomplished within the villus region of the small intestine.

In some embodiments, induction of ISC homeogenesis and/or regeneration is accomplished through binding of Rspo1 with Robo1 and Slit2 with Robo1. In some embodiments, binding of Rspo1 with Robo1 and Slit2 with Robo1 results in binding of Robo1 with LRP6. In some embodiments, binding of Rspo1 with Robo1 and Slit2 with Robo1 results in binding of Robo1 with LRP6 at the CC3 motif of Robo1. In some embodiments, binding of Robo1 with LRP6 results in phosphorylation of LRP6. In some embodiments, binding of Rspo1 with Robo1 and Slit2 with Robo1 results in association of Robo1 with LRG5. In some embodiments, binding of Rspo1 with Robo1 and Slit2 with Robo1 results in β-catenin translocation. In some embodiments, binding of Rspo1 with Robo1 and Slit2 with Robo1 results in activation of canonical Wnt signaling. In some embodiments, binding of Rspo1 and Slit2 to Robo1 induces formation of Robo1-Lrp6-Lgr5 complex for activation of Wnt/β-catenin signaling. In some embodiments, such activation of Wnt/β-catenin signaling transcriptionally represses p53 expression and consequently inhibits p53-mediated ISC apoptosis.

In certain embodiments, the present invention provides methods for treating a subject having a disorder (e.g., cancer) (e.g., colon cancer), comprising administering to the subject a medical procedure involving radiation, and further administering during the course of the medical procedure a composition comprising a Rspo1 agent and a Slit2 agent. In some embodiments, the administration of the composition treats and/or prevents intestinal tissue damage resulting from the medical procedure, wherein the intestinal tissue comprises Robo1 expression. In some embodiments, the Rspo1 agent is capable of binding the location on Robo1 where endogenous Rspo1 binds Robo1. In some embodiments, the Slit2 agent is capable of binding the location on Robo1 where endogenous Slit2 binds Robo1. In some embodiments, the subject is a human being (e.g., a human being undergoing radiation treatment). In some embodiments, the disorder is cancer. In some embodiments, the administering is a short-pulse administration (e.g., a three day short-pulse administration of a Rspo1 agent and a Slit2 agent).

In some embodiments, the administering of the composition results in induction of intestinal stem cell homeogenesis and/or regeneration. The methods are not limited to a particular manner of inducing intestinal stem cell homeogenesis and/or regeneration. In some embodiments, administering of the composition comprising a Rspo1 agent and a Slit2 agent results in binding of the Rspo1 agent with Robo1 and binding of the Slit2 agent with Robo1 within the intestinal tissue. In some embodiments, the binding of the Rspo1 agent with Robo1 and the binding of the Slit2 agent with Robo1 results in binding of Robo1 with LRP6. In some embodiments, the binding of Robo1 with LRP6 occurs at the CC3 motif within Robo1. In some embodiments, the binding of Robo1 with LRP6 results in phosphorylation of the LRP6. In some embodiments, the binding of the Rspo1 agent with Robo1 and the binding of the Slit2 agent with Robo1 results in association of Robo1 with LRG5. In some embodiments, the binding of the Rspo1 agent with Robo1 and the binding of the Slit2 agent with Robo1 results in β-catenin translocation. In some embodiments, the binding of the Rspo1 agent with Robo1 and the binding of the Slit2 agent with Robo1 results in activation of canonical Wnt signaling within the intestinal tissue. In some embodiments, binding of Rspo1 and Slit2 to Robo1 induces formation of Robo1-Lrp6-Lgr5 complex for activation of Wnt/β-catenin signaling. In some embodiments, such activation of Wnt/β-catenin signaling transcriptionally represses p53 expression and consequently inhibits p53-mediated ISC apoptosis.

The methods are not limited to a particular type of intestinal tissue. In some embodiments, the intestinal tissue is small intestinal tissue. In some embodiments, the intestinal tissue is the crypt region of the small intestine.

The methods are not limited to a particular type of medical procedure involving radiation. In some embodiments, the medical procedure involving radiation is selected from the group consisting of photon radiotherapy, particle beam radiation therapy, brachytherapy, interstitial irradiation, intracavity irradiation, radioimmunotherapy, and ionizing (electromagnetic) radiotherapy.

The methods are not limited to particular types of Rspo1 agents and/or Slit2 agents. In some embodiments, Rspo1 agent is recombinant Rspo1 (see, e.g., Zhou, W. J., 2013 Nature 501: 107-111). In some embodiments, the Slit2 agent is recombinant Slit2 (see, e.g., Zhou, W. J., et al., 2011 Cell Res. 21, 609-626).

II. Exemplary Agents

The present invention is not limited to a particular of facilitating binding of Rspo1 with Robo1 and Slit2 with Robo1. In certain embodiments, the present invention provides a Rspo1 agent capable of binding the location on Robo1 where endogenous Rspo1 binds Robo1. In certain embodiments, the present invention provides a Slit2 agent capable of binding the location on Robo1 where endogenous Slit2 binds Robo1. In some embodiments, binding of a Rspo1 agent with Robo1 and a Slit2 agent with Robo1 results in induction of ISC homeogenesis and/or regeneration.

The present invention is not limited to a particular type and/or kind of a Rspo1 agent. In some embodiments, the Rspo1 agent is recombinant Rspo1 capable of binding capable of binding the location on Robo1 where endogenous Rspo1 binds Robo1. In some embodiments, Rspo1 agent is recombinant Rspo1 as described in Zhou, W. J., 2013 Nature 501: 107-111. In some embodiments, the Rspo1 agent is a peptide capable of binding capable of binding the location on Robo1 where endogenous Rspo1 binds Robo1. In some embodiments, the Rspo1 agent is a small molecule capable of binding the location on Robo1 where endogenous Rspo1 binds Robo1. In some embodiments, the Rspo1 agent is a peptidomimetic capable of binding the location on Robo1 where endogenous Rspo1 binds Robo1. In some embodiments, the Rspo1 agent is a cyclic peptide capable of binding the location on Robo1 where endogenous Rspo1 binds Robo1.

The present invention is not limited to a particular type and/or kind of a Slit2 agent. In some embodiments, the Slit2 agent is recombinant Slit2 capable of binding capable of binding the location on Robo1 where endogenous Slit2 binds Robo1. In some embodiments, the Slit2 agent is recombinant Slit2 as described in Zhou, W. J., et al., 2011 Cell Res. 21, 609-626). In some embodiments, the Slit2 agent is a peptide capable of binding capable of binding the location on Robo1 where endogenous Slit2 binds Robo1. In some embodiments, the Slit2 agent is a small molecule capable of binding the location on Robo1 where endogenous Slit2 binds Robo1. In some embodiments, the Slit2 agent is a peptidomimetic capable of binding the location on Robo1 where endogenous Slit2 binds Robo1. In some embodiments, the Slit2 agent is a cyclic peptide capable of binding the location on Robo1 where endogenous Slit2 binds Robo1.

In some embodiments, the present invention provides compositions comprising a Rspo1 agent and a Slit2 agent. In some embodiments, the present invention provides comprising a Rspo1 agent. In some embodiments, the present invention provides comprising a Slit2 agent.

III. Therapeutic Application

Cancer research has been righteously and successfully focused on prevention, early detection and identification of specific molecular targets that causally distinguish the malignant cells from the neighboring benign cells (see, e.g., Hanahan and Weinberg, 2011 Cell 144, 646-674). However, a major clinical challenge concerns whether a way to drastically reduce devastating and sometimes lethal tissue injury caused by intensive chemoradiotherapy during treatment of late-staged metastatic cancers can be found. In addition, exposure to lethal doses of ionizing radiation, such as the Chernobyl and Fukushima accidents, destroys the hematopoietic, gastrointestinal, central nervous and cardiovascular systems. For instance, identification of novel therapeutics that enable the survival and function of tissue-specific stem cells during chemoradiotherapy could greatly increase the range of treatment options, while decreasing catastrophic tissue and organ damage that leads to ultimate death of cancer patients. While granulocyte colony-stimulating factor (G-CSF) and other growth factors may stimulate the bone marrow for hematopoietic recovery (see, e.g., Wadhwa and Thorpe, 2008 Thromb. Haemost. 99, 863-873), a pending challenge is how to therapeutically protect the gastrointestinal tract from the chemoradiation-induced damage. In this context, Rspo1 has been demonstrated to alleviate intestinal injury, oral mucositis and GVHD induced by chemoradiotherapy (see, e.g., Kim et al., 2005 Science 309, 1256-1259; Zhao et al., 2009 Proc. Natl. Acad. Sci. USA 106, 2331-2336; Bhanja et al., 2009 PLoS One 4, e8014; Takashima et al., 2011 J. Exp. Med. 208, 285-294). Experiments conducted during the course of developing embodiments for the present invention discovered that Slit2 acts cooperatively with Rspo1 for reducing loss of ISCs and alleviating chemoradiation-induced gut injury, leading to significant prolongation of the overall survival even in animals receiving the lethal doses of 5-FU and whole body/abdominal irradiation. Moreover, it was shown that upon lethal dosages of chemoradiation, administering a short pulse of Rspo1 plus Slit2 reduced ISC loss, mitigated intestinal impairment and protected animals from death, without concomitantly decreasing the sensitivity of intestinal cancer to chemotherapy. As such, by optimal induction of ISCs, Rspo1 and Slit2 serve as therapeutic adjuvants to increase host tolerance to chemoradiotherapy.

Accordingly, in certain embodiments, the present invention provides methods (e.g., therapeutic applications) for treating and/or preventing disorders and/or conditions related to an intestinal stem cell (ISC) damaging event. In some embodiments, the methods involve administering a Rspo1 agent and a Slit2 agent (see, e.g., Section II— Exemplary Agents) of the present invention to a subject experiencing or at risk for experiencing an ISC damaging event. In some embodiments, administration of such agents (e.g., a Rspo1 agent and a Slit2 agent) results in induction of ISC homeogenesis and/or regeneration. In some embodiments, induction of ISC homeogenesis and/or regeneration results in protection from and/or treatment for an ISC damaging event.

The present invention is not limited to treating and/or preventing disorders and/or conditions related to an intestinal stem cell (ISC) damaging event in a particular type of subject. In some embodiments, the subject is a mammal. In some embodiments, the subject is a human being. In some embodiments, the human being is a cancer patient undergoing radiation therapy. In some embodiments, the human being is undergoing a procedure involving exposure to radiation.

The present invention is not limited to particular manner of inducing ISC homeogenesis and/or regeneration resulting in protection from and/or treatment for an ISC damaging event. In some embodiments, ISC homeogenesis and/or regeneration is accomplished through binding of the Rspo1 agent with Robo1 and binding of the Slit2 agent with Robo1. In some embodiments, binding of the Rspo1 agent with Robo1 and binding of the Slit2 agent with Robo1 results in binding of Robo1 with LRP6. In some embodiments, binding of Rspo1 with Robo1 and Slit2 with Robo1 results in binding of Robo1 with LRP6 at the CC3 motif of Robo1. In some embodiments, binding of Robo1 with LRP6 results in phosphorylation of LRP6. In some embodiments, binding of the Rspo1 agent with Robo1 and binding of the Slit2 agent with Robo1 results in association of Robo1 with LRG5. In some embodiments, binding of the Rspo1 agent with Robo1 and binding of the Slit2 agent with Robo1 results in β-catenin translocation. In some embodiments, binding of the Rspo1 agent with Robo1 and binding of the Slit2 agent results in activation of canonical Wnt signaling. In some embodiments, binding of Rspo1 and Slit2 to Robo1 induces formation of Robo1-Lrp6-Lgr5 complex for activation of Wnt/β-catenin signaling. In some embodiments, such activation of Wnt/β-catenin signaling transcriptionally represses p53 expression and consequently inhibits p53-mediated ISC apoptosis.

The present invention is not limited to inducing ISC homeogenesis and/or regeneration resulting in protection from and/or treatment for an ISC damaging event within a particular tissue region. In some embodiments, induction of ISC homeogenesis and/or regeneration is accomplished within the small intestine. In some embodiments, induction of ISC homeogenesis and/or regeneration is accomplished within the epithelium of the small intestine. In some embodiments, induction of ISC homeogenesis and/or regeneration is accomplished within the crypt region of the small intestine. In some embodiments, induction of ISC homeogenesis and/or regeneration is accomplished within the villus region of the small intestine.

The present invention is not limited to a particular type of ISC damaging event. In some embodiments, the ISC damaging event comprises an exposure to radiation. In some embodiments, the exposure to radiation is an intentional exposure to radiation. In some embodiments, the exposure is an unintentional exposure to radiation (e.g., exposure to radiation through, for example, a terrorism event) (e.g., exposure to radiation resulting from a catastrophic event (e.g., a nuclear facility meltdown) (e.g., accidental overexposure to radiation during a medical procedure)).

In some embodiments, the exposure to radiation occurs through a medical procedure such as, for example, radiation therapy. The methods provided herein are not limited by the types, amounts, or delivery and administration systems used to deliver a therapeutic dose of radiation to a subject. For example, the subject may receive photon radiotherapy, particle beam radiation therapy, other types of radiotherapies, and combinations thereof. In some embodiments, the radiation is delivered to the subject using a linear accelerator. In still other embodiments, the radiation is delivered using a gamma knife.

There is no limitation as to the source of the radiation. The source of radiation can be external or internal to the subject. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

Types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581). The effects of radiation can be at least partially controlled by the clinician. In one embodiment, the dose of radiation is fractionated for maximal target cell exposure and reduced toxicity.

In some embodiments, compositions comprising a Rspo1 agent and a Slit2 agent are administered concurrently with a radiation treatment. For example, in some embodiments, a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). In some embodiments, radiation can be administered 1 day/week, 2 days/week, 3 days/week, 4 days/week, 5 days/week, 6 days/week, or all 7 days/week, depending on the animal's responsiveness and any potential side effects. In some embodiments, the administering is a short-pulse administration (e.g., a three day short-pulse administration of a Rspo1 agent and a Slit2 agent).

Accordingly, in certain embodiments, the present invention provides methods for treating and/or preventing intestinal tissue damage resulting from exposure to an intestinal stem cell damaging event. The present invention is not limited to particular methods for treating and/or preventing intestinal tissue damage resulting from exposure to an intestinal stem cell damaging event. In some embodiments, the methods comprise administering to a subject a composition comprising a Rspo1 agent and a Slit2 agent, wherein the intestinal tissue comprises Robo1 expression. In some embodiments, the Rspo1 agent is capable of binding the location on Robo1 where endogenous Rspo1 binds Robo1. In some embodiments, the Slit2 agent is capable of binding the location on Robo1 where endogenous Slit2 binds Robo1. In some embodiments, the administering of the composition results in induction of intestinal stem cell homeogenesis and/or regeneration. In some embodiments, the subject is a human being. In some embodiments, the human being is undergoing cancer undergoing radiation treatment.

In some embodiments, the composition comprising a Rspo1 agent and a Slit2 agent is administered concurrently with exposure to the intestinal stem cell damaging event. In some embodiments, the composition comprising a Rspo1 agent and a Slit2 agent is administered prior to exposure to the intestinal stem cell damaging event. In some embodiments, the composition comprising a Rspo1 agent and a Slit2 agent is administered after exposure to the intestinal stem cell damaging event. In some embodiments, the composition comprising a Rspo1 agent and a Slit2 agent is administered prior to, concurrently with, and/or after exposure to the intestinal stem cell damaging event.

The methods are not limited to a particular manner of treating and/or preventing intestinal tissue damage resulting from exposure to an intestinal stem cell damaging event. In some embodiments, the administering of the composition comprising a Rspo1 agent and a Slit2 agent results in binding of the Rspo1 agent with Robo1 and binding of the Slit2 agent with Robo1 within the intestinal tissue. In some embodiments, the binding of the Rspo1 agent with Robo1 and the binding of the Slit2 agent with Robo1 results in binding of Robo1 with LRP6. In some embodiments, the binding of Robo1 with LRP6 occurs at the CC3 motif within Robo1. In some embodiments, the binding of Robo1 with LRP6 results in phosphorylation of the LRP6. In some embodiments, the binding of the Rspo1 agent with Robo1 and the binding of the Slit2 agent with Robo1 results in association of Robo1 with LRG5. In some embodiments, the binding of the Rspo1 agent with Robo1 and the binding of the Slit2 agent with Robo1 results in $\beta$-catenin translocation. In some embodiments, the binding of the Rspo1 agent with Robo1 and the binding of the Slit2 agent with Robo1 results in activation of canonical Wnt signaling within the intestinal tissue. In some embodiments, binding of Rspo1 and Slit2 to Robo1 induces formation of Robo1-Lrp6-Lgr5 complex for activation of Wnt/$\beta$-catenin signaling. In some embodiments, such activation of Wnt/$\beta$-catenin signaling transcriptionally represses p53 expression and consequently inhibits p53-mediated ISC apoptosis.

The methods are not limited to a particular type of intestinal tissue. In some embodiments, the intestinal tissue is small intestinal tissue. In some embodiments, the intestinal tissue is the crypt region of the small intestine.

The methods are not limited to a particular type of intestinal stem cell damaging event. In some embodiments, the intestinal stem cell damaging event is an exposure to radiation. In some embodiments, the radiation is medical procedure related radiation. In some embodiments, medical procedure related radiation is selected from the group consisting of photon radiotherapy, particle beam radiation therapy, brachytherapy, interstitial irradiation, intracavity irradiation, radioimmunotherapy, and ionizing (electromagnetic) radiotherapy.

The methods are not limited to particular types of Rspo1 agents and/or Slit2 agents. In some embodiments, the Rspo1 agent is recombinant Rspo1 (see, e.g., Zhou, W. J., 2013 Nature 501: 107-111). In some embodiments, the Rspo1 agent is rRspo1-Fc (see, FIG. 32). In some embodiments, the recombinant Rspo1 agent is any type, kind or variant of a commercially available and/or empirically developed recombinant Rspo1. In some embodiments, the Slit2 agent is recombinant Slit2 (see, e.g., Zhou, W. J., et al., 2011 Cell Res. 21, 609-626). In some embodiments, the recombinant Slit2 agent is any type, kind or variant of a commercially available and/or empirically developed recombinant Slit2. In some embodiments, the Slit2 agent is rSlit2-Fc (see, FIG. 32).

In certain embodiments, the present invention provides methods for inducing intestinal stem cell homeogenesis and/or regeneration within an intestinal tissue sample, comprising exposing to the intestinal tissue sample a composition comprising a Rspo1 agent and a Slit2 agent, wherein the intestinal tissue sample comprises Robo1 expression. In some embodiments, the Rspo1 agent is capable of binding the location on Robo1 where endogenous Rspo1 binds Robo1, and wherein the Slit2 agent is capable of binding the location on Robo1 where endogenous Slit2 binds Robo1.

In some embodiments, the intestinal tissue sample is an in vivo sample. In some embodiments, the intestinal tissue sample is an in vitro sample. In some embodiments, the intestinal tissue sample is within a human subject. In some embodiments, the intestinal tissue sample is an ex vivo sample.

In some embodiments, the exposure of the composition to the intestinal tissue sample results in binding of the Rspo1 agent with Robo1, and binding of the Slit2 agent with Robo1. In some embodiments, the binding of the Rspo1 agent with Robo1, and binding of the Slit2 agent with Robo1 results in induction of intestinal stem cell homeogenesis and/or regeneration. In some embodiments, the binding of the Rspo1 agent with Robo1 and the binding of the Slit2 agent with Robo1 results in binding of Robo1 with LRP6. In some embodiments, the binding of Robo1 with LRP6 occurs at the CC3 motif within Robo1. In some embodiments, the binding of Robo1 with LRP6 results in phosphorylation of the LRP6. In some embodiments, the binding of the Rspo1 agent with Robo1 and the binding of the Slit2 agent with Robo1 results in association of Robo1 with LRG5. In some embodiments, he binding of the Rspo1 agent with Robo1 and the binding of the Slit2 agent with Robo1 results in $\beta$-catenin translocation. In some embodiments, the binding of the Rspo1 agent with Robo1 and the binding of the Slit2 agent with Robo1 results in activation of canonical Wnt signaling within the intestinal tissue. In some embodiments, binding of Rspo1 and Slit2 to Robo1 induces formation of Robo1-Lrp6-Lgr5 complex for activation of Wnt/$\beta$-catenin signaling. In some embodiments, such activation of Wnt/$\beta$-catenin signaling transcriptionally represses p53 expression and consequently inhibits p53-mediated ISC apoptosis.

The methods are not limited to a particular type of intestinal tissue within the intestinal tissue sample. In some embodiments, the intestinal tissue sample comprises small intestinal tissue. In some embodiments, the intestinal tissue sample comprises the crypt region of the small intestine.

The methods are not limited to particular types of Rspo1 agents and/or Slit2 agents. In some embodiments, the Rspo1 agent is recombinant Rspo1 (see, e.g., Zhou, W. J., 2013 Nature 501: 107-111). In some embodiments, the Rspo1 agent is rRspo1-Fc (see, FIG. 32). In some embodiments, the recombinant Rspo1 agent is any type, kind or variant of a commercially available and/or empirically developed recombinant Rspo1. In some embodiments, the Slit2 agent is recombinant Slit2 (see, e.g., Zhou, W. J., et al., 2011 Cell Res. 21, 609-626). In some embodiments, the recombinant Slit2 agent is any type, kind or variant of a commercially available and/or empirically developed recombinant Slit2. In some embodiments, the Slit2 agent is rSlit2-Fc (see, FIG. 32).

In certain embodiments, activation of Wnt/beta-catenin signaling by Rspo1 and Slit2 protects hemopoietic injury induced by chemoradiation. Canonical Wnt signaling is known to critically maintain hemopoietic stem cells at the niche within bone marrow. However, no Wnt agonists have been used clinically for induction of haemopoiesis. In some embodiments, it is contemplated that upon lethal doses of chemoradiation, treatment of wild-type mice with Rspo1 plus Slit2 increases the numbers of both total cells and hemopoietic stem cells in the bone marrows. In addition, it is contemplated that treatment of wild-type mice with Rspo1 plus Slit2 also markedly augments the numbers of total cells, T and B lymphocytes in the spleens. In addition, it is contemplated that treatment of wild-type mice with Rspo1 plus Slit2 potently raises the numbers of myeloid cells, T and B lymphocytes and platelets in the peripheral blood. Accordingly, the present invention provides methods involving activation of Wnt/beta-catenin signaling by Rspo1 and Slit2 so as to protect hemopoietic injury induced by chemoradiation.

IV. Pharmaceutical Compositions, Formulations, and Exemplary Administration Routes and Dosing Considerations Exemplary embodiments of various contemplated medicaments and pharmaceutical compositions are provided below.

A. Preparing Medicaments

It is contemplated that the agents of the present invention (e.g., Rspo1 agents capable of binding the location on Robo1 where endogenous Rspo1 binds Robo1 and Slit2 agents capable of binding the location on Robo1 where endogenous Slit2 binds Robo1; thereby inducing ISC homeostasis and/or regeneration) are useful in the preparation of medicaments to treat a variety of conditions associated with an ISC damaging event (e.g., medical radiation therapy).

In addition, it is contemplated that the agents are also useful for preparing medicaments for treating other disorders wherein the effectiveness of the agents are known or predicted. The methods and techniques for preparing medicaments of an agent of the present invention (e.g., Rspo1 agents capable of binding the location on Robo1 where endogenous Rspo1 binds Robo1 and Slit2 agents capable of binding the location on Robo1 where endogenous Slit2 binds Robo1; thereby inducing ISC homeostasis and/or regeneration) are well-known in the art. Exemplary pharmaceutical formulations and routes of delivery are described below.

One of skill in the art will appreciate that any one or more of the agents described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions (e.g., comprising Rspo1 agents capable of binding the location on Robo1 where endogenous Rspo1 binds Robo1 and Slit2 agents capable of binding the location on Robo1 where endogenous Slit2 binds Robo1; thereby inducing ISC homeostasis and/or regeneration) are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoleic acid), extenders, and stabilizers, etc.

In some embodiments, the agents of the present invention are provided in unsolvated form or are in non-aqueous solutions (e.g., ethanol). The agents may be generated to allow such formulations through the production of specific crystalline polymorphs compatible with the formulations.

In certain embodiments, the present invention provides instructions for administering an agent to a subject. In certain embodiments, the present invention provides instructions for using the compositions contained in a kit for the treatment of conditions characterized by the dysregulation of apoptotic processes in a cell or tissue (e.g., providing dosing, route of administration, decision trees for treating physicians for correlating patient-specific characteristics with therapeutic courses of action). In certain embodiments, the present invention provides instructions for using the compositions contained in the kit to treat a variety of disorders associated an ISC damaging event.

C. Exemplary Administration Routes and Dosing Considerations

Various delivery systems are known and can be used to administer therapeutic agents (e.g., exemplary agents as described in Section II above) of the present invention (e.g., Rspo1 agents capable of binding the location on Robo1 where endogenous Rspo1 binds Robo1 and Slit2 agents capable of binding the location on Robo1 where endogenous Slit2 binds Robo1; thereby inducing ISC homeostasis and/or regeneration), e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the agents identified can be administered to subjects or individuals susceptible to or at risk of developing a variety of conditions associated with an ISC damaging event. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent, the effective amount may be more or less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the agents described herein (e.g., Rspo1 agents capable of binding the location on Robo1 where endogenous Rspo1 binds Robo1 and Slit2 agents capable of binding the location on Robo1 where endogenous Slit2 binds Robo1; thereby inducing ISC homeostasis and/or regeneration) with one or more additional active agents. Indeed, it is a further aspect of this invention to provide methods for enhancing prior art therapies and/or pharmaceutical compositions by co-administering the agents of this invention. In co-administration procedures, the agents may be administered concurrently or sequentially. In one embodiment, the agents described herein are administered prior to the other active agent(s). The pharmaceutical formulations and modes of administration may be any of those described above. In addition, the two or more co-administered chemical agents, biological agents or radiation may each be administered using different modes or different formulations.

In some embodiments, compositions comprising a Rspo1 agent and a Slit2 agent may be co-administered with radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like). Radiosensitizers enhance the killing of tumor cells.

In some embodiments, comprising a Rspo1 agent and a Slit2 agent may be co-administered with additional types of radioprotectors (e.g., cysteamine, aminoalkyl dihydrogen phosphorothioates, amifostine (WR 2721), IL-1, IL-6, and the like). Radioprotectors protect healthy tissue from the harmful effects of radiation.

The agent or agents to be co-administered depends on the type of condition being treated. For example, when the condition being treated is associated an ISC damaging event (e.g., chemoradiation medical therapy) resulting from the treatment of a type of cancer, the additional agent is known to treat such cancer. A number of suitable therapeutic or anticancer agents are contemplated for use in the methods provided herein. Indeed, the methods provided herein can include but are not limited to, administration of numerous therapeutic agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of therapeutic agents such as chemotherapeutic compounds and anticancer therapies suitable for co-administration with the agents described herein (e.g., Rspo1 agents capable of binding the location on Robo1 where endogenous Rspo1 binds Robo1 and Slit2 agents capable of binding the location on Robo1 where endogenous Slit2 binds Robo1; thereby inducing ISC homeostasis and/or regeneration) are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods provided herein include one or more agents provided herein and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | |
|---|---|
| Aldesleukin | Proleukin |
| (des-alanyl-1, serine-125 human interleukin-2) | |
| Alemtuzumab | Campath |
| (IgG1κ anti CD52 antibody) | |
| Alitretinoin | Panretin |
| (9-cis-retinoic acid) | |

TABLE 1-continued

| | |
|---|---|
| Allopurinol<br>(1,5-dihydro-4 H-pyrazolo[3,4-d]pyrimidin-4-one monosodium salt) | Zyloprim |
| Altretamine<br>(N,N,N',N',N'',N''-hexamethyl-1,3,5-triazine-2,4,6-triamine) | Hexalen |
| Amifostine<br>(ethanethiol, 2-[(3-aminopropyl)amino]-, dihydrogen phosphate (ester)) | Ethyol |
| Anastrozole<br>(1,3-Benzenediacetonitrile, a,a,a',a'-tetramethyl-5-(1H-1,2,4-triazol-1-ylmethyl)) | Arimidex |
| Arsenic trioxide | Trisenox |
| Asparaginase<br>(L-asparagine amidohydrolase, type EC-2) | Elspar |
| BCG Live<br>(lyophilized preparation of an attenuated strain of *Mycobacterium bovis* (*Bacillus* Calmette-Gukin [BCG], substrain Montreal) | TICE BCG |
| bexarotene capsules<br>(4-[1-(5,6,7,8-tetrahydro-3,5,5,8,8-pentamethyl-2-napthalenyl) ethenyl] benzoic acid) | Targretin |
| bexarotene gel | Targretin |
| Bleomycin<br>(cytotoxic glycopeptide antibiotics produced by *Streptomyces verticillus*; bleomycin $A_2$ and bleomycin $B_2$) | Blenoxane |
| Capecitabine<br>(5'-deoxy-5-fluoro-N-[(pentyloxy)carbonyl]-cytidine) | Xeloda |
| Carboplatin<br>(platinum, diammine [1,1-cyclobutanedicarboxylato(2-)-0,0']-, (SP-4-2)) | Paraplatin |
| Carmustine<br>(1,3-bis(2-chloroethyl)-1-nitrosourea) | BCNU,<br>BiCNU |
| Carmustine with Polifeprosan 20 Implant | Gliadel Wafer |
| Celecoxib<br>(as 4-[5-(4-methylphenyl)-3-(trifluoromethyl)-1H-pyrazol-1-yl] benzenesulfonamide) | Celebrex |
| Chlorambucil<br>(4-[bis(2chloroethyl)amino]benzenebutanoic acid) | Leukeran |
| Cisplatin<br>($PtCl_2H_6N_2$) | Platinol |
| Cladribine<br>(2-chloro-2'-deoxy-b-D-adenosine) | Leustatin,<br>2-CdA |
| Cyclophosphamide<br>(2-[bis(2-chloroethyl)amino] tetrahydro-2H-13,2-oxazaphosphorine 2-oxide monohydrate) | Cytoxan,<br>Neosar |
| Cytarabine<br>(1-b-D-Arabinofuranosylcytosine, $C_9H_{13}N_3O_5$) | Cytosar-U |
| cytarabine liposomal | DepoCyt |
| Dacarbazine<br>(5-(3,3-dimethyl-1-triazeno)-imidazole-4-carboxamide (DTIC)) | DTIC-Dome |
| Dactinomycin, actinomycin D<br>(actinomycin produced by *Streptomyces parvullus*, $C_{62}H_{86}N_{12}O_{16}$) | Cosmegen |
| Darbepoetin alfa<br>(recombinant peptide) | Aranesp |
| daunorubicin liposomal<br>((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome |
| Daunorubicin HCl, daunomycin<br>((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine |
| Denileukin diftitox<br>(recombinant peptide) | Ontak |
| Dexrazoxane<br>((S)-4,4'-(1-methyl-1,2-ethanediyl)bis-2,6-piperazinedione) | Zinecard |
| Docetaxel<br>((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere |
| Doxorubicin HCl<br>(8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin,<br>Rubex |
| doxorubicin | Adriamycin<br>PFS<br>Intravenous injection |
| doxorubicin liposomal | Doxil |
| dromostanolone propionate<br>(17b-Hydroxy-2a-methyl-5a-androstan-3-one propionate) | Dromostanolone |
| dromostanolone propionate | Masterone injection |
| Elliott's B Solution | Elliott's<br>B Solution |
| Epirubicin<br>((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence |
| Epoetin alfa<br>(recombinant peptide) | Epogen |
| Estramustine<br>(estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt |
| Etoposide phosphate<br>(4'-Demethylepipodophyllotoxin 9-[4,6-O-(R)-ethylidene-(beta)-D-glucopyranoside], 4'-(dihydrogen phosphate)) | Etopophos |
| etoposide, VP-16<br>(4'-demethylepipodophyllotoxin 9-[4,6-0-(R)-ethylidene-(beta)-D-glucopyranoside]) | Vepesid |
| Exemestane<br>(6-methylenandrosta-1,4-diene-3,17-dione) | Aromasin |
| Filgrastim<br>(r-metHuG-CSF) | Neupogen |
| floxuridine (intraarterial)<br>(2'-deoxy-5-fluorouridine) | FUDR |
| Fludarabine<br>(fluorinated nucleotide analog of the antiviral agent vidarabine, 9-b-D-arabinofuranosyladenine (ara-A)) | Fludara |
| Fluorouracil, 5-FU<br>(5-fluoro-2,4(1H,3H)-pyrimidinedione) | Adrucil |
| Fulvestrant<br>(7-alpha-[9-(4,4,5,5,5-penta fluoropentylsulphinyl) nonyl]estra-1,3,5-(10)-triene-3,17-beta-diol) | Faslodex |
| Gemcitabine<br>(2'-deoxy-2',2'-difluorocytidine monohydrochloride (b-isomer)) | Gemzar |
| Gemtuzumab Ozogamicin<br>(anti-CD33 hP67.6) | Mylotarg |
| Goserelin acetate | Zoladex<br>Implant |
| Hydroxyurea | Hydrea |
| Ibritumomab Tiuxetan<br>(immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin |
| Idarubicin<br>(5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin |
| Ifosfamide<br>(3-(2-chloroethyl)-2-[(2-chloroethyl)amino]tetrahydro-2H-1,3,2-oxazaphosphorine 2-oxide) | IFEX |
| Imatinib Mesilate<br>(4-[(4-Methyl-1-piperazinyl)methyl]-N-[4-methyl-3-[[4-(3-pyridinyl)-2-pyrimidinyl]amino]-phenyl]benzamide methanesulfonate) | Gleevec |
| Interferon alfa-2a<br>(recombinant peptide) | Roferon-A |

TABLE 1-continued

| | |
|---|---|
| Interferon alfa-2b (recombinant peptide) | Intron A (Lyophilized Betaseron) |
| Irinotecan HCl ((4S)-4,11-diethyl-4-hydroxy-9-[(4-piperidinopiperidino)carbonyloxy]-1H-pyrano[3',4': 6,7] indolizino[1,2-b] quinoline-3,14(4H, 12H) dione hydrochloride trihydrate) | Camptosar |
| Letrozole (4,4'-(1H-1,2,4-Triazol-1-ylmethylene) dibenzonitrile) | Femara |
| Leucovorin (L-Glutamic acid, N[4[[(2amino-5-formyl-1,4,5,6,7,8-hexahydro4oxo6-pteridinyl)methyl]amino]benzoyl], calcium salt (1:1)) | Wellcovorin, Leucovorin |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol |
| Lomustine (1-(2-chloro-ethyl)-3-cyclohexyl-1-nitrosourea) | CeeNU |
| Meclorethamine, nitrogen mustard (2-chloro-N-(2-chloroethyl)-N-methylethanamine hydrochloride) | Mustargen |
| Megestrol acetate 17α(acetyloxy)-6-methylpregna-4,6-diene-3,20-dione | Megace |
| Melphalan, L-PAM (4-[bis(2-chloroethyl) amino]-L-phenylalanine) | Alkeran |
| Mercaptopurine, 6-MP (1,7-dihydro-6 H-purine-6-thione monohydrate) | Purinethol |
| Mesna (sodium 2-mercaptoethane sulfonate) | Mesnex |
| Methotrexate (N-[4-[[(2,4-diamino-6-pteridinyl)methyl]methylamino]benzoyl]-L-glutamic acid) | Methotrexate |
| Methoxsalen (9-methoxy-7H-furo[3,2-g][1]-benzopyran-7-one) | Uvadex |
| Mitomycin C | Mutamycin |
| mitomycin C | Mitozytrex |
| Mitotane (1,1-dichloro-2-(o-chlorophenyl)-2-(p-chlorophenyl) ethane) | Lysodren |
| Mitoxantrone (1,4-dihydroxy-5,8-bis[[2-[(2-hydroxyethyl)amino]ethyl]amino]-9,10-anthracene-dione dihydrochloride) | Novantrone |
| Nandrolone phenpropionate | Durabolin-50 |
| Nofetumomab | Verluma |
| Oprelvekin (IL-11) | Neumega |
| Oxaliplatin (cis-[(1R,2R)-1,2-cyclohexanediamine-N,N'] [oxalato(2-)-O,O'] platinum) | Eloxatin |
| Paclitaxel (5β,20-Epoxy-1,2a,4,7β,10β,13a-hexahydroxytax-11-en-9-one 4,10-diacetate 2-benzoate 13-ester with (2R,3 S)-N-benzoyl-3-phenylisoserine) | TAXOL |
| Pamidronate (phosphonic acid (3-amino-1-hydroxypropylidene) bis-, disodium salt, pentahydrate, (APD)) | Aredia |
| Pegademase ((monomethoxypolyethylene glycol succinimidyl) 11-17-adenosine deaminase) | Adagen (Pegademase Bovine) |
| Pegaspargase (monomethoxypolyethylene glycol succinimidyl L-asparaginase) | Oncaspar |
| Pegfilgrastim (covalent conjugate of recombinant methionyl human G-CSF (Filgrastim) and monomethoxypolyethylene glycol) | Neulasta |
| Pentostatin | Nipent |
| Pipobroman | Vercyte |
| Plicamycin, Mithramycin (antibiotic produced by Streptomyces plicatus) | Mithracin |
| Porfimer sodium | Photofrin |
| Procarbazine (N-isopropyl-μ-(2-methylhydrazino)-p-toluamide monohydrochloride) | Matulane |
| Quinacrine (6-chloro-9-(1-methyl-4-diethyl-amine) butylamino-2-methoxyacridine) | Atabrine |
| Rasburicase (recombinant peptide) | Elitek |
| Rituximab (recombinant anti-CD20 antibody) | Rituxan |
| Sargramostim (recombinant peptide) | Prokine |
| Streptozocin (streptozocin 2-deoxy-2-[[(methylnitrosoamino)carbonyl]amino]-a(and b)-D-glucopyranose and 220 mg citric acid anhydrous) | Zanosar |
| Talc $(Mg_3Si_4O_{10} (OH)_2)$ | Sclerosol |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex |
| Temozolomide (3,4-dihydro-3-methyl-4-oxoimidazo[5,1-d]-as-tetrazine-8-carboxamide) | Temodar |
| teniposide, VM-26 (4'-demethylepipodophyllotoxin 9-[4,6-0-(R)-2-thenylidene-(beta)-D-glucopyranoside]) | Vumon |
| Testolactone (13-hydroxy-3-oxo-13,17-secoandrosta-1,4-dien-17-oic acid [dgr]-lactone) | Teslac |
| Thioguanine, 6-TG (2-amino-1,7-dihydro-6 H-purine-6-thione) | Thioguanine |
| Thiotepa (Aziridine,1,1',1''-phosphinothioylidynetris-, or Tris (1-aziridinyl) phosphine sulfide) | Thioplex |
| Topotecan HCl ((S)-10-[(dimethylamino) methyl]-4-ethyl-4,9-dihydroxy-1H-pyrano[3',4': 6,7] indolizino [1,2-b] quinoline-3,14-4H,12H)-dione monohydrochloride) | Hycamtin |
| Toremifene (2-(p-[(Z)-4-chloro-1,2-diphenyl-1-butenyl]-phenoxy)-N,N-dimethylethylamine citrate (1:1)) | Fareston |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar |
| Trastuzumab (recombinant monoclonal $IgG_1$ kappa anti-HER2 antibody) | Herceptin |
| Tretinoin, ATRA (all-trans retinoic acid) | Vesanoid |
| Uracil Mustard | Uracil Mustard Capsules |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar |
| Vinblastine, Leurocristine $(C_{46}H_{56}N_4O_{10} \cdot H_2SO_4)$ | Velban |
| Vincristine $(C_{46}H_{56}N_4O_{10} \cdot H_2SO_4)$ | Oncovin |
| Vinorelbine (3',4'-didehydro-4'-deoxy-C'-norvincaleukoblastine [R-(R*,R*)-2,3-dihydroxybutanedioate (1:2)(salt)]) | Navelbine |
| Zoledronate, Zoledronic acid ((1-Hydroxy-2-imidazol-1-yl-phosphonoethyl) phosphonic acid monohydrate) | Zometa |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

V. Drug Screens

In some embodiments of the present invention, potential agents (e.g., peptides, small molecules, peptidomimetics, and/or cyclic peptides) are screened for their binding affinity to bind the location on Robo1 where endogenous Rspo1 binds Robo1. In some embodiments of the present invention, potential agents (e.g., peptides, small molecules, peptidomimetics, and/or cyclic peptides) are screened for their binding affinity to bind the location on Robo1 where endogenous Slit2 binds Robo1. In some embodiments, binding affinity screens are conducted in in vitro systems. In other embodiments, these screens are conducted in in vivo or ex vivo systems.

In some embodiments, potential agents (e.g., peptides, small molecules, peptidomimetics, and/or cyclic peptides) shown to be able to bind the location on Robo1 where endogenous Rspo1 binds Robo1 or be able to bind the location on Robo1 where endogenous Slit2 binds Robo1 are further screened for an ability to induce ISC homeogenesis and/or regeneration.

In some embodiments, structure-based virtual screening methodologies are contemplated for predicting the binding affinity of potential agents (e.g., peptides, small molecules, peptidomimetics, and/or cyclic peptides) with the location on Robo1 where endogenous Rspo1 binds Robo1. In some embodiments, structure-based virtual screening methodologies are contemplated for predicting the binding affinity of potential agents (e.g., peptides, small molecules, peptidomimetics, and/or cyclic peptides) with the location on Robo1 where endogenous Slit2 binds Robo1. In some embodiments, small molecule structures are predicted from a molecular modeling software (e.g., MacroModel, MOE, Glide, Gold, Autodock, DOCK, Unity, Cerius2, Daylight, PipelinePilot, ChemAxon, Sprout, Hook, MCSS, AMBER, BOSS).

EXPERIMENTAL

Example 1

Figure 2:
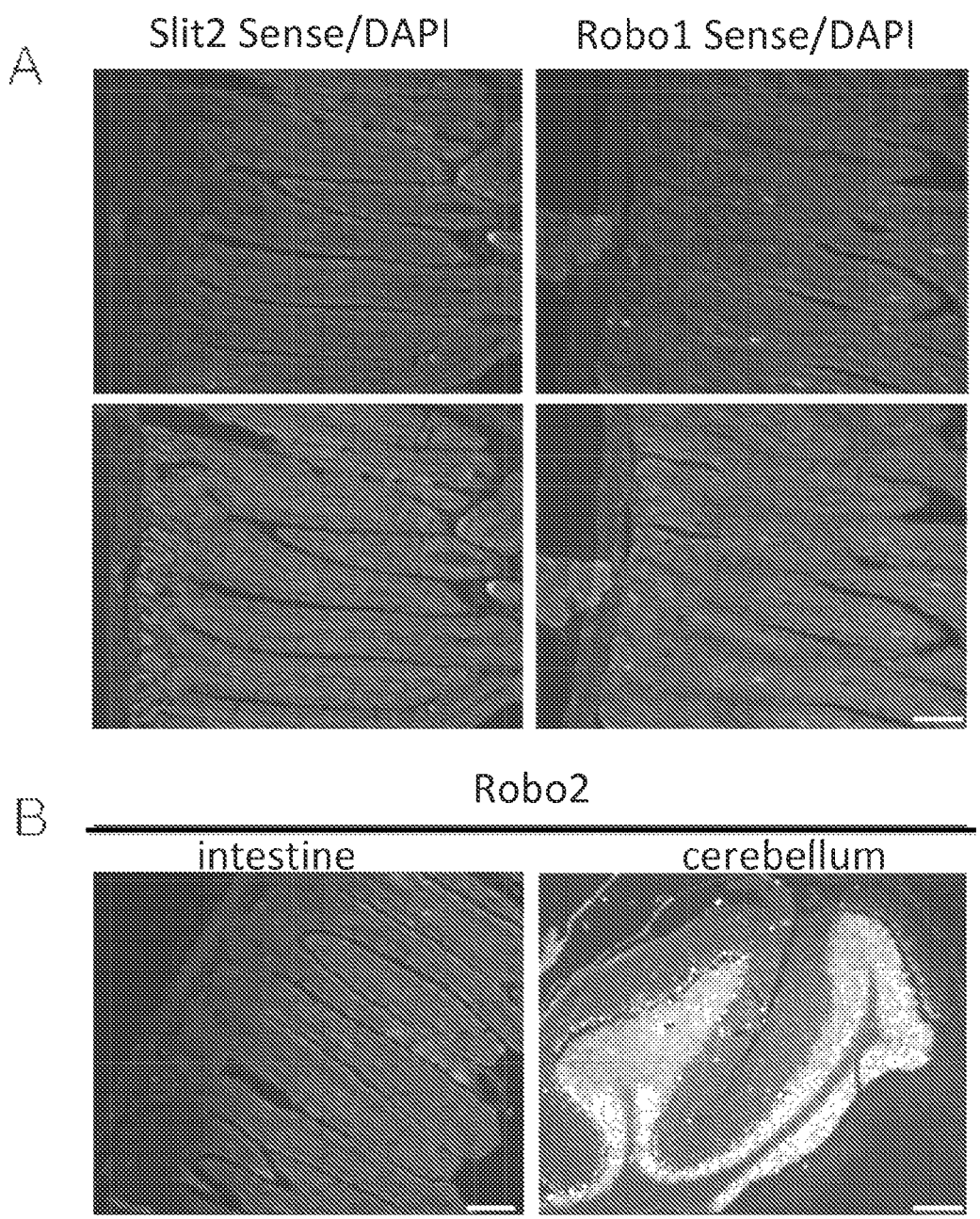
FIG. 2 describes RNA probe specificity and Robo2 mRNA expression. Tissue specimens of the small intestine and cerebellum obtained from Wt mice (8 weeks old) were stained by using the sense Robo1 and Slit2 RNA probes (A) or the Robo2 RNA probe (B). Sections were counterstained with DAPI (A, lower panel). Results are representatives of more than three separate experiments. Bar, 50 μM for A and B (small intestine); 200 μm for B (cerebellum).
Figure 3:
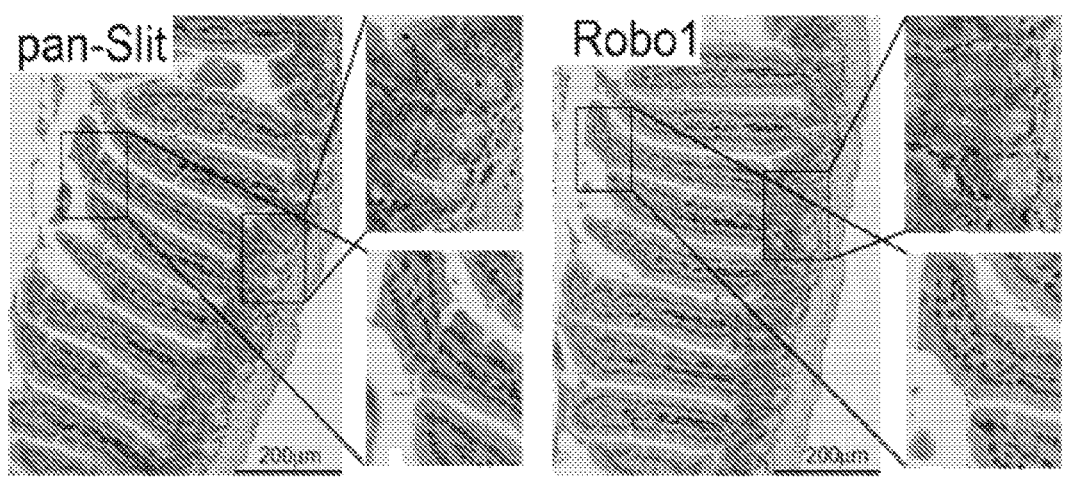
FIG. 3 describes expression of pan-Slit and Robo1 proteins in small intestine. The pan-Slit and Robo1 antigens in the crypts and villi of small intestines from Wt mice (8 weeks old) were immunohistochemically detected by 51 and R4, respectively. Slides were counterstained with hematoxylin & eosin (H&E). Results are representatives of more than three separate experiments. Bars, 200 μm.

This example describes expression of Slit2 and Robo1 on ISCs at the crypt. Two-color fluorescent were used in situ hybridization (FISH) with antisense mRNA probes to visualize Slit2 and Robo1 mRNAs in the small intestines of C57BL/6 (Wt) mice. Surprisingly, Slit2 and Robo1 mRNAs were co-localized and were expressed markedly higher amounts in the crypts than in the villi (FIG. 1A). For specificity control, the Slit2 and Robo1 sense mRNA probes detected only background staining (FIG. 2A). To detect Slit2 and Robo1 proteins, the 51 monoclonal antibody (mAb) were used to detect pan-Slit antigens and the R4 mAb to detect Robo1 antigen (see, e.g., Wang, B., et al. (2003) Cancer Cell 4, 19-29; Zhou, W. J., et al. (2011) Cell Res. 21, 609-626). Both proteins were found at higher concentrations in the crypts than in the villi (FIG. 3). The expression of both Slit2 and Robo1 localized at the crypt of small intestine mirrors the well-characterized gradient of active β-catenin at the crypt-villus axis (see, e.g., Solanas and Batlle (2011) Exp. Cell Research Vol. 317(19):2695-2701).

Figure 4:
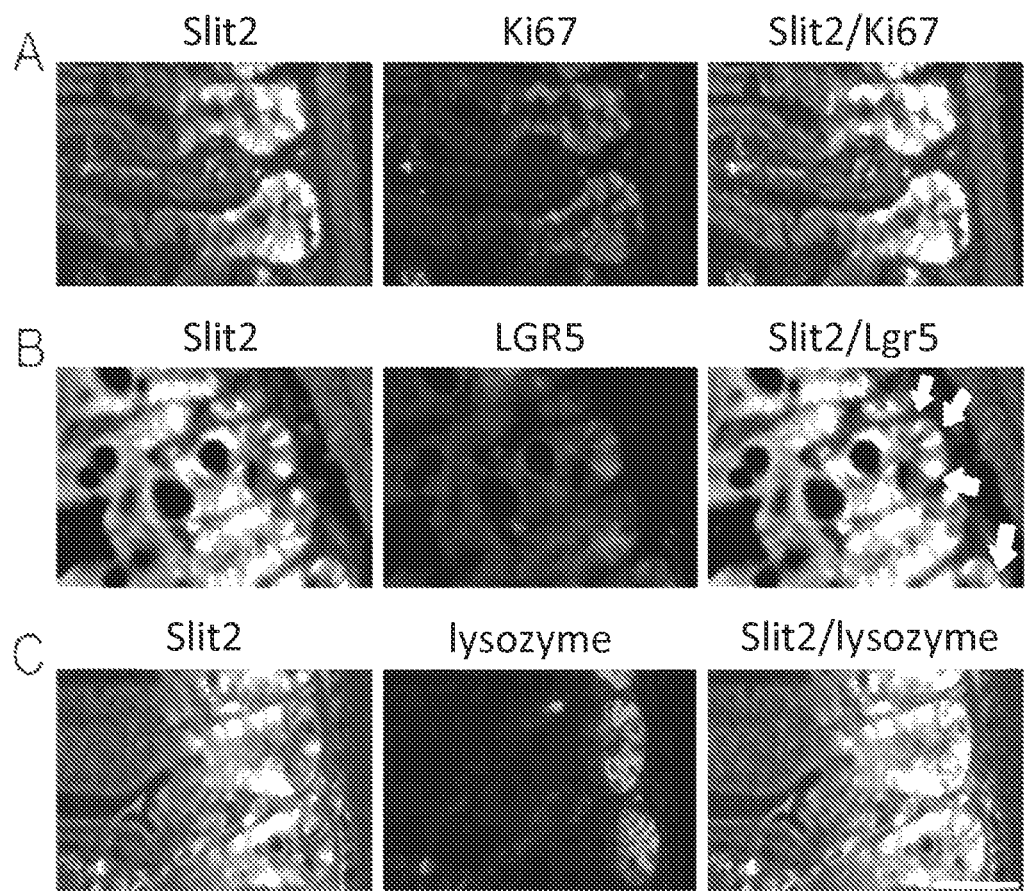
FIG. 4 describes cellular localization of Slit2 mRNA. Tissue sections of the small intestine obtained from Wt mice (8 weeks old) were stained for Slit2 mRNA and proteins of Ki67 (A), LGR5 (B) and lysozyme (C). Immunofluorescent images were observed under a laser scanning confocal microscope, and the recorded fluorescent images were then merged. White arrows indicate LGR5-positive ISCs co-localized with Slit2 mRNA (B). Results are representatives of more than three separate experiments. Bars, 50 μm.
Figure 5:
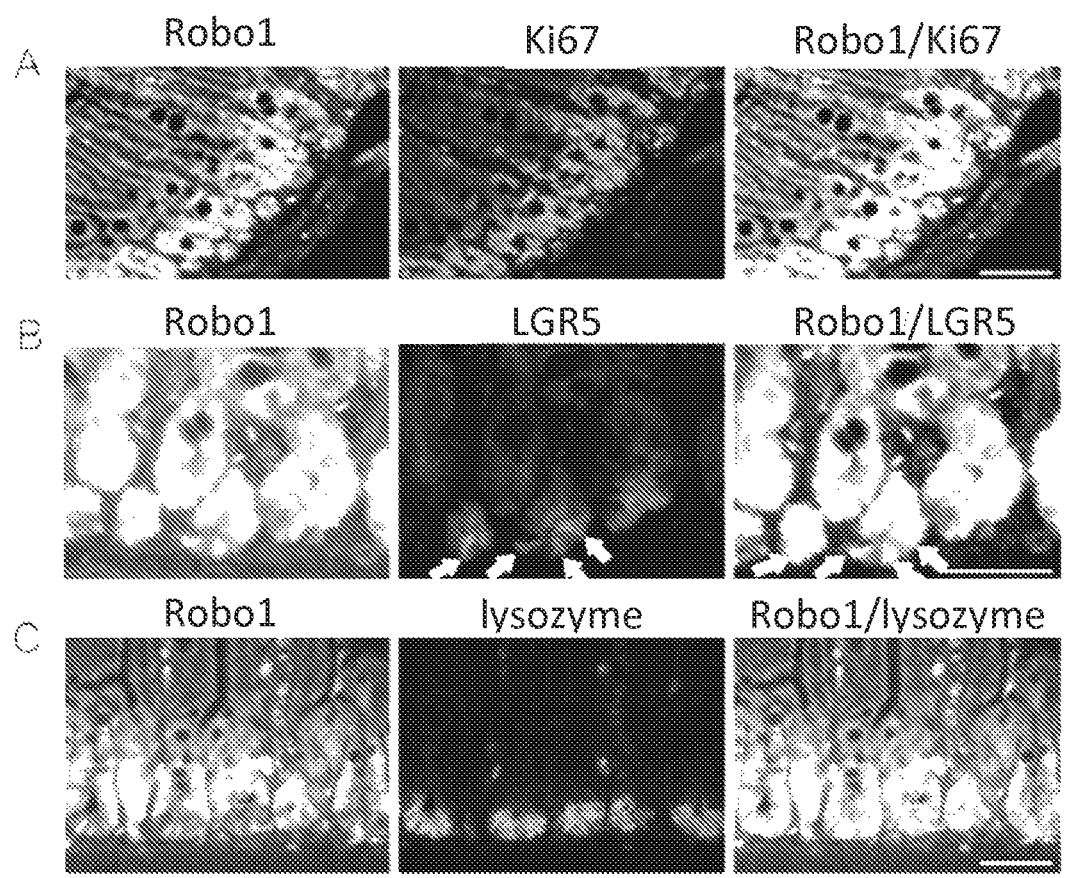
FIG. 5 describes cellular localization of Robo1 mRNA. Tissue sections of the small intestine harvested from Wt mice (8 weeks old) were stained for Robo1 mRNA and proteins of Ki67 (A), LGR5 (B) and lysozyme (C). Immunofluorescent images were observed under a laser scanning confocal microscope, and the recorded fluorescent images were then merged. White arrows indicate LGR5-positive ISCs co-localized with Robo1 mRNA (B). Results are representatives of more than three separate experiments. Bars, 50 μm.
Figure 6:
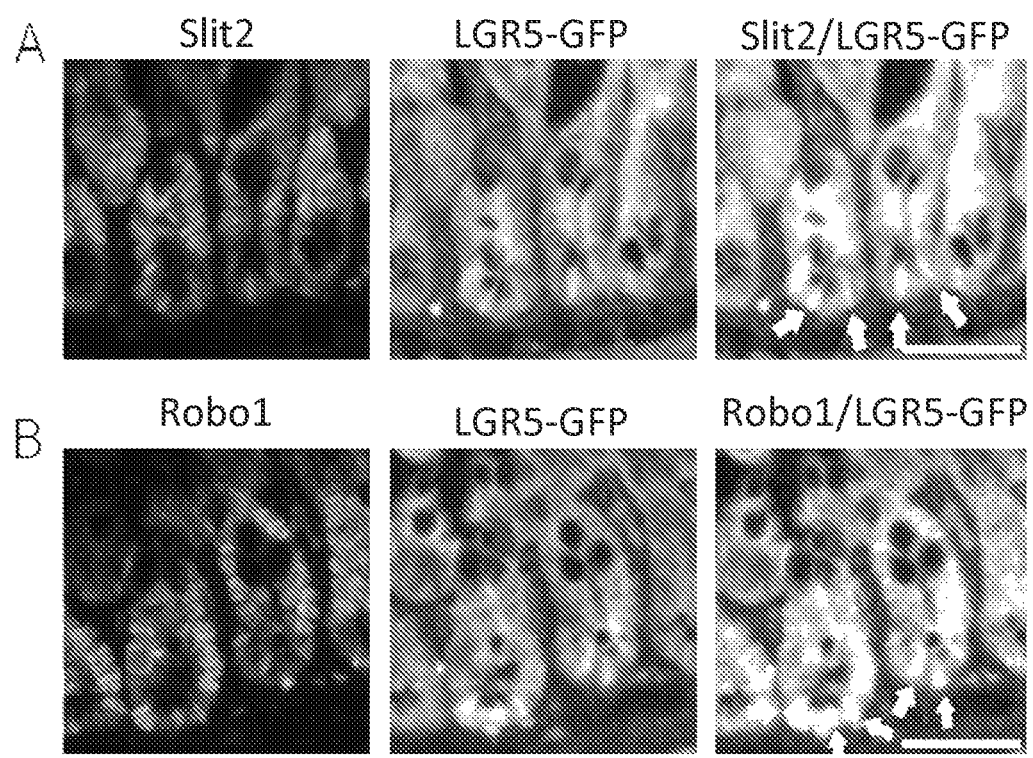
FIG. 6 describes expression of Slit2 and Robo1 on LGR5-GFP ISCs. Small intestines were harvested from adult LGR5-GFP mice (Barker et al., 2007 Nature 449, 1003-1007). Tissue sections were stained by antisense RNA probes for Slit2 and Robo1 mRNAs and by anti-GFP Ab followed by the fluorescent dye-conjugated secondary Ab. Tissue samples were observed under a laser scanning confocal microscope, and the recorded fluorescent images were merged. White arrows indicate co-localized Slit2- or Robo1-positive cells with LGR5-GFP-positive cells. White arrows indicate LGR5-positive ISCs co-localized with Slit2 (A) or Robo1 (B) mRNA. Results represent at least three separate experiments. Bars, 50 μm.

Which cell types expressed Slit2 and Robo1 in the small intestine was next investigated. It was found that Ki67-positive TA cells and LGR5-positive ISCs expressed Slit2 and Robo1 mRNAs (FIGS. 1B and C; FIGS. 4 and 5). In contrast, neither Slit2 mRNA nor Robo1 mRNA was visible in lysozyme-positive Paneth cells. Using intestinal specimens harvested from LGR5-EGFP-IRES-creERT2 (LGR5-GFP; (see, e.g., Barker, N., et al. (2007) Nature 449, 1003-1007) mice, it was also confirmed that Slit2 and Robo1 mRNAs were expressed by ISCs positive for LGR5-GFP at the bottom of the crypt (FIG. 1D; FIG. 6). The finding that ISCs and proliferating TA cells and perhaps other cells residing at the crypt expressed both Slit2 and Robo1 mRNAs explains why the expression of Slit2 and Robo1 is higher at the crypts than in the villi of the small intestine.

Example 2

Figure 7:
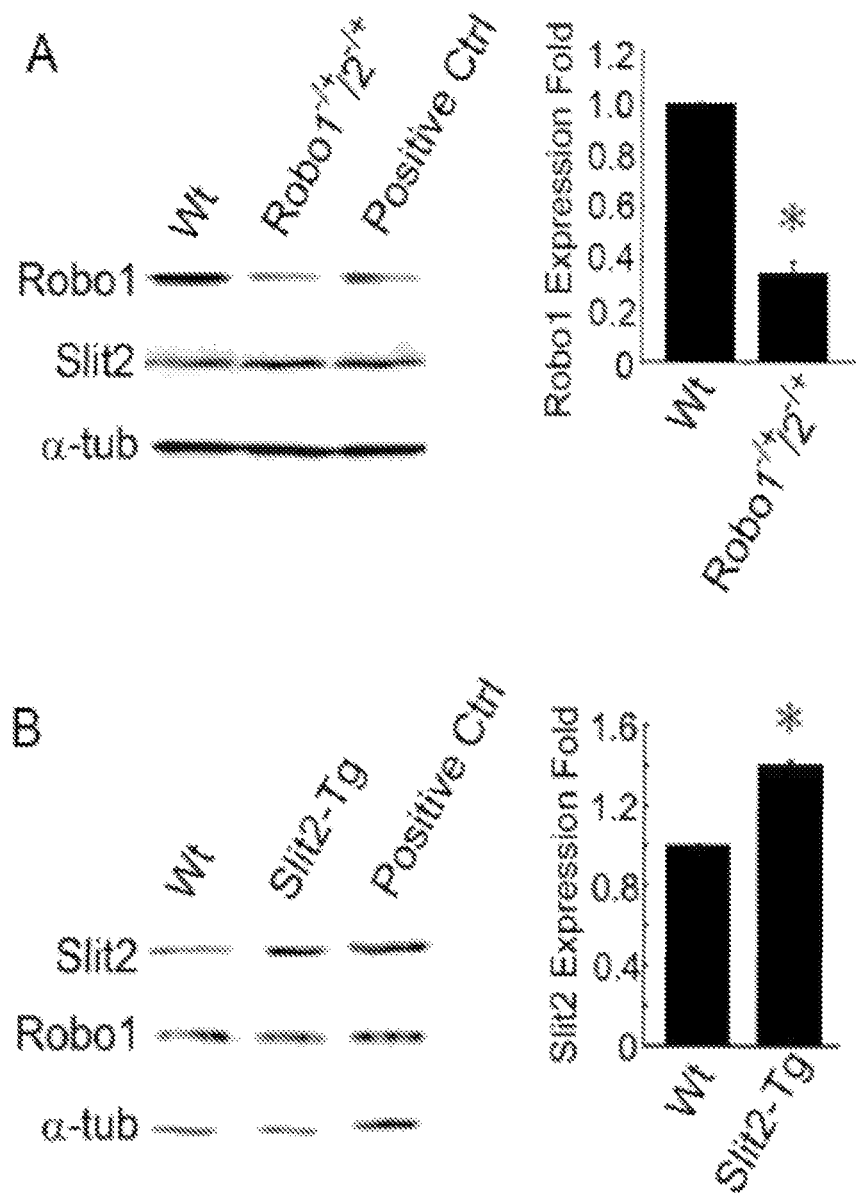
FIG. 7 describes characterization of Robo1$^{-/+}$/2$^{-/+}$ and Slit2-Tg mice. Lysates of the small intestine crypts isolated from Wt, Robo1$^{-/+}$/2$^{-/+}$ and Slit2-Tg mice were immunoblotted by affinity purified rabbit anti-Slit2 and Robo1 polyclonal Abs (Wang et al., 2003 Cancer Cell 4, 19-29) and the α-tubulin Ab (α-tub; A and B, left panels). The lysate of human colorectal epithelial HCT116 cells stably expressing Slit2 and Robo1 (Zhou et al., 2011 Cell Res. 21, 609-626) was also immunoblotted as positive control (Positive Ctrl) for Robo1, whereas the supernatant from HEK293 cells stably expressing human Slit2 (Wang et al., 2003 Cancer Cell 4, 19-29) was used as positive control for Slit2. The immunoblotting densities for Robo1 (A, right panel) and Slit2 (B, right panel) were analyzed. Results represent at least three separate experiments. *, p<0.05.

This example describes aberrant Intestinal Homeostasis in Robo1/2 Double Heterozygotes. Complete or partial genetic deletion of Robo1 is embryonic lethal (see, e.g., Andrews, W., et al., (2006) Development 133, 2243-2252) while mice with partial genetic deletion of both Robo1 and 2 (Robo1$^{-/+}$/2$^{-/+}$) are viable (see, e.g., Grieshammer, U., et al., (2004) Dev. Cell 6, 709-717; Long, H., et al., (2004) Neuron 42, 213-223). Thus, the intestinal morphology in Robo1/2 double heterozygotes was examined. Compared to Wt mice, Robo1/2 double heterozygotes displayed reduced expression of Robo1 protein, but not Slit2 or α-tubulin (α-tub; FIG. 7A). Notably, Robo2 mRNA was absent in the Wt small intestine, even though it was clearly present in the cerebellum (FIG. 2B). Robo1/2 double heterozygotes were thus considered as a murine model for partial genetic deletion of Robo1 for intestinal study.

Figure 8:
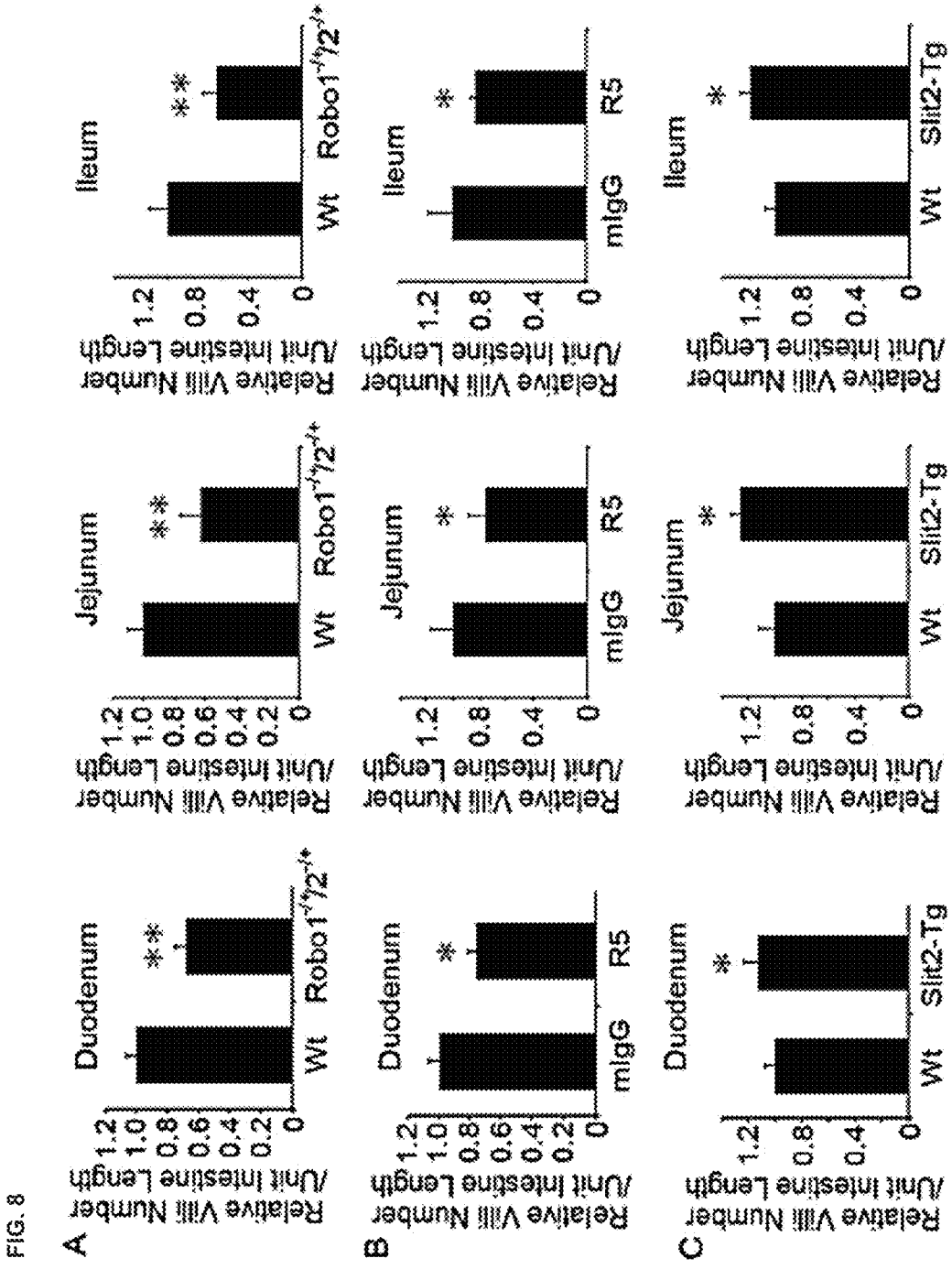
FIG. 8 describes distorted villi in small intestine. The numbers of villi per unit length of duodenum, jejunum and ileum (A-C) were counted double-blindly. Results represent more than forty tissue specimens in each group and the mean±S.D. of measurements of 10 tissue sections/mouse (four mice/group). *, p<0.05 and **, p<0.01.
Figure 9:
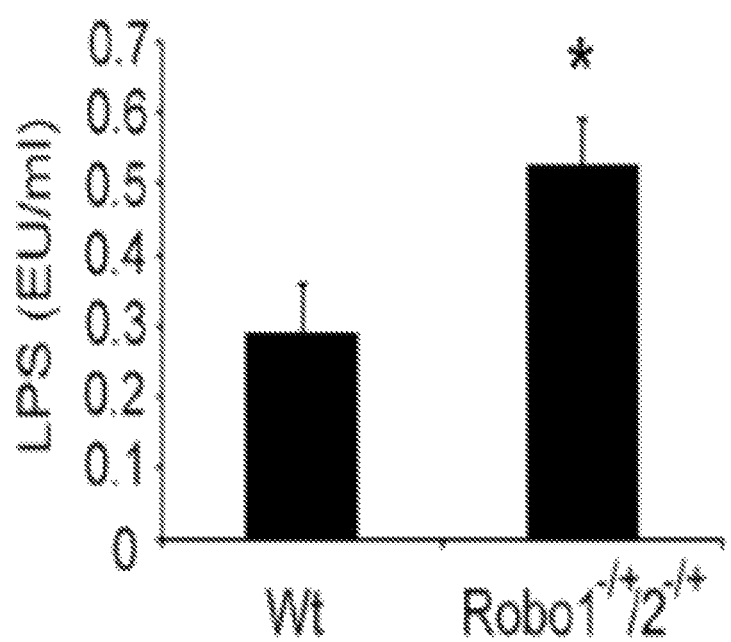
FIG. 9 shows determination of serum endotoxin. Blood samples were obtained from Wt and Robo1$^{-/+}$/2$^{-/+}$ mice and serum levels of lipopolysaccharides (LPS) were measured according to the manufacturer's protocol. Results are the mean±S.D. of measurements (three mice/group). *, p<0.05.
Figure 10:
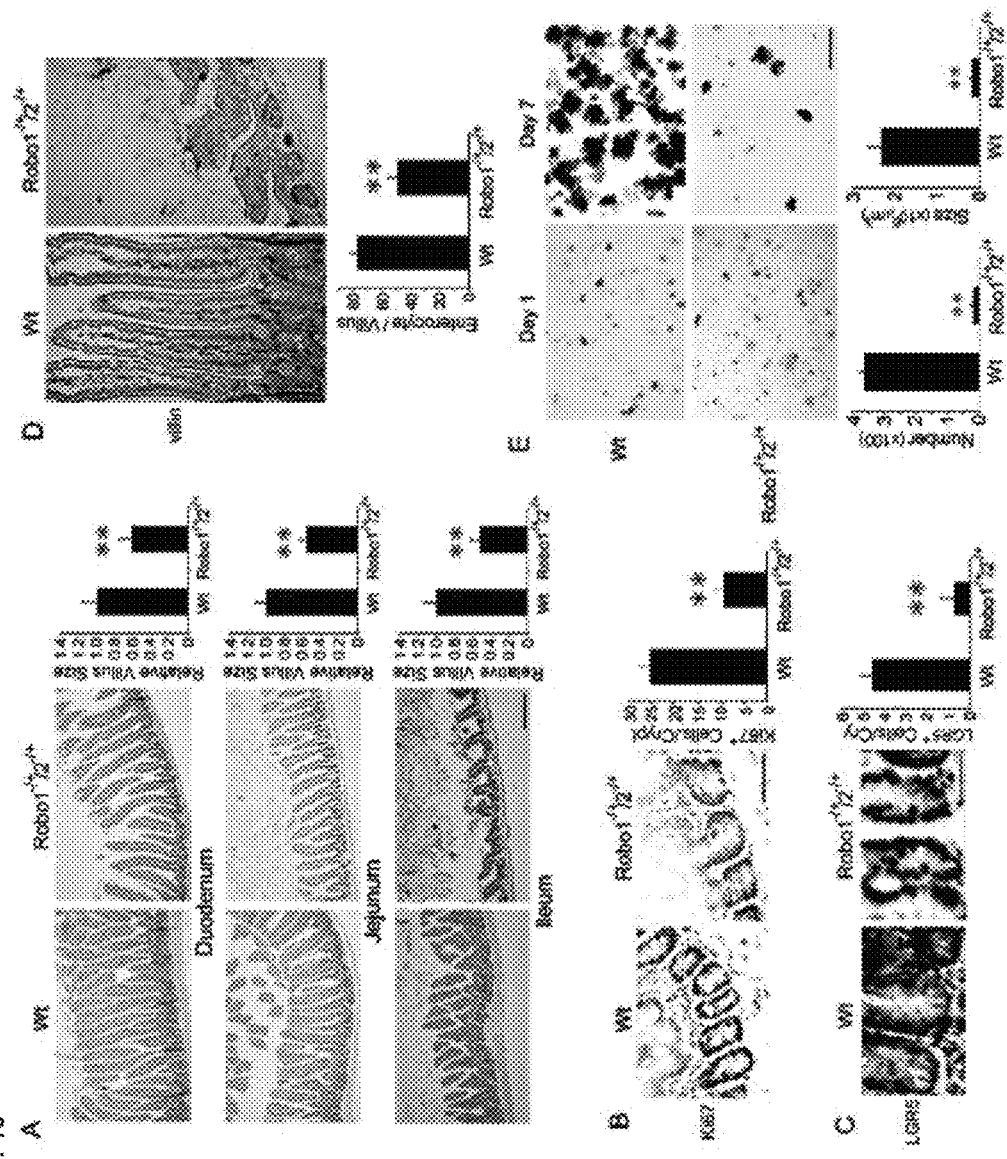
FIG. 10 describes phenotypic aberrations in Robo1$^{-/+}$/2$^{-/+}$ small intestine. (A) Macroscopic morphology of mouse small intestines. Sections of paraffin-embedded small intestines from wild-type C57 (Wt) and Robo1$^{-/+}$/2$^{-/+}$ mice (8 weeks old) were stained with hematoxylin & eosin (H&E). Relative villus sizes were measured and statistically analyzed. (B-D) Effects of partial Robo1/2 deficiency on the number and distribution of intestinal cells. Tissue sections of small intestines from Wt and Robo1$^{-/+}$/2$^{-/+}$ mice were immunohistochemically stained for Ki67-positive TA cells (B), LGR5-positive ISCs (C) and villin-positive enterocytes (D). The numbers of positive cells were counted in each crypt (B D). (E) The intestinal crypts isolated from Wt and Robo1$^{-/+}$/2$^{-/+}$ mice were cultured in vitro. The numbers and sizes of intestinal organoids were measured at day 7. Results represent more than forty stains of tissue specimens in each group and the mean±S.D. of measurements of 10 tissue sections/mouse (four mice/group). Bars, 200 μm for A and E and 50 μm for B-D. **, p<0.01.
Figure 11:
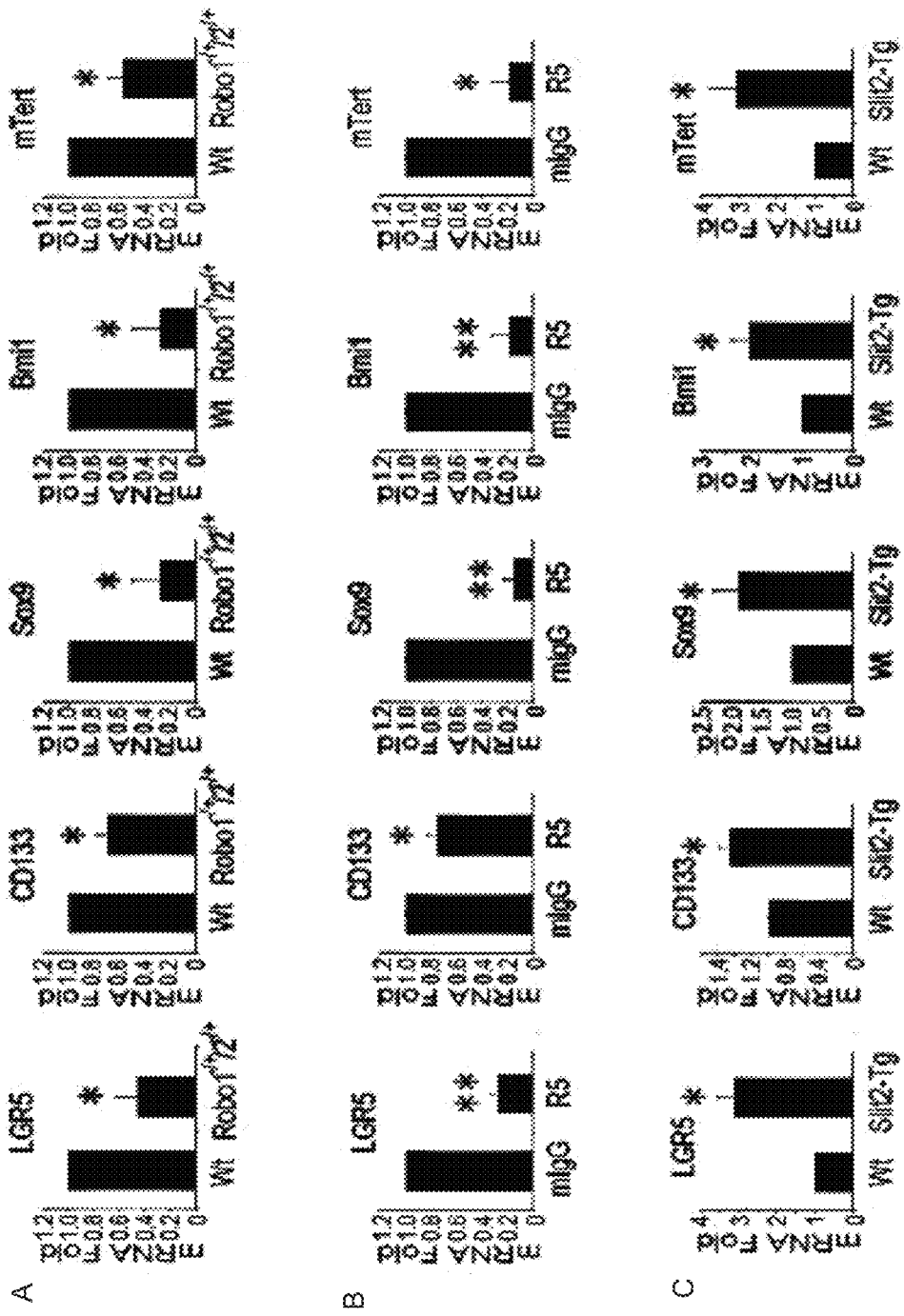
FIG. 11 shows intestinal expression of LGR5, CD133, Sox9, Bmi1 and mTert total RNAs were extracted from the small intestinal crypts of Wt and Robo1$^{-/+}$/2$^{-/+}$ mice (A), Wt mice treated with mIgG and R5 (B), and Wt and Slit2-Tg mice (C). They were reverse transcribed, PCR amplified and normalized to an endogenous β-actin control. Results represent the mean±S.D. of three independent experiments. *, p<0.05; **, p<0.01.

Compared to Wt littermates, Robo1/2 double heterozygotes had noticeably sparser, shorter and floppier villi in the representative sections of hematoxylin and eosin (H&E) staining throughout the entire small intestine (FIG. 10A and FIG. 8A). They displayed markedly fewer Ki67-positive TA cells (FIG. 10B), LGR5-positive ISCs (FIG. 10C), villin-positive enterocytes (FIG. 10D). They also had a higher level of endotoxin (FIG. 9), a functional indicator of intestinal impairment (see, e.g., Takashima, S., et al., (2011) J. Exp. Med. 208, 285-294). Intestinal crypts from Robo1/2 double heterozygotes were next isolated and it was found that Robo1$^{-/+}$/2$^{-/+}$ crypts failed to form intestinal organoids, also called mini-guts or enteroids, as compared to their Wt littermates (FIG. 10E). Using quantitative reverse transcriptase-polymerase chain reaction (qRT-PCR), the expression of LGR5, CD133, Sox9, Bmi1 and mTert mRNAs within the isolated crypts of mouse small intestines were determined (see, e.g., Tian, H., et al., (2011) Nature 478, 255-259; Takeda, N., et al., (2011) Science 334, 1420-1424; Yan, K. S., et al. (2012) PNAS 109, 466-471). As expected, the expression of LGR5, CD133, Sox9, Bmi1 and mTert mRNAs was significantly reduced in the small intestine of Robo1$^{-/+}$/2$^{-/+}$ mice when compared to their Wt littermates (FIG. 11A). These results indicate that inactivation of Slit-Robo signaling reduced the numbers of ISCs, TA cells and enterocytes, leading to villus atrophy in the small intestine.

Example 3

Figure 12:
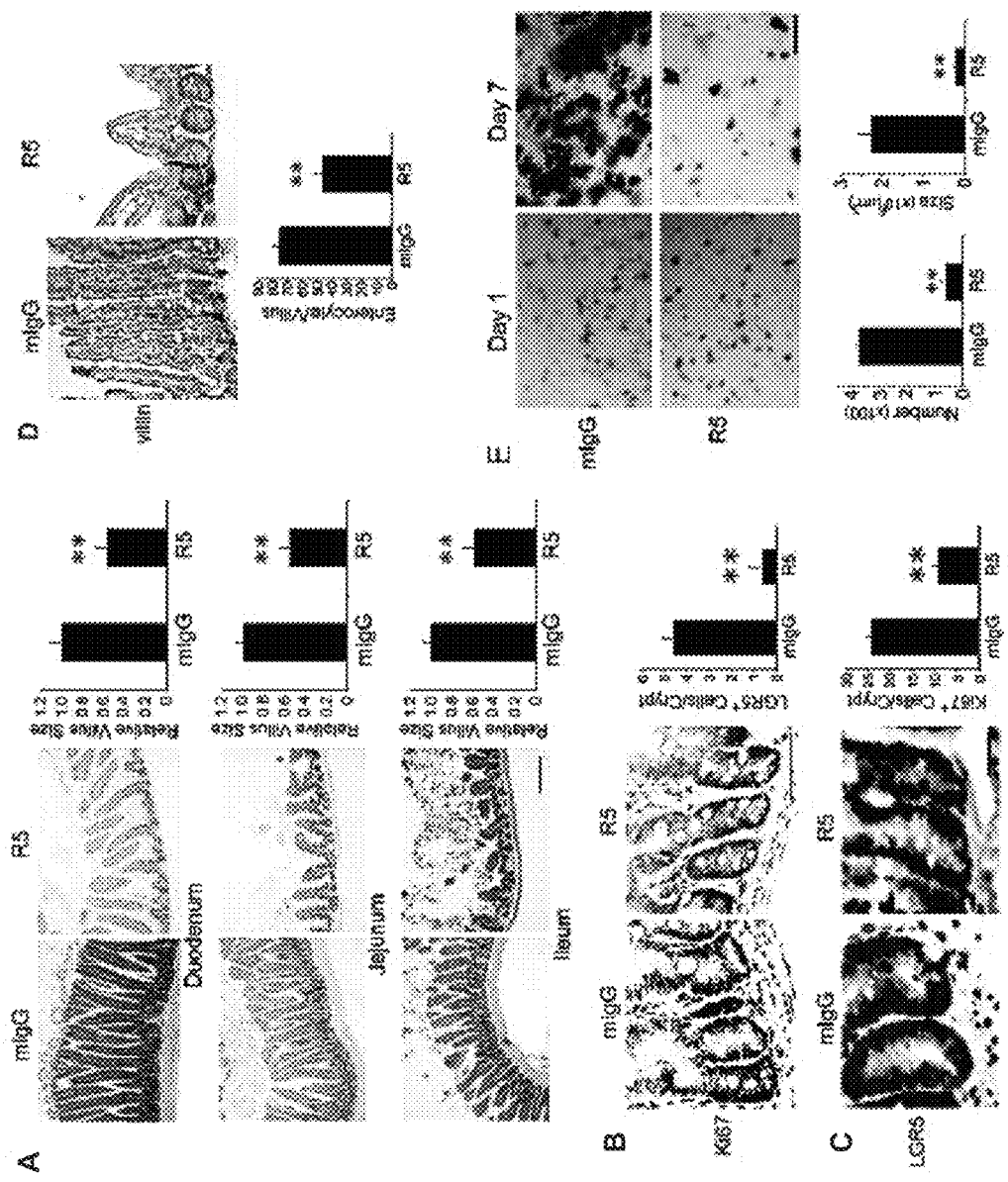
FIG. 12 describes neutralization of Slit2 binding to Robo1 retards small intestinal regeneration (A) Effects of R5 on intestinal histology. Wt mice (8 weeks old) were treated daily with mIgG or R5 for 6 consecutive days. Small intestines were stained with H&E, and the relative villus sizes were measured and statistically analyzed. (B-D) Impacts of R5 on the number and distribution of intestinal cells. Wt mice were treated with mIgG or R5, and their small intestines were immunohistochemically stained for Ki67 (B), LGR5 (C) and villin (D). The numbers of positive cells were counted in each crypt (B-D). (E) In vitro culture of the isolated Wt intestinal crypts in the presence of mIgG or R5. The numbers and sizes were measured on day 7. Results represent more than forty stains of tissue specimens in each group and the mean±S.D. of measurements of 10 tissue sections/mouse (four mice/group). Bars, 200 μm for A and E and 50 μm for B-D. **, p<0.01.

This example describes how neutralization of Slit2 binding to Robo1 inhibits intestinal development. To complement the findings in the Robo1$^{-/+}$/2$^{-/+}$ intestine, whether neutralization of Slit2 binding to Robo1 could temporally prevent intestinal regeneration was tested. R5, a monoclonal antibody (mAb) that binds to the first immunoglobulin domain of Robo1 and neutralizes Slit2 binding to Robo1 was used (see, e.g., Wang, B., et al., (2003) Cancer Cell 4, 19-29; Mertsch, S., et al., (2009) J. Neurooncol. 87, 1-7; Wang, L. J., et al., (2008) Cancer Sci. 99, 510-517; Urbich, C., et al., (2009) Blood 113, 5669-5679; Zhang, B., et al., (2009) Blood 114, 4300-4309; Yang, X. M., et al., (2010) Biochem. Biophys. Res. Commun. 396, 571-577; Khusial, et al., (2010) Oncotarget 1(3) 198-209; Ye, B. Q., et al., (2010) J. Immunol. 185, 6294-6305; Zhou, W. J., et al., (2011) Cell Res. 21, 609-626; Guijarro-Muñoz, I., et al., (2012) Exp. Cell Res. 318, 371-378). It should be noted that R5 only recognizes Robo1, but not Robo2-4 (see, e.g., Zhou, W. J., et al., (2011) Cell Res. 21, 609-626). Wt mice were treated daily for 6 days with intraperitoneal injection of isotype-matched irrelevant mouse IgG (mIgG) or R5. Compared to untreated mice, the intestinal accumulation of mIgG or R5 in the recipient mice was verified by staining with the FITC-conjugated anti-mouse IgG Ab. R5, but not mIgG, reduced villus size (FIG. 12A) and number (FIG. 8B) in the small intestine and decreased the numbers of TA cells (FIG. 12B), ISCs (FIG. 12C) and enterocytes (FIG. 12D). Compared to mIgG, R5 potently inhibited in vitro formation of intestinal organoids isolated from Wt mice (FIG. 12E). The expression of LGR5, CD133, Sox9, Bmi1 and mTert mRNAs was also mitigated in the small intestine of R5-treated Wt mice as compared to their mIgG-treated counterparts (FIG. 11B). These findings vividly phenocopy the aberrations observed in the small intestines of Robo1/2 double heterozygotes, attesting to the biological significance of Slit-Robo signaling in intestinal homeostasis. Notably, the inhibitory action of R5 that is specific for Robo1 is fully consistent with the evidence of no detectable expression of intestinal Robo2 mRNA (FIG. 2B), arguing collectively for the importance of Robo1, but not Robo2, in intestinal regeneration.

Example 4

Figure 13:
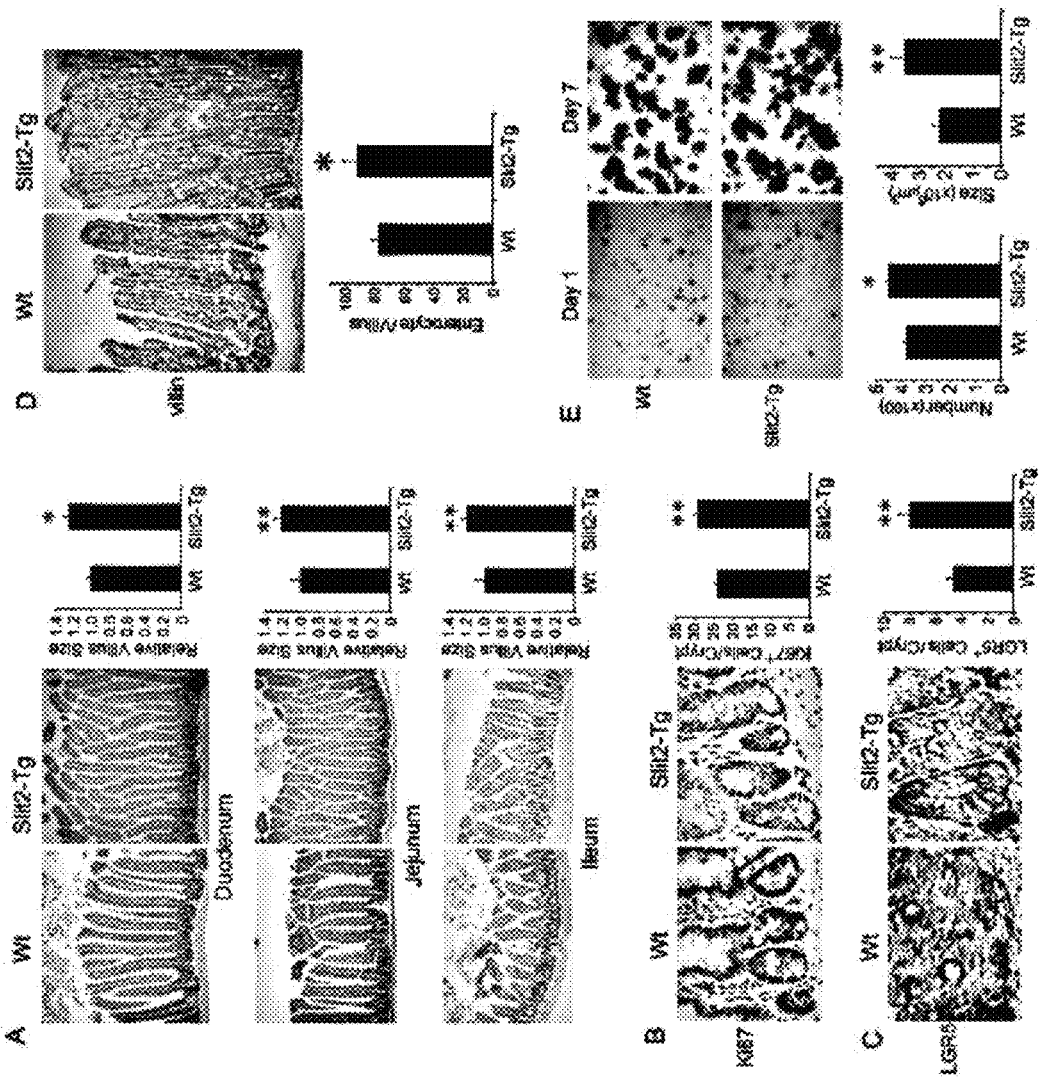
FIG. 13 describes how Slit2 transgene enhances small intestinal regeneration (A) Effects of Slit2 overexpression on intestinal morphology. Small intestines from Wt and Slit2-Tg mice (both at 8 weeks old) were stained with H&E, and the relative villus sizes were measured and statistically analyzed. (B-D) Effects of Slit2 overexpression on the number and distribution of intestinal cells. Small intestines from Wt and Slit2-Tg mice were immunohistochemically stained for Ki67 (B), LGR5 (C) and villin (D). The numbers of positive cells were counted in each crypt (B-D). (E) The intestinal crypts isolated from Wt and Slit2-Tg mice were in vitro cultured and the numbers and sizes of intestinal organoids were measured at day 7. Results represent more than forty stains of tissue specimens in each group and the mean±S.D. of measurements of 10 tissue sections/mouse (four mice/group). Bars, 200 μm for A and E and 50 μm for B-D. *, p<0.05; **, p<0.01.

This example describes how Slit2 transgene induces villus hypertrophy. It was next reasoned that ectopic expression of Slit2 might augment ISCs and their daughter cells, leading to proliferation of intestinal epithelial cells. To test this hypothesis, the intestinal phenotypic changes in Slit2 transgenic (Slit2-Tg) mice driven by the pCMV promoter was examined for efficient, but non-selective expression of human Slit2 transgene (see, e.g., Yang, X. M., et al., (2010) Biochem. Biophys. Res. Commun. 396, 571-577; Ye, B. Q., et al., (2010) J. Immunol. 185, 6294-6305; Han, H. X., and Geng, J.-G. (2011) Acta Pharmacol. Sin. 32, 1327-1336; Guo, S. W., et al., 2012) Reprod. Sci. [Epub ahead of print]). As compared to Wt mice, Slit2-Tg mice displayed an increased expression of Slit2 protein, but not Robo1 or α-tubulin, in the small intestinal crypts (FIG. 7B). When compared to Wt mice, Slit2-Tg mice presented noticeably thicker, longer, enlarged and outnumbered villi (FIG. 13A and FIG. 8C), with increased numbers of proliferating TA cells (FIG. 13B), ISCs (FIG. 13C) and enterocytes (FIG. 13D). Notably, the intestinal crypts isolated from Slit2-Tg mice formed more and larger intestinal organoids as compared to their Wt counterparts (FIG. 13E). As compared to Wt mice, the expression of LGR5, CD133, Sox9, Bmi1 and mTert mRNAs was significantly augmented in the small intestine of Slit2-Tg mice (FIG. 11C). The staining of bromodeoxyuridine (BrdU) at the intestinal crypt was also substantially higher in Slit2-Tg mice than their Wt counterpart (data not shown). Considering the findings in Robo1/2 double heterozygotes (FIG. 10) and R5-treated Wt mice (FIG. 12), these results provide convergent evidence for the functional significance of Slit-Robo signaling in intestinal regeneration.

Example 5

Figure 14:
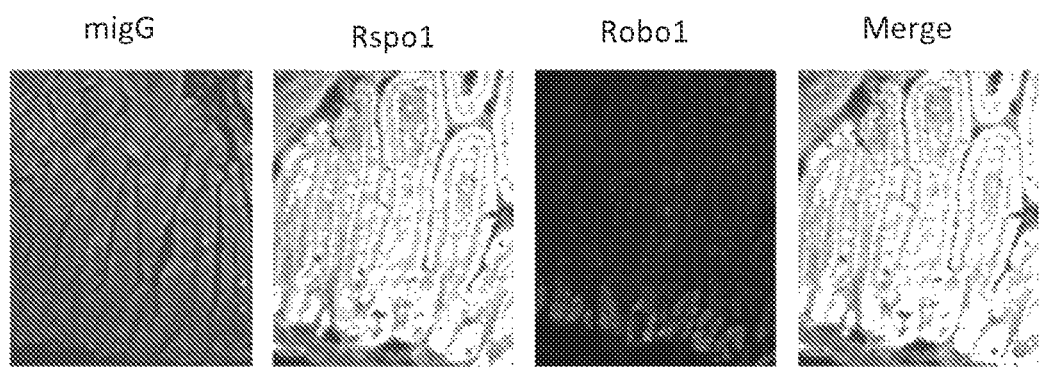
FIG. 14 shows co-localization of Rspo1 with Robo1 at the intestinal crypt. Tissue sections of the isolated Wt small intestine were stained for Rspo1 protein and Robo1 mRNA. Immunofluorescent images were observed under a laser scanning confocal microscope, and the recorded fluorescent images were then merged. Results are representatives of more than three separate experiments. Bars, 50 μm.

This example describes Rspo1 binds to extracellular Robo1. To investigate how Slit-Robo signaling induces Wnt/β-catenin activation during intestinal development, whether Rspo1 would co-localize and consequently bind to Robo1 at the intestinal crypt was tested. Indeed, the intestinal expression of Rspo1 was detected in the tissue sections of adult small intestine (FIG. 14). Interestingly, Rspo1 co-localized with Robo1 at the intestinal crypts. Endogenous Robo1, immunoprecipitated from the Wt intestinal crypt lysates, was also found to associate with native Rspo1 (FIG. 15A and FIG. 16A), further suggesting an interaction between these two proteins.

Figure 15:
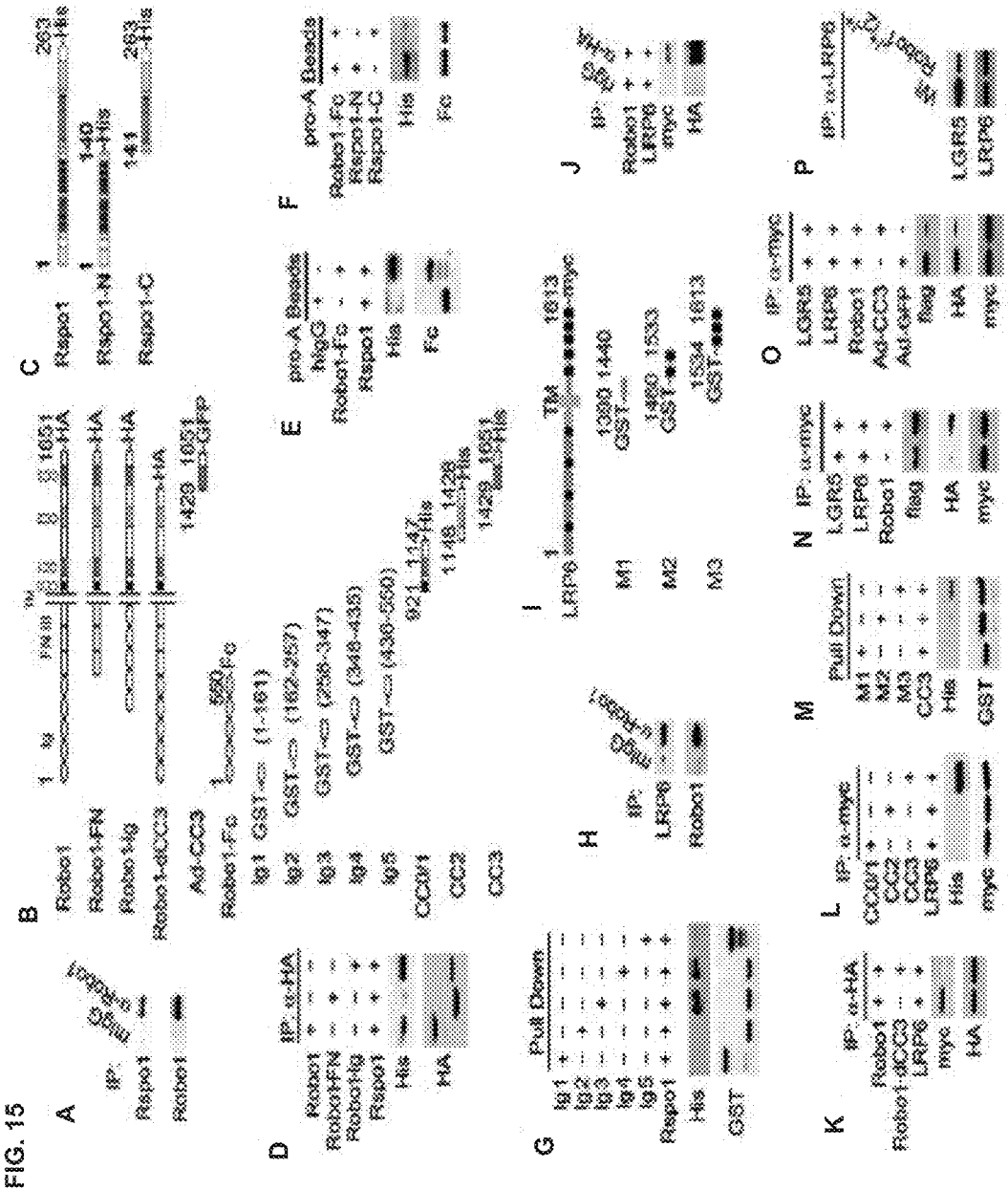
FIG. 15 describes how Rspo1 binds to extracellular Robo1 while cytoplasmic Robo1 binds to LRP6 and promotes LRP6 association with LGR5. (A) Robo1 associates with Rspo1. Endogenous Robo1 was immunoprecipitated from the crypt lysates of C57 small intestines, followed by immunoblotting for Rspo1 and Robo1. (B) Schematic illustration of Robo1 constructs. The plasmids of full-length and wild-type Robo1 (Robo1), Robo1 encoding three extracellular fibronectin (FN)-like domains, but without five extracellular immunoglobulin (Ig)-like domains (Robo1-FN), Robo1 encoding five extracellular Ig-like domains, but without three extracellular FN-like domains (Robo1-Ig), and Robo1 with deleted cytoplasmic CC3 motif (Robo1-dCC3) were fused with HA tags for mammalian expression (Wong et al., 2001). Recombinant human Robo1 encoding the extracellular five Ig-like domains fused with the Fc domains of human $IgG_1$ (Robo1-Fc) was constructed, expressed and isolated (Wang, Y., et al., 2007 Proc. Natl. Acad. Sci. USA 104, 11328-11333f). The extracellular Ig domains 1-5 of Robo1 fused with GST (GST-Ig1-5) and the cytoplasmic CC0/1-3 motifs of Robo1 fused with the 6-His tags (rCC0/1-3) were also constructed, expressed and isolated. (C) Schematic illustration of Rspo1 constructs. The plasmid of full-length and wild-type Rspo1 fused with a 6-His tag (Rspo1) was constructed for mammalian transfection and expression. In addition, the amino-terminal segment of Rspo1 including two furin-like cysteine-rich domains (rRspo1-N) and the carboxyl-terminal segment of Rspo1 including one TSR repeat fused with 6-His tags (rRspo1-C) were constructed, expressed and isolated. (D) Transfected Robo1 binds to Rspo1. 293 cells transfected with the plasmids Robo1, Robo1-FN and Robo1-Ig were incubated with rRspo1. After washing, transfected Robo1, Robo1-FN and Robo1-Ig were immunoprecipitated by the anti-HA Ab followed by immunoblotting for Rspo1 (His) and Robo1 (HA). (E and F) Direct binding to Rspo1 or Rspo1-N to Robo1. Protein A (Pro-A)-Sepharose beads were first incubated with human IgG (hIgG) or Robo1-Fc. After washing, they were incubated with rRspo1 (E) or rRspo1-N and rRspo1-C (F), followed by immunoblotting for His (rRspo1, rRspo1-N and rRspo1-C) and Fc (hIgG and Robo1-Fc), respectively. (G) Rspo1 interacts with the extracellular Ig 3 and 4 domains of Robo1. The glutathione-Sepharose beads were incubated with GST-Ig1-5. After washing, they were incubated with rRspo1, followed by immunoblotting for rRspo1 (His) and GST. (H) Robo1 associates with LRP6. Endogenous Robo1 was immunoprecipitated from the crypt lysates of C57 small intestines, followed by immunoblotting for LRP6 and Robo1. (I) Schematic illustration of LRP6 constructs. The plasmid of full-length LRP6 fused with a myc tag (LRP6) was constructed for mammalian transfection and expression. In addition, three deletion mutants of the LRP6 cytoplasmic domains fused with GST (GST-M1-3) were constructed, expressed and isolated. (J and K) Robo1 binds to LRP6 through the cytoplasmic CC3 motif of Robo1. 293 cells were co-transfected with the plasmids of Robo1 or Robo1-dCC3 and LRP6. Transfected Robo1 was immunoprecipitated by the anti-HA Ab, followed by immunoblotting for LRP6 (myc) and Robo1 (HA). (L) LRP6 interacts with CC3. 293 cells transfected with the LRP6 plasmid were incubated with rCC0/1, rCC2 and rCC3. After washing, transfected LRP6 was immunoprecipitated by the anti-HA Ab, followed by immunoblotting for rCC0/1, rCC2 and rCC3 (His) and LRP6 (myc). (M) LRP6 M3 binds to CC3. The glutathione-Sepharose beads were incubated with the GST-M1-3. After washing, they were incubated with rCC3, followed by immunoblotting for rCC3 (His) and rGST-M1-3. (N and O) Transfected Robo1 enhances LRP6 binding to LGR5. 293 cells were co-transfected with the plasmids of LGR5 and LRP6, in the presence or absence of the Robo1 plasmid (N). Alternatively, 293 cells were co-transfected with the plasmids of LGR5, LRP6 and Robo1, followed by infection with Ad-GFP or Ad-CC3 (0). Lysates of these transfectants were immunoprecipitate for LRP6 (myc) and immunoblotted for LGR5 (flag), LRP6 (myc) and Robo1 (HA), respectively. (P) Endogenous Robo1 promotes LRP6 association with LGR5. Lysates of the Wt and Robo1$^{-/+}$/2$^{-/+}$ intestinal crypts were immunoprecipitate for LRP6 and immunoblotted for LGR5 and LRP6. Results represent at least three separate experiments.
Figure 16:
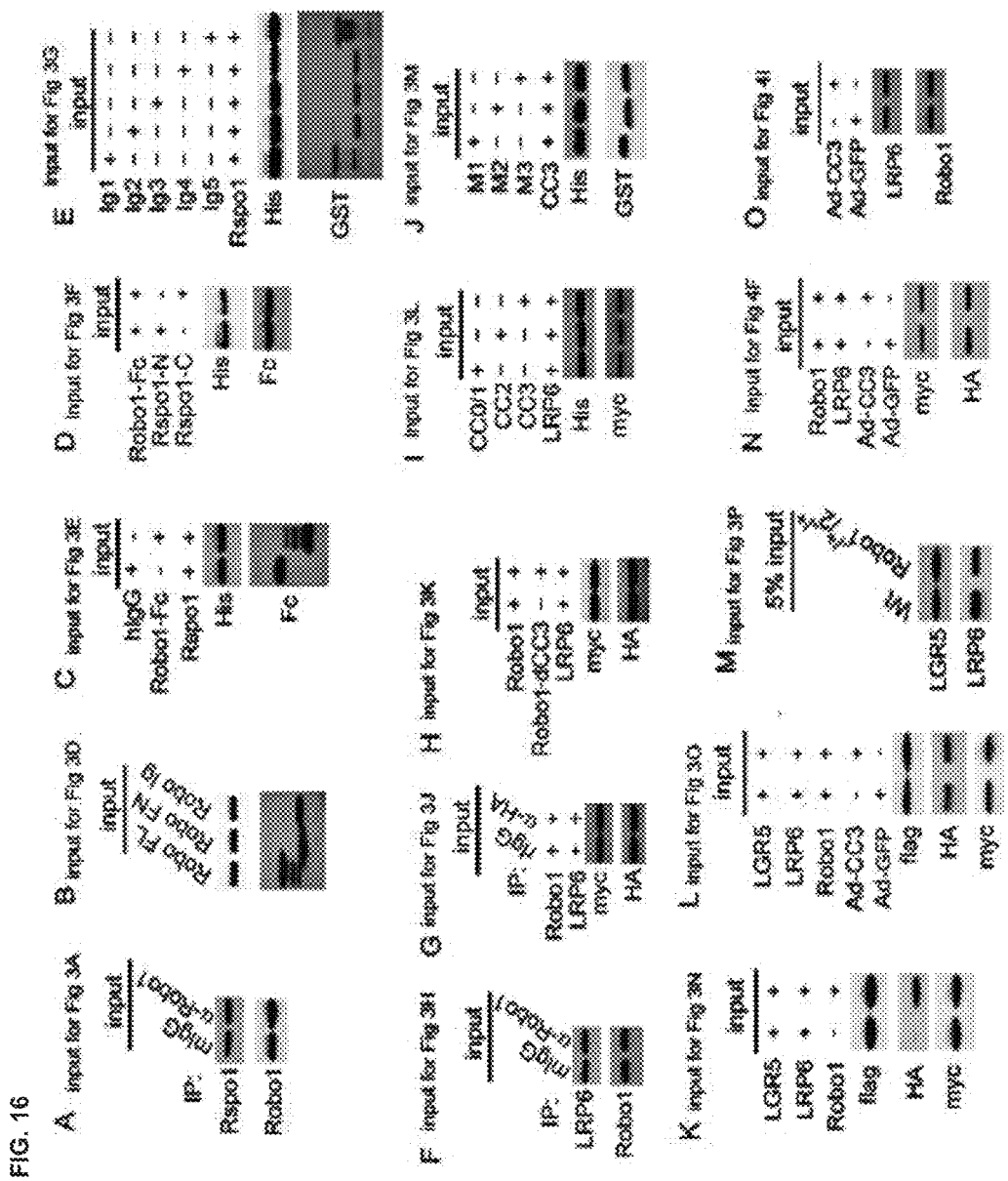
FIG. 16 describes input controls of immunoprecipitation, pulldown and immunoblotting. The input controls for the indicated panels in FIGS. 3 and 4 represent more than three separate experiments.
Figure 17:
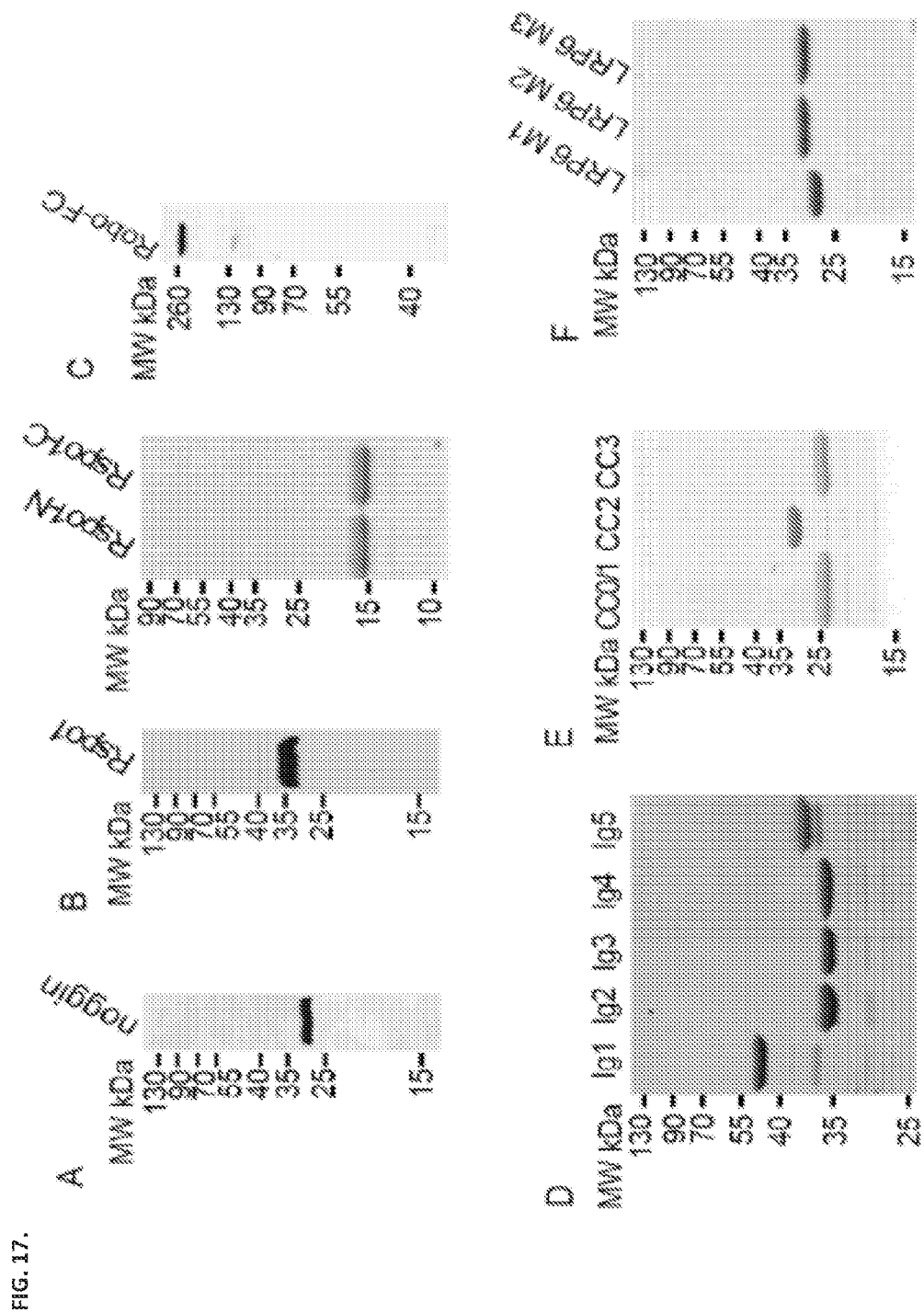
FIG. 17 describes purification of rs wild-type and deletion mutant proteins. Coomassie blue staining of purified recombinant noggin (A), rRspo1, rRspo1-N and rRspo1-C (B), Robo1-Fc (under non-reducing conditions; C), GST-Ig1-5 (D), rCC0/1-3 (E) and GST-M1-3 (F). Results are representatives of more than three separate protein preparations.

To confirm our initial findings, various deletion mutants of Robo1 fused with hemagglutin (HA) tag were employed (FIG. 15B) (see, e.g., Wong, K., et al., (2001) Cell 107, 209-221). Recombinant human Rspo1 fused with 6-His (His) tag expressed in Sf9 insect cells (rRspo1; FIG. 15C and FIG. 17B) were also purified. Human embryonic kidney 293 (293) cells were transfected with the indicated plasmids (FIG. 15B). Following incubation, immunoprecipitation was performed by the anti-HA Ab, followed by immunoblotting with the Abs for rRspo1 (His) and Robo1 (HA). It was found that Robo1 and Robo1-Ig, but not Robo1-FN, bound to rRspo1 (FIG. 15D and FIG. 16B). Compared to human IgG (hIgG) bound Protein A (Pro-A) beads, recombinant Robo1-Fc chimera (rRobo1-Fc; FIG. 17C) bound Pro-A beads precipitated rRspo1 (His; FIG. 15E and FIG. 16C). Additionally, rRobo1-Fc bound Pro-A beads precipitated purified recombinant Rspo1-N (rRspo1-N), but not recombinant Rspo1-C (rRspo1-C; FIGS. 15C and F and FIGS. 16D and 17B). To determine which extracellular Ig domains of Robo1 could recognize Rspo1, recombinant extracellular Ig domains 1-5 of Robo1 fused with glutathione S-transferase were constructed, expressed and purified (GST-Ig1-5; FIG.

15B and FIG. 16D). Using the pulldown assay, it was found that rRspo1 bound to GST-Ig3 and 4, but not GST-Ig1, 2 and 5 (FIG. 15G and FIG. 16E), whereas Slit2 bound to GST-Ig1, but not GST-Ig2-5 (see, e.g., Morlot, C., et al., (2007) PNAS 104, 14923-14928). Notably, rRspo1 failed to enhance recombinant Slit2 (rSlit2) binding to rRobo1-Fc (FIG. 18A), whereas rSlit2 failed to enhance rRspo1 binding to rRobo1-Fc (FIG. 18B), indicating that Slit2 neither facilitates nor competes with Rspo1 for Robo1. These biochemical data indicate that the amino portion of Rspo1 containing two furin-like domains interacts directly with the extracellular Ig 3 and 4 domains of Robo1.

Example 6

This example describes how cytoplasmic Robo1 binds to LRP6 and promotes LRP6 association with LGR5. As Wnt3a and/or Rspo1-induced LRP6 phosphorylation is a key event in receptor activation (see, e.g., Tamai, et al., (2004) Mol. Cell 13 149-156; MacDonald, B. T., et al., (2009) Dev. Cell. 17, 9-26; Carmon, K. S., et al., (2011) PNAS 108, 11452-11457; Carmon, K. S., et al., (2012) Mol. Cell. Biol. 32, 2054-2064; Gong, X., et al., (2012) PLoS One 7, e37137), it was asked whether Robo1 could bind to LRP6. To test this, Robo1 were immunoprecipitated from the lysates of Wt intestinal crypts, followed by immunoblotting for LRP6. Endogenous Robo1 was found to associate with native LRP6 (FIG. 15H and FIG. 16F). To verify this unexpected finding, 293 cells were co-transfected with the plasmids of Robo1 or Robo1-dCC3 (FIG. 15B) (see, e.g., Wong, K., et al., (2001) Cell 107, 209-221) and LRP6 (FIG. 15I). It was found that Robo1, but not Robo1-dCC3, co-immunoprecipitated LRP6 (myc; FIGS. 15J and K and FIGS. 16G and H), suggesting that Robo1 binds to LRP6 through its cytoplasmic CC3 motif. To confirm this, recombinant cytoplasmic CC0/1-3 domains of Robo1 fused with His tag (rCC0/1-3; FIG. 15B and FIG. 17E) and recombinant cytoplasmic LPR6 M1-3 fused with GST (GST-M1-3; FIG. 15I and FIG. 17F) were constructed and isolated. Indeed, immunoprecipitated LRP6 bound to rCC3, but not to rCC0/1 and CC2 (His; FIG. 15L and FIG. 16I), whereas GST-M3, but not GST-M1 and GST-M2, pulled down rCC3 (FIG. 15M and FIG. 16J).

Given that LGR4/5 associate with the Fzd/LRP Wnt receptor complex (see, e.g., de Lau et al., (2011) Nature 476, 293-297), it was next investigated whether the newly identified Robo1-LRP6 complex could modulate the association of LGR4/5 with the Fzd/LRP complex. To test this, the mammalian expression plasmid of LGR5 fused with a flag tag was constructed and co-transfected 293 cells with the LGR5 and LRP6 plasmids, in the presence or absence of the Robo1 plasmid. It was found that expression of Robo1 (HA) increased LRP6 (myc) association with LGR5 (flag) (FIG. 15N and FIG. 16K). In addition, Ad-CC3, but not Ad-GFP, potently diminished the LRP6-LGR5 complex in 293 cells expressing LGR5, LRP6 and Robo1 (FIG. 15O and FIG. 16L). Using the intestinal crypts isolated from Wt and Robo1$^{-/+}$/2$^{-/+}$ mice, it was further demonstrated that genetic deletion of Robo1/2 clearly reduced association of endogenous LRP6 with native LGR5 (FIG. 15P and FIG. 16M). These results collectively indicate that the cytoplasmic CC3 motif of Robo1 binds directly to the carboxyl portion of cytoplasmic LRP6, whereas Robo1 enhances the formation of LRP6-LGR5 complex. The finding that ectopic expression of CC3 inhibits the formation of Robo1-LRP6 complex (FIG. 15L-M) and LRP6-LGR5 complex (FIG. 15O) also argues for a critical contribution of the Robo1-LRP6 complex induced by Rspo1 and Slit2 to the formation of LRP6-LGR5 complex.

Example 7

Figure 19:
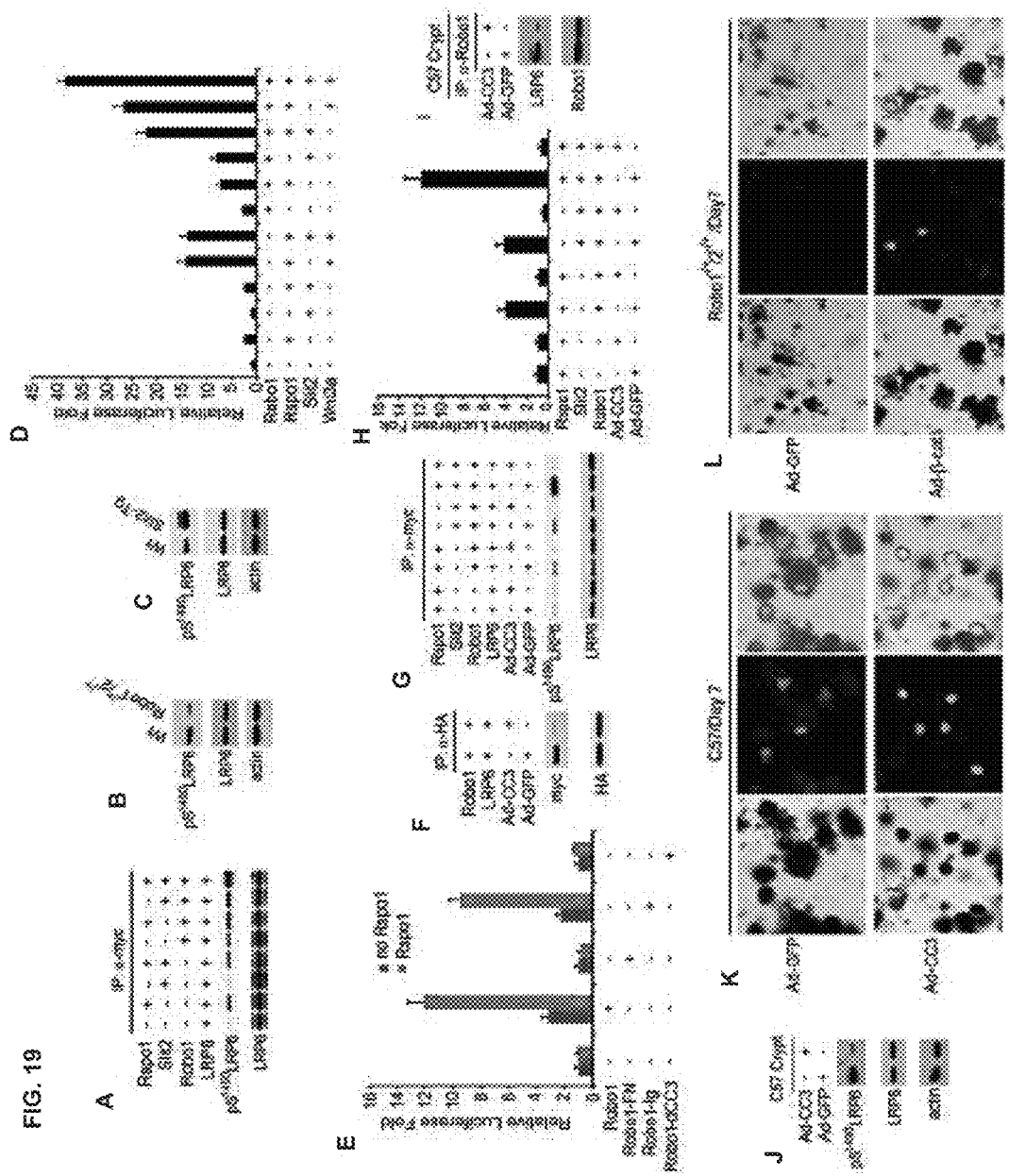
FIG. 19 describes the significance of Robo1-LRP6 complex in canonical Wnt activation. (A) Slit2 potentiates Rspo1-induced LRP6 phosphorylation in Robo1-expressing 293 cells. 293 cells, transfected with LRP6 and/or Robo1 plasmids, were incubated with rRspo1 and/or rSlit2. After washing, cell lysates were immunoprecipitated for LRP6 (myc), followed by immunoblotting for $pS^{1490}$LRP6 and LRP6. (B and C) Slit-Robo signaling modulates LRP6 phosphorylation. The intestinal crypt lysates of Wt, Robo1$^{-/+}$/2$^{-/+}$ and Slit2-Tg mice were directly immunoblotted for $pS^{1490}$LRP6, LRP6 and β-actin. (D and E) Slit2 potentiates TCF/LEF promoter activity elicited by Rspo1 and/or Wnt3a. 293 cells were co-transfected with the plasmids of TCF/LEF1 promoter luciferase reporter, β-gal, Robo1 (D), Robo1-FN, Robo1-Ig or Robo1-dCC3 (E). These were incubated with rRspo1 in the presence or absence of rSlit2 and/or rWnt3a. After washing, the luciferase activities of the TCF/LEF promoter in the cell lysates were determined and normalized against β-gal for expression efficiency. (F) CC3 inhibits Robo1 binding to LRP6. 293 cells were co-transfected with Robo1 and LRP6 plasmids, infected by Ad-CC3 and Ad-GFP and incubated with rRspo1 and/or rSlit2. Transfected Robo1 was immunoprecipitated by the anti-HA Ab, followed by immunoblotting for LRP6 (myc) and Robo1 (HA). (G and H) CC3 suppresses Rspo1/Slit2-induced LRP6 phosphorylation and TCF/LEF promoter activity. 293 cells were transfected with LRP6 and Robo1 plasmids, infected with Ad-GFP or Ad-CC3, and incubated with rRspo1 and/or rSlit2. Cell lysates were immunoprecipitated for LRP6 (myc), followed by immunoblotting for $pS^{1490}$LRP6 and LRP6 (G). Alternatively, 293 cells were co-transfected with the plasmids for TCF/LEF promoter luciferase reporter, β-gal and Robo1 and infected by Ad-GFP or Ad-CC3. Following incubation with rRspo1 and/or rSlit2, the luciferase activities of TCF/LEF promoter in the cell lysates were measured (H). (I and J) CC3 suppresses formation of endogenous Robo1-LRP6 complex and LRP6 phosphorylation. Lysates of the Wt intestinal crypts infected with Ad-GFP or Ad-CC3 were immunoprecipitated for native Robo1, followed by immunoblotting for LRP6 and Robo1 (I). Alternatively, they were directly immunoblotted for pS$^{1490}$LRP6, LRP6 and β-actin (actin; J). (K) CC3 inhibits development of intestinal organoids. The Wt intestinal crypts were infected with Ad-GFP or Ad-CC3 and the formation of intestinal organoids were examined on day 7. (H) Expression of β-catenin rescues Robo1$^{-/+}$/2$^{-/+}$ intestinal organoids. The Robo1$^{-/+}$/2$^{-/+}$ intestinal crypts were infected with Ad-GFP or Ad-β-catenin and the formation of intestinal organoids were examined on day 7. Results represent at least three separate experiments (A C, F and G, I and J, K and L) or the mean±S.D. of measurements of at least three independent experiments (D, E and H). Bars, 200 μm for K and L. *, $p<0.05$; **, $p<0.01$.

This example describes how Robo1 binding to LRP6 activates canonical Wnt signaling. Considering that LRP6 phosphorylation induced by Rspo1 activates Wnt/β-catenin signaling (see, e.g., Carmon, K. S., et al., (2011) PNAS 108, 11452-11457; Carmon, K. S., et al., (2012) Mol. Cell. Biol. 32, 2054-2064; Gong, X., et al., (2012) PLoS One 7, e37137), it was tested whether Slit-Robo signaling would modulate Rspo1-induced LRP6 phosphorylation and TCF/LEF1 promoter activity. As predicted, incubation of Robo1-negative 293 cells (see, e.g., Zhou, W. J., et al., (2011) Cell Res. 21, 609-626) with rRspo1, but not rSlit2, elicited pS$^{1490}$LRP6 phosphorylation (FIG. 19A). In the presence of Robo1, rRspo1 more potently induced pS1490LRP6 phosphorylation, whereas rSlit2 alone was also capable of inducing it. Importantly, rSlit2 potentiated Rspo1-elicitated pS$^{1490}$LRP6 phosphorylation. Compared to the Wt counterparts, the Robo1$^{-/+}$/2$^{-/+}$ intestinal crypts manifested decreased pS$^{1490}$LRP6 phosphorylation (FIG. 19B). In contrast, the Slit2-Tg intestinal crypts displayed increased pS$^{1490}$LRP6 phosphorylation (FIG. 19C). Incubation of Robo1-negative 293 cells with rRspo1 also triggered the TCF/LEF promoter luciferase activity (~2-3-fold; FIG. 19D). Notably, recombinant Wnt3a (rWnt3a), but not rSlit2, acted synergistically with rRspo1 for increasing the TCF/LEF promoter activity (~13-fold). However, transfection of 293 cells with the Robo1 plasmid augmented the TCF/LEF promoter activity (~2-3-fold). Importantly, the TCF/LEF promoter activity in Robo1-expressing 293 cells was induced by rRspo1 or rSlit2 alone (~6-7-fold), further induced by rRspo1 plus rSlit2 (~22-fold) or rRspo1 plus Wnt3a (~26-fold), and maximally induced by a combination of rRspo1, rSlit2 and rWnt3a (~40-fold).

Consistent with our biochemical finding that the cytoplasmic CC3 motif of Robo1 binds to LRP6 (FIG. 15K-M), transfection of 293 cells with the plasmids Robo1 and Robo1-Ig, but not the plasmids Robo1-FN and Robo1-dCC3, increased the TCF/LEF promoter activity in the presence or absence of rRspo1 (FIG. 19E). Following co-transfection with the indicated plasmids, 293 cells were infected with adenoviral GFP (Ad-GFP) or adenoviral CC3 (Ad-CC3). Compared to Ad-GFP, Ad-CC3 abolished the interaction of Robo1 (HA) with LRP6 (myc; FIG. 19F and FIG. 16N) and attenuated rRspo1 and/or rSlit2-induced pS$^{1490}$LRP6 phosphorylation (FIG. 19G) and TCF/LEF promoter activity (FIG. 19H). Infection of isolated Wt intestinal crypts with Ad-CC3, but not Ad-GFP, also diminished the interaction of endogenous Robo1 with native LRP6 (FIG. 19I and FIG. 16O), prevented pS$^{1490}$LRP6 phosphorylation (FIG. 19J), and suppressed formation of intestinal organoids isolated from the Wt intestinal crypts (FIG. 19K). These results show that cytoplasmic Robo1 is required for LRP6 interaction in order to see the Rspo1- and Slit2-mediated pS$^{1490}$LRP6 phosphorylation, TCF/LEF promoter activation and formation of intestinal organoids.

Example 8

Figure 20:
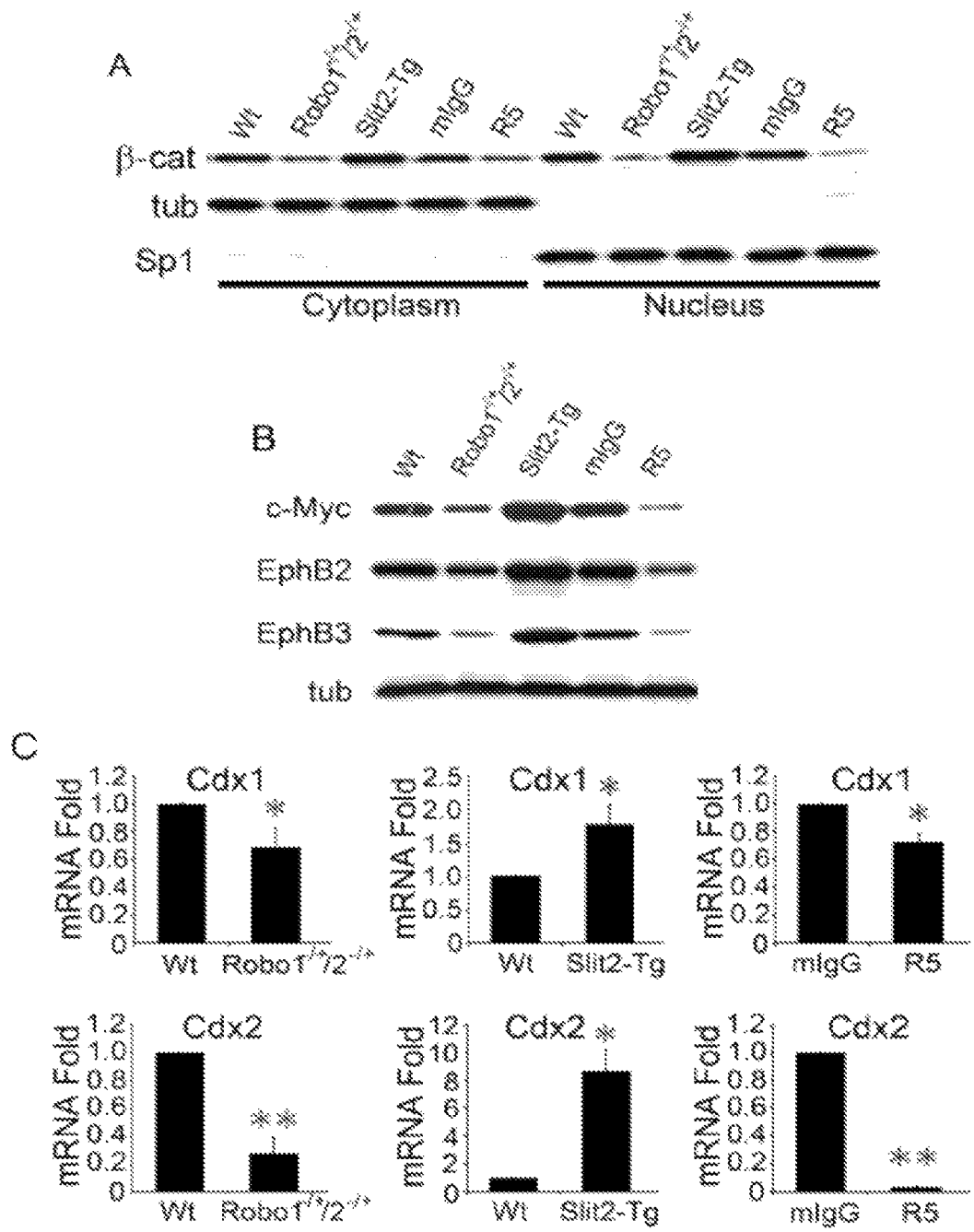
FIG. 20 describes translocation of β-catenin and expression of Wnt targeting genes in small intestine. Small intestines were obtained from Wt, Robo1$^{-/+}$/2$^{-/+}$, Slit2-Tg mice and Wt mice pretreated with mIgG and R5. The intestinal lysates were fractionated and immunoblotted for β-catenin, α-tub (a marker for the cytoplasm) and Sp1 (a marker for the nucleus; A) or directly immunoblotted for c-Myc, EphB2, EphB3 and α-tub (B). Alternatively, total RNAs extracted from these mice were reverse transcribed, PCR amplified for Cdx1 and 2, which were normalized to an endogenous β-actin control (C). Results represent three separate experiments (A) and the mean±S.D. of measurements (four mice/group; B). *, $p<0.05$; **, $p<0.01$.

This example describes how Slit-Robo signaling regulates β-catenin and Wnt targeting genes. The in vivo effects of Slit-Robo signaling on the cellular localization of β-catenin and the expression of Wnt targeting genes in the small intestine was next examined. When the cytoplasmic and nuclear fractions of the mouse small intestinal crypts were separated, it was found that Robo1/2 double heterozygotes and R5-treated Wt mice had decreased β-catenin in their cytoplasmic and nuclear fractions, as compared to Wt mice with or without mIgG treatment (FIG. 20A, upper panel). In contrast, Slit2-Tg mice displayed increased β-catenin in their cytoplasmic and nuclear fractions. Immunoblotting of β-tubulin (a marker for the cytoplasm) and Sp1 (a marker for the nucleus; FIG. 20A, lower panels) served as controls. The findings of inactivation of β-catenin and suppression of canonical Wnt targeting genes in Robo1/2 double heterozygotes and R5-treated C57 mice are reminiscent of previous observations in mice lacking Tcf-4 (see, e.g., Korinek, V., et al., (1998) Nat. Genet. 19, 379-383) or ectopically expressing Dickkopf1 (Dkk1), a secreted Wnt inhibitor (see, e.g., Pinto, D., et al., (2003) Genes. Dev. 17, 1709-1713; Kuhnert, F., et al., (2004) PNAS 101, 266-271).

Figure 21:
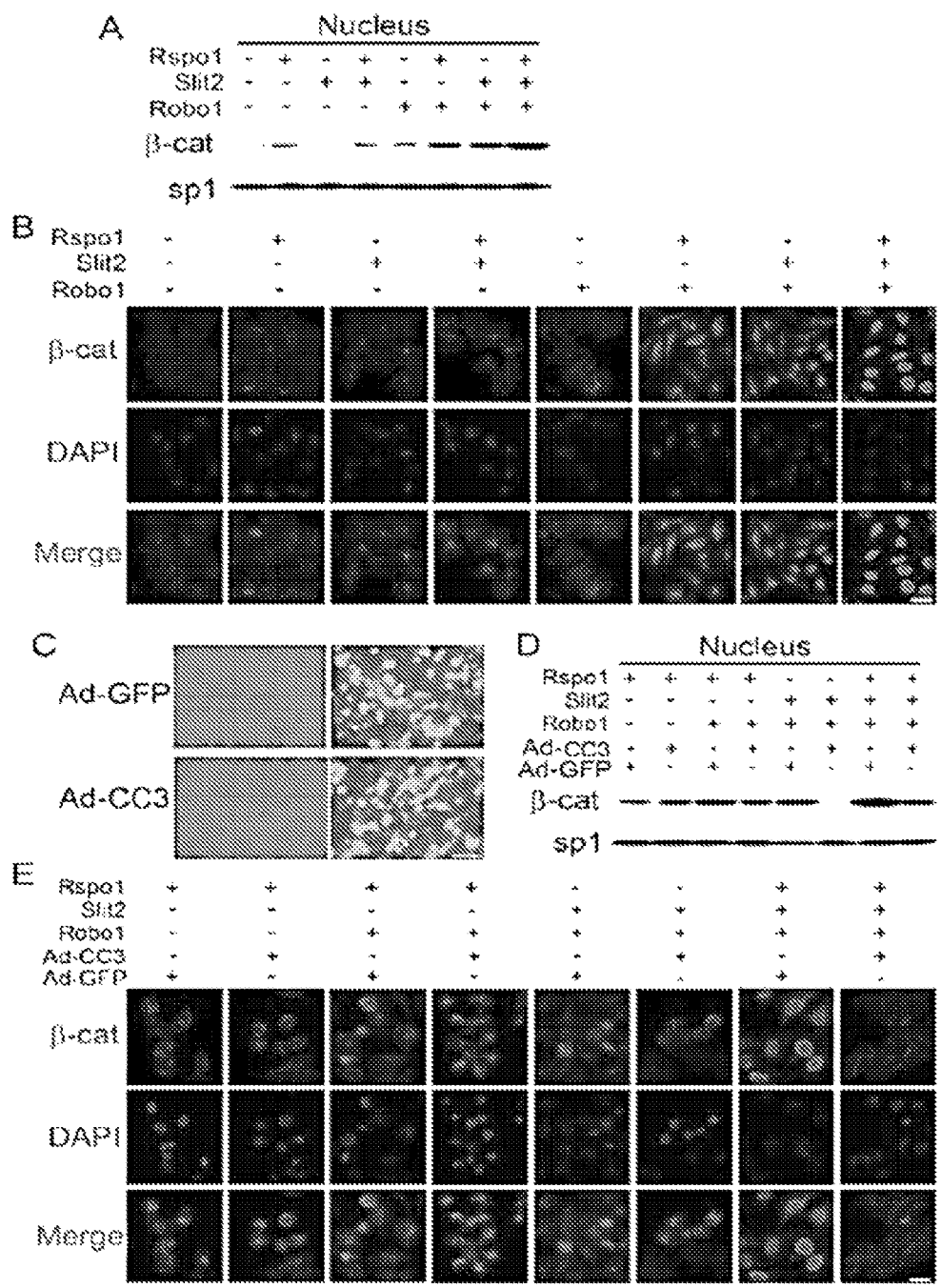
FIG. 21 describes how Slit-Robo signaling potentiates Rspo1-induce β-catenin activation. (A and B) Induction of β-catenin cytoplasmic and nuclear translocation by Slit2 and Rspo1. 293 cells were transfected with the Robo1 plasmid and incubated with rRspo1 and/or rSlit2 (both at 0.5 μg/ml) for 4 hours. The cell lysates were fractionated and the cytoplasmic fraction was immunoblotted for β-catenin and Sp1 (A). Alternatively, they were stained for β-catenin and DAPI, observed under a laser scanning confocal microscope, and the recorded fluorescent images were merged (B). (C) Expression of adenoviral GFP and CC3. 293 cells were infected with Ad-GFP or Ad-CC3 (both at $1 \times 10^8$ PFU/well) for 2-3 days, prior to observation under a laser scanning confocal microscope. (D and E) CC3 inhibits β-catenin cytoplasmic and nuclear translocation elicited by Slit2 and Rspo1. 293 cells were transfected with the Robo1 plasmid and infected with Ad-GFP or Ad-CC3. They were then incubated with rRspo1 and/or rSlit2 (both at 0.5 μg/ml) for 4 hours. The cell lysates were fractionated and the cytoplasmic fraction was immunoblotted for β-catenin and Sp1 (D). Alternatively, they were stained for β-catenin and DAPI, observed under a laser scanning confocal microscope, and the recorded fluorescent images were merged (D). Results are representatives of more than three separate experiments. Bars, 20 μm.

To test whether Slit-Robo signaling activates β-catenin, the protein expression of Wnt targeting genes, such as c-Myc, ephB2 and ephB3, were determined. As predicted, they were down-regulated in the intestines of Robo1/2 double heterozygotes and R5-treated mice when compared to their Wt counterparts, with or without mIgG treatment (FIG. 20B). In contrast, they were up-regulated in the intestine of Slit2-Tg mice. As the Wnt targeting genes Cdx1 and 2 critically contribute to intestinal specification (see, e.g., Beck, F., and Stringer, E. J. (2010). Biochem. Soc. Trans. 38, 353-357), their mRNA expression was measured. Compared to Wt mice, the expression of Cdx1 and 2 mRNAs was compromised in the small intestine of Robo1$^{-/+}$/2$^{-/+}$ mice (FIG. 20C). In contrast, the expression of Cdx1 and 2 mRNAs was drastically enhanced in the Slit2-Tg counterparts. R5, but not mIgG, also mitigated the expression of Cdx1 and 2 mRNAs. Consistently, rRspo1 elicited β-catenin translocation in 293 cells, whereas rSlit2 acted synergistically with rRspo1 for β-catenin translocation in Robo1-expressing 293 cells (FIGS. 21A and B). Compare to Ad-GFP, overexpression of Ad-CC3 (FIG. 21C) also inhibited rRspo1 and/or rSlit2-induced β-catenin translocation in the Robo1-expressing 293 cells. (FIGS. 21D and E). In addition, Ad-β-catenin, but not Ad-GFP, rescued the phenotype in Robo1/2 double heterozygotes for development of intestinal organoids (FIG. 19L). These data collectively indicate that the interaction of the cytoplasmic CC3 motif of Robo1 with the carboxyl portion of cytoplasmic LRP6 induces LRP6 phosphorylation, β-catenin translocation and the TCF/LEF promoter activation, downstream of Slit2-Robo1 and Rspo1-Robo1 signaling pathways, for activation of canonical Wnt signaling during physiologic maintenance of intestinal homeostasis.

Example 9

Figure 22:
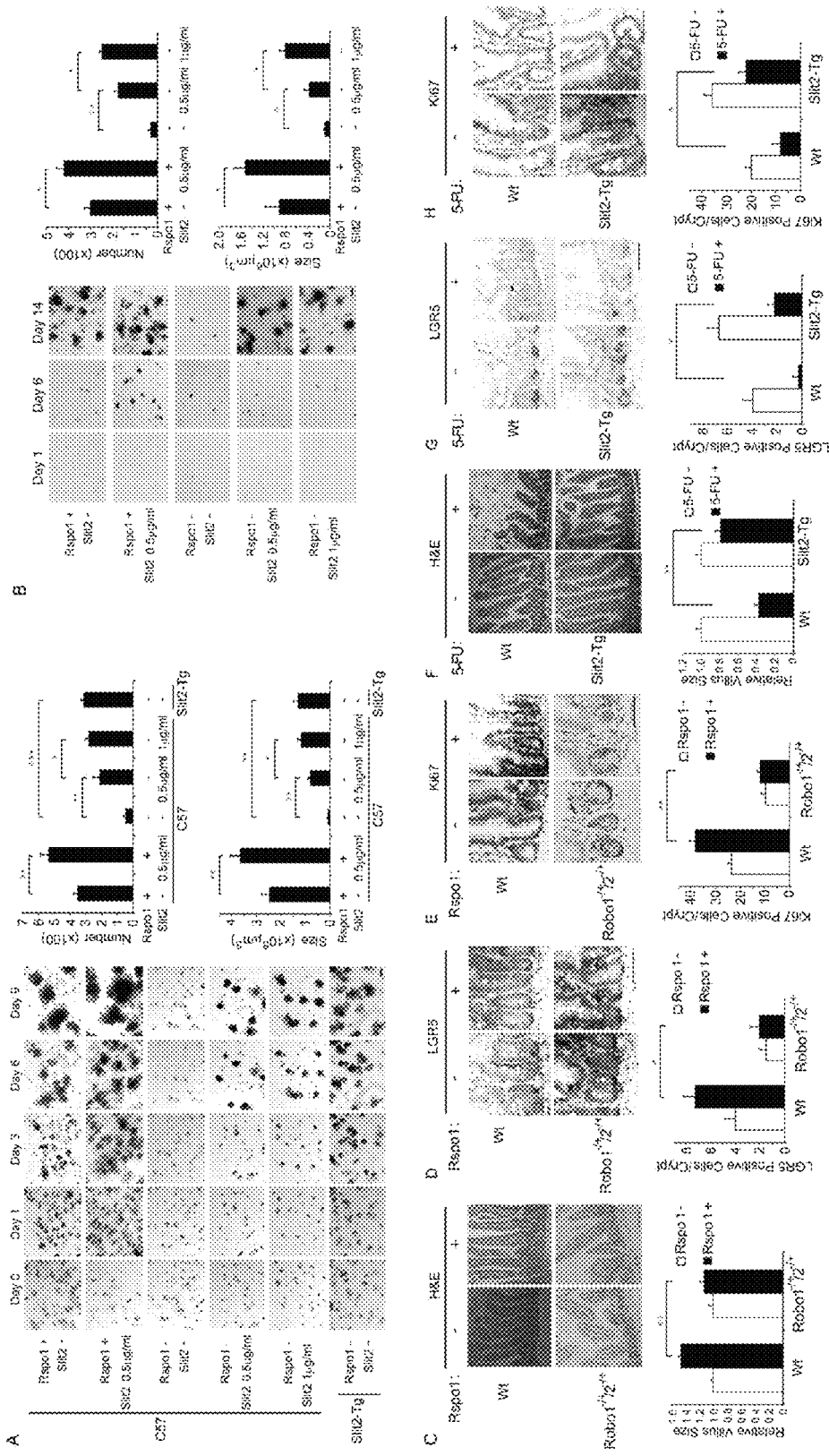
FIG. 22 describes how Slit2 potentiates Rspo1 for induction of intestinal organoids and Robo1 acts as an indispensible receptor for Rspo1 during intestinal repair (A and B) Slit2 acts with Rspo1 for promoting intestinal organoids. The intestinal crypts (A) and LGR5-positive ISCs (B) were isolated from C57, Slit2-Tg and LGR5-GFP mice and were cultured in vitro in the presence of rRspo1, rRspo1 plus rSlit2, in the absence of rRspo1, in the absence of rRspo1 but in the presence of rSlit2, or in the absence of both rRspo1 and rSlit2. The numbers and sizes of intestinal organoids were measured. (C-E) Rspo1 fails to promote growth of intestinal villi in Robo1$^{-/+}$/2$^{-/+}$ mice. rRspo1 (0.1 mg/mouse) was given through the tail veins to Wt and Robo1$^{-/+}$/2$^{-/+}$ mice daily for 6 consecutive days. Mice were sacrificed at day 7 and the intestinal tissues harvested were H&E stained for determination of the relative villus sizes (C) and immunohistochemically stained for measurement of the numbers of LGR5-positive ISCs (D) and Ki67-positive TA cells (E). (F-H) The Slit2-Tg intestines are less vulnerable to chemotherapy. C57 and Slit2-Tg mice were treated daily by intraperitoneal administration of a therapeutic dose of 5-FU (30 mg/kg/mouse/day for 5 days). 3 days later, mice were sacrificed and the intestinal tissues were H&E stained for determination of the relative villus sizes (F) and immunohistochemically stained for measurement of the numbers of LGR5-positive ISCs (G) and Ki67-positive TA cells (H). Results represent at least three separate experiments (A and B) or are the mean±S.D. of measurements of 10 tissue sections/mouse (4-5 mice/group; C-H). Bars, 200 μm for A and B and 50 μm for C-H. *, $p<0.05$; , $p<0.01$; *, $p<0.001$.

This example describes how Slit2 potentiates Rspo1 for induction of intestinal organoids and promotion of intestinal regeneration. It was next tested whether Slit2 could potentiate Rspo1 for inducing intestinal organoids in vitro. As predicted, rSlit2 acted synergistically with rRspo1 to promote in vitro formation and growth of intestinal organoids in terms of both of their number and size (FIG. 22A). In the absence of rRspo1, rSlit2 alone, at 0.5 or 1 μg/ml, was capable of inducing intestinal organoids. The intestinal crypts isolated from Slit2-Tg mice (see, e.g., Yang, X. M., et al., (2010) Biochem. Biophys. Res. Commun. 396, 571-577; Ye, B. Q., et al., (2010) J. Immunol. 185, 6294-6305; Han, H. X., and Geng, J.-G. (2011) Acta Pharmacol. Sin. 32, 1327-1336; Guo, S. W., et al., 2012 Reprod. Sci. [Epub ahead of print]) also formed intestinal organoids without added rRspo1 or rSlit2. Using single cell sorting gated for GFP (see, e.g., Sato, T., et al., (2009) Nature 459, 262-265), ISCs were isolated from LGR5-GFP mice and found that rSlit2 alone could induce intestinal organoids (FIG. 22B). These results indicate that Slit2 alone, in analogous to Rspo1, potently induces intestinal organoids. More importantly, Slit2 acts cooperatively with Rspo1 in development and maintenance of intestinal organoids in vitro.

The functional significance of Robo1 in Rspo1-induced intestinal repair in vivo was next further tested. Consistent with previous reports (see, e.g., Kim, K. A., et al., (2005) Science 309, 1256-1259; Zhao, J., et al., (2009) Proc. Natl. Acad. Sci. USA 106, 2331-2336; Zhao, J., et al., (2007) Gastroenterology 132, 1331-1343; Bhanja, P., et al., (2009) PLoS One 4, e8014; Takashima, S., et al., (2011) J. Exp. Med. 208, 285-294; de Lau, W., et al., (2011) Nature 476, 293-297), intravenous administration of rRspo1 potently promoted growth of intestinal epithelial cells in Wt mice, as determined by the extended villus length (FIG. 22C). Surprisingly, rRspo1 failed to accelerate growth of intestinal epithelial cells in Robo1/2 double heterozygotes. Compared to their Wt counterparts, rRspo1 also failed to significantly augment the numbers of LGR5-positive ISCs (FIG. 22D) and Ki67-positive proliferating TA cells (FIG. 22E) in the intestinal crypts of Robo1$^{-/+}$/2$^{-/+}$ mice. Furthermore, it was found that the therapeutic dosage of 5-FU, a well-characterized chemotherapy medicine, drastically shortened the villus length (FIG. 22F) and reduced the numbers of LGR5-positive ISCs (FIG. 22G) and Ki67-positive proliferating TA cells (FIG. 22H) in C57 mice, but not in Slit2-Tg mice. These findings argue that Robo1, expressed on ISCs and TA cells at the intestinal crypt, is a cognate receptor for Rspo1 during intestinal repair.

Example 10

This example describes how Slit2 cooperates with Rspo1 for reduction of chemoradiation-induced death. Stimulation of Wnt/β-catenin signaling with Rspo1 can ameliorate 5-fluorouracil (5-FU) and radiation-induced gut damage, including radiation-induced gastrointestinal syndrome (RIGS) (see, e.g., Kim, K. A., et al., (2005) Science 309, 1256-1259; Zhao, J., et al., (2009) Proc. Natl. Acad. Sci. USA 106, 2331-2336; Bhanja, P., et al., (2009) PLoS One 4, e8014; Takashima, S., et al., (2011) J. Exp. Med. 208, 285-294). As Slit2 potentiated Rspo1-mediated canonical Wnt signaling and mitigated chemotherapy-induced gut injury, it was asked whether Slit2, in combination with Rspo1, could prolong overall survival of mice receiving lethal challenges of chemoradiation. It was found that mice with the Slit2 transgene there was a 70% survival rate in mice receiving a lethal dose of 5-FU, whereas this same dose (see, e.g., Martine, D. S., et al., (1982) Cancer Res. 42, 3964-3970) caused the death of all Wt mice within two weeks (FIG. 23A).

Because aberrant Wnt signaling due to loss and/or mutation of Wnt signaling pathway components causally contribute to carcinogenesis (see, e.g., Clevers and Nusse, (2012) Cell 149, 1192-1205) and because recurrent gene fusion of Rspo2 and 3 directly contributes to the etiology of colorectal cancer (see, e.g., Seshagiri, S., et al., (2012) Nature 488, 660-664), whether a short 3-day pulse of rSlit2 and/or rRspo1 could accelerate the development of intestinal carcinogenesis or decrease its sensitivity to chemoradiotherapy was explored. To test this, Apc$^{MIN/+}$ mice with spontaneous intestinal adenoma were treated with dextran sulfate sodium (DSS) to induce inflammation related intestinal carcinogenesis, a murine model that is thought to closely mimic multi-factorial human colorectal cancer (see, e.g., Phutthaphadoong, S., et al., (2010) Oncol. Rep. 23, 53-59). Treatment of DSS-treated Apc$^{MIN/+}$ mice with rSlit2 or rRspo1 alone led to a 20-30% survival rate (FIG. 23B). Given a combination of rSlit2 and rRspo1 led to a 60% survival rate (p=0.0023 between the rRspo1 plus rSlit2 group and the rRspo1 group or the rSlit2 group), showing to the significance of functional cooperation between Slit2 and Rspo1 for increasing host tolerance to the lethal dosage of chemotherapy in the murine model of carcinogenesis.

Consistent with previous reports using recombinant flagellin in xenografted mouse sarcoma and malignant melanoma (see, e.g., Burdelya, L. G., et al., (2008) Science 320, 226-230) and adenoviral Rspo1 in xenografted human colorectal carcinoma (see, e.g., Bhanja, P., et al., (2009) PLoS One 4, e8014), no acceleration of intestinal cancer development and desensitization to 5-FU chemotherapy was detected with our rRspo1 and rSlit2 combination treatment (FIG. 23C). In contrast, upon administration of rRspo1 and rSlit2, a single "lethal" dose of 5-FU drastically eliminated the number of intestinal tumors, suggesting that Rspo1 plus Slit2 treatment may act as adjuvants before, during or after intensive chemotherapy for cancer eradication.

Figure 23:
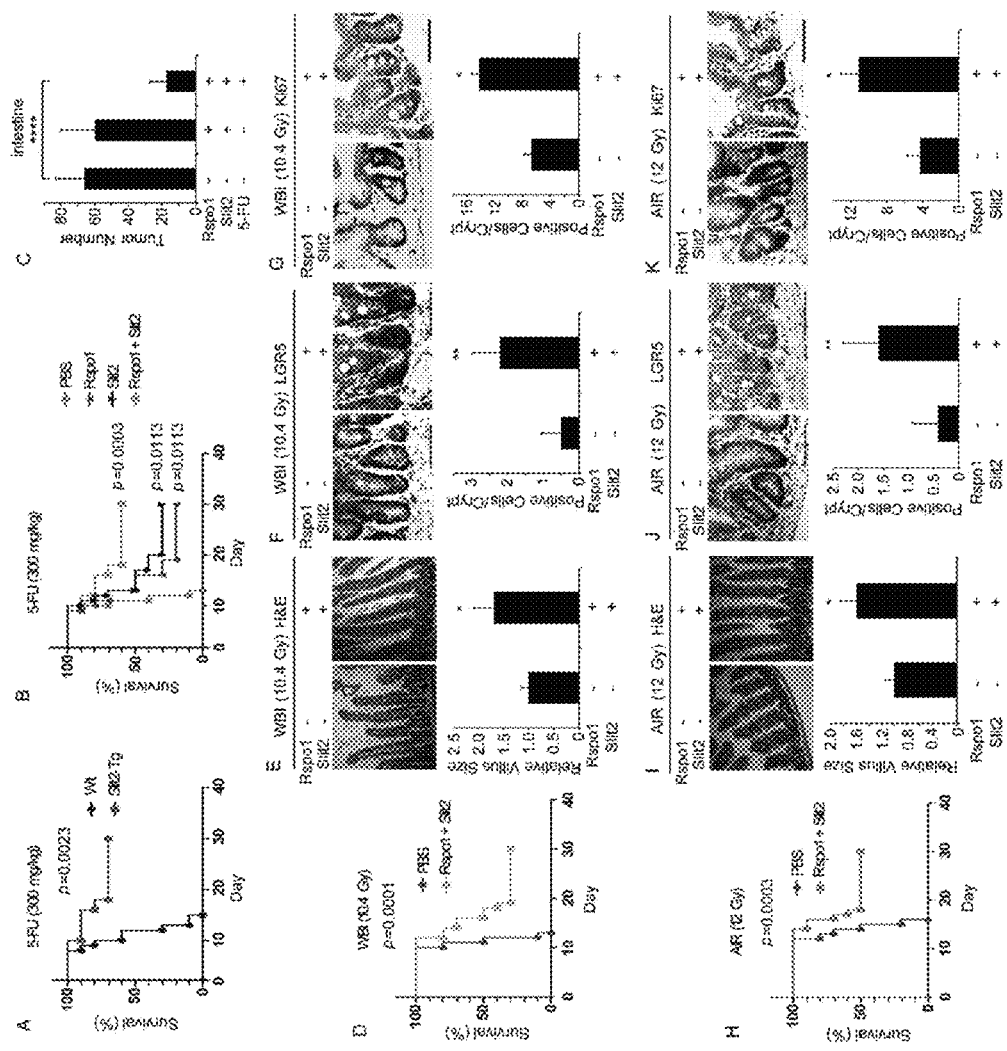
FIG. 23 describes how Slit2 and Rspo1 cooperatively induce ISCs, reduce intestinal damage and prolong overall survival following intensive chemoradiotherapy (A) Slit2 transgene increases resistance to 5-FU. A single lethal dosage of 5-FU (300 mg/kg) was given to Wt and Slit2-Tg mice (10 mice/group) and the death rates were recorded. (B and C) Slit2 plus Rspo1 prolongs overall survival in tumor-bearing mice. rSlit2 or rRspo1 alone or in combination (0.1 mg/mouse/day for 3 days) were intravenously given to DSS-treated Apc$^{MIN/+}$ mice (10 mice/group). On day 2 of rSlit2 plus rRspo1 treatment, a single lethal dose of 5-FU was given and the death rates were recorded (B). The tumor numbers in the small intestine were also counted (C). (D-K) Slit2 plus Rspo1 decreases radiation-induced death. Wt mice were given intravenously a regiment of rSlit2 plus rRspo1 (0.1 mg/mouse/day for 3 days; 12 mice/group). On day 2 after these treatments, they were irradiated (10.4 Gy/mouse once for WBI or 12 Gy/mouse once for AIR) and the death rates were recorded (D and H). The villus sizes (E and I), the numbers of LGR5-positive cells (F and J), and Ki-67-positive cells (G and K) were also determined. Results are derived from 10 mice/group (A-D and H) or the mean±S.D. of measurements of 10 tissue sections/mouse (E-G and I-K). Kaplan-Meier survival curves were constructed and analyzed by a log rank test (A, B, D and H). Bars, 50 μm. *, $p<0.05$; , $p<0.01$; **, $p<0.0001$.

Furthermore, the combination of rSlit2 plus rRspo1 led to a 30% survival rate in mice receiving a lethal dose of whole body irradiation (WBI) (FIG. 23D) and a 50% survival rate in mice receiving a lethal dose of abdominal irradiation (AIR) (FIG. 23H). Concomitant prolongations of the villus length (FIGS. 23E and I), augmentations of LGR5-positive ISCs (FIGS. 23F and J) and Ki67-positive proliferating TA cells (FIGS. 23G and K) was also observed, which are consistent with previous finding that LGR5-positive ISCs in small intestine are resistant to radiation (see, e.g., Hua, G., et al., (2012) Gastroenterology 143, 1266-1276). Taken together, our data provide in vivo evidence that the binding of Rspo1 and Slit2 to Robo1 synergistically activates Wnt/β-catenin signaling, cooperatively induces ISCs for intestinal homeostasis and repair, and significantly prolongs overall survival following lethal doses of chemoradiotherapy.

Example 11

This example describes the experimental procedures for Examples 1-10.

Mouse Experiments and Histology

C57BL6/J (Wt; Stock No. 005304), LGR5-EGFP-IRES-creERT2 (LGR5-GFP; Stock No. 008875) (see, e.g., Barker et al., 2007 Nature 449, 1003-1007), and Apc$^{MIN/+}$ (Stock No. 002020) mice were purchased from Jackson Laboratory. Robo1$^{-/+}$/2$^{-/+}$ mice (see, e.g., Grieshammer et al., 2004 Dev. Cell 6, 709-717; Long et al., 2004 Neuron 42, 213-223) were purchased from MMRRC/University of Missouri and their wild-type littermates (Wt) were used as the control mice. Slit2-Tg mice were generated and characterized (see, e.g., Guo, S. W., et al., 2012) Reprod. Sci. [Epub ahead of print]; Yang et al., 2010 Biochem. Biophys. Res. Commun. 396, 571-577; Ye et al., 2010 J. Immunol. 185, 6294-6305; Han and Geng, 2011 Acta Pharmacol. Sin. 32, 1327-1336). For measurement of cell proliferation, Wt and Slit2-Tg mice were injected with BrdU (1 mg/100 grams of body weight) for 2 h prior to sacrifice. For antibody treatment, Wt mice (10 weeks old) were intraperitoneally given 1 mg isotype-matched irrelevant mIgG or R5 for 6 consecutive days. For "rescue" experiments, recombinant Rspo1 (0.1 mg/mouse/day for 5 days) was given to Wt and Robo1$^{-/+}$/2$^{-/+}$ mice (10 weeks old) through the tail veins. For induction of inflammation-related intestinal carcinogenesis, Apc$^{MIN/+}$ mice were treated with 2% DSS in drinking water for one week and used two weeks later (see, e.g., Phutthaphadoong et al., 2010 Oncol. Rep. 23, 53-59). For "chemoradiation" experiments, Wt and DSS-treated Apc$^{MIN/+}$ mice (10 weeks old) were intravenously given Slit2 or Rspo1 alone or in combination (0.1 mg/mouse/day for 3 days). On day 2, they were intraperitoneally given 5-FU (30 mg/kg/mouse/day for 5 days for the therapeutic dosage or 300 mg/kg once for the lethal high dosage) or irradiation (10.4 Gy/mouse once for WBI or 12 Gy/mouse once for AIR) (Martin et al., 1982; Kim et al., 2005; Bhanja et al., 2009). Alternatively, Slit2-Tg mice (10 weeks old) were intraperitoneally given 5-FU (30 mg/kg/mouse/day for 5 days or 300 mg/kg once). Tissue sections of small intestines were stained with hematoxylin & eosin (H&E) and the relative villus sizes and number at the duodenum, jejunum and ileum were double-blindly measured. The length ratios of 1:3:2 of the entire small intestine were defined as the duodenum, jejunum and ileum, respectively (see, e.g., Duan et al., 2004 J. Lipid Res. 45, 1312-1323).

Fluorescent In Situ Hybridization

The cDNA segments of mouse Slit2 (base pair 3960-4566), mouse Robo1 (base pair 3443-4956) and mouse Robo2 (base pair 2328-4527) were reverse transcribed and labeled with digoxigenin (DIG) or biotin according to the manufacturer's instructions (Roche). Intestinal tissues were fixed with 4% paraformaldehyde and tissue sections (5-μm thick) were incubated with 1 μg/ml linearized DIG- or biotin-labeled antisense and sense RNA probe (Yang et al., 2008). For immunofluorescent staining, Western Blocking Reagent (Roche) was diluted in a 1 to 10 dilution with 20 mM Tris-HCl, pH 7.4, containing 0.1% Tween 20 (TBST) for blocking slides and diluting all antibodies, including 1:1000 dilution of sheep anti-DIG Ab (Roche) or mouse anti-biotin mAb (Jackson ImmunoResearch), and 1:200 dilution of HRP-conjugated rabbit anti-sheep Ab (Jackson ImmunoResearch). Tyramide Signal Amplification Kits (488 or 555, Invitrogen) were used according to the manufacturer's protocol.

Immunofluorescent and Immunohistochemical Staining

Intestinal tissues were fixed with 4% paraformaldehyde, sectioned (5-μm thick) and permeabilized with 0.05% Triton X-100 in phosphate buffered saline, pH 7.4 (PBS). Samples were blocked with 1% bovine serum albumin (BSA; Sigma) and incubated with primary Ab at 37° C. for 1 h, including Abs against Ki67, LGR5 and lysozyme (abcam), villin and β-catenin (BD Biosciences), c-myc (Santa Cruz Biotechnology), GFP (Novus Biologicals), and pan-Slit and Robo1 (S1 and R4; Wang et al., 2003 Cancer Cell 4, 19-29; Zhou et al., 2011 Cell Res. 21, 609-626). After washing extensively, samples were incubated with appropriate fluorescent dye- or HRP-conjugated secondary Ab at 37° C. for 1 h. Sections were counterstained with 4',6-diamidino-2-phenylindole (DAPI) or H&E. Slides were then washed and mounted for observation under a scanning confocal microscope (Leica TCS SP2) or a fluorescence stereomicroscope (Leica M205 FA). The immunohistochemical staining of LGR5 and Ki67 from ten random microscopy fields of intestinal sections per mouse and three or four mice per group were also calculated double blindly by ImageTool Software.

Intestinal Crypt Culture

The intestinal crypts of mouse small intestines were isolated (see, e.g., Booth, C., et al., (1999) Exp. Cell Res. 249, 359-366). They were in vitro cultured (see, e.g., Spence et al., 2011 Nature. 470, 105-109) in the presence of rRspo1 (0.5 µg/ml; FIG. 17B), EGF (0.1 µg/ml; R&D Systems), noggin (0.1 µg/ml; FIG. 17A) and/or rSlit2 (0.5 or 1 µg/ml as indicated). They were infected with $1 \times 10^8$ PFU/ml Ad-GFP (Cat. No. 1766, Vector Biolabs), Ad-β-catenin fused with GFP (Cat. No. 1182, Vector Biolabs) or Ad-CC3 fused with GFP (custom-made by Vector Biolabs). Isolation and cell sorting of GFP-positive ISCs expressing LGR5-EGFP was performed (see, e.g., Sato et al., 2009 Nature 459, 262-265).

qRT-PCR

All mouse $RT^2$ qPCR primer pairs were purchased from SA Biosciences. The crypts of mouse small intestine were isolated (see, e.g., Booth, C., et al., (1999) Exp. Cell Res. 249, 359-366) for qRT-PCR as previously described (Zhou et al., 2011 Cell Res. 21, 609-626).

Immunoblotting, Immunoprecipitation and Pulldown Assay

For sub-cellular fractionation, membrane, cytoplasmic and nuclear extracts from the isolated intestinal crypts and 293 cells were prepared using Qproteome Cell Compartment Kit (Qiagen). Alternatively, 293 cells, either un-transfected, transfected with the plasmids of Robo1 or LRP6, or infected with Ad-CC3, were incubated with Rspo1 and/or Slit2 (both at 0.5 µg/ml) for 4 hours. Following washing with ice-cold phosphate buffered saline, pH 7.4 (PBS), they were lysed with ice-cold radioimmunoprecipitation assay lysis buffer [50 mM Tris-HCl, pH 7.4, 150 mM NaCl, 1 mM sodium orthovanadate 10 mM sodium fluoride, 1 mM phenylmethylsulfonyl fluoride, 2 µg/ml aprotinin, 2 µg/ml leupeptin, 1 µg/ml pepstatin A, 15 µg/ml benzamidine, 0.5% Nonidet P-40, 0.15% bovine serum albumin (BSA) and 10% glycerol] at 4° C. for 1 h. Samples were centrifuged at 12,000 g for 15 min at 4° C. Samples were subjected to SDS-PAGE, transferred to PVDF membranes (EMD Millipore) and detected with appropriate primary Abs followed by horseradish peroxidase-conjugated goat anti-mouse or rabbit immunoglobulin G (IgG). The blotting signals were detected using SuperSignal West Dura Extended Duration Substrate (Pierce; Rockford, Ill.). Quantitative analyses of immunoblotting signals on Fuji Films were obtained by densitometry analysis using LAS4000 Image Software.

For immunoprecipitation, 1 µg of the appropriate antibody was preincubated with 30 µl slurry of Protein A Sepharose CL-4B beads (GE Healthcare Biosciences; Piscataway, N.J.). Lysates (~1 mg/sample) were incubated with antibody-bound Protein A beads at 4° C. overnight. After extensive washing with the radioimmunoprecipitation assay lysis buffer, samples were resuspended in the reducing SDS sample loading buffer, boiled for 5 min, and subjected to SDS-PAGE followed by immunoblotting.

For the pulldown assay, 3 µg of the appropriate purified GST-tagged fusion protein and isolated His-tagged fusion protein were incubated with 20 µl glutathione Sepharose beads (GE Healthcare Biosciences) in PBS containing 1% BSA at 4° C. for 2 h. After extensive washing, samples were suspended in the reducing SDS sample loading buffer, boiled for 5 min, and subjected to SDS-PAGE followed by immunoblotting. The primary Abs against LRP6, $pS^{1490}$ LRP6 and β-catenin (Cell Signaling Technology), 6-His, Sp1, GST and flag (Sigma), LGR5 and HA (abcam), c-Myc (Santa Cruz Biotechnology), myc (9E10; American Type Culture Collection), Rspo1 (Thermo Scientific), α-tubulin, EphB2 and 3 (R&D Systems) and β-actin (BD Biosciences) were used.

Plasmid Construction and Recombinant Protein Expression

The mammalian expressing plasmids of Robo1, Robo1-FN, Robo1-Ig and Robo1-dCC3 fused with HA tags were kindly provided (see, e.g., Wong et al., 2001 Cell 107, 209-221). The human LRP6 cDNA (Open Biosystems) was amplified, using the forward primer 5'-AAAGGATC-CAATGGGGGCCGTCCTGAGGAGCCTCCTGG-3' (SEQ ID NO: 1) and the reverse primer 5'-AAAGTCGACTCA-GGAGGAGTCTGTACAGGGAGAGGGTGGCGGTGG-3' (SEQ ID NO: 2). The amplified insert was digested with BamHI/SalI and ligated to pCMV3Tag2C (Invitrogen) for the expression plasmid of LRP6 fused with a myc tag. The human LGR5 cDNA (Open Biosystems) was amplified, using the forward primer. 5'-AAGGATCCATGGACAC-CTCCCGGCTCGGTGTGCTCCT-3' (SEQ ID NO: 3) and the reverse primer 5'-GGCTCGAGGAGACATGGGA-CAAATGCCACAGAGGAAAGATGGC-3' (SEQ ID NO: 4). The amplified insert was digested with BamHI/XhoI and ligated to pCMVTag4A (Invitrogen) for the expression plasmid of LGR5 fused with a flag tag.

Using the plasmid of wild-type human Robo1, Rspo1 and LRP6 as the templates, the forward primer 5'-AAAGGATC-CATGAAATGGAAACATGTTCCTTTTTTGGTC-3' (SEQ ID NO: 5) and the reverse primer 5'-AAACTCGAGTCAT-GCATTGTGGCTCACAGCCTC-3' (SEQ ID NO: 6) for the extracellular Ig1 domain of Robo1 fused with GST (GST-Ig1); the forward primer 5'-AAAGGATCCTCGCTG-GAAGTAGCCATACTTCGG-3' (SEQ ID NO: 7) and the reverse primer 5'-AAACTCGAGTCAAGTCAGCTCGGC-TACTTCACTCTC-3' (SEQ ID NO: 8) for the extracellular Ig2 domain of Robo1 fused with GST (GST-Ig2); the forward primer 5'-AAAGGATCCGTCTTAGAGAGAC-CATCATTTGTGAAGAGACC-3' (SEQ ID NO: 9) and the reverse primer 5'-AAACTCGAGTCAAACAGTCAGAG-TAGCAGATGCTTCAGC-3' (SEQ ID NO: 10) for the extracellular Ig3 domain of Robo1 fused with GST (GST-Ig3); the forward primer 5'-AAAGGATCCCAAGAAC-CTCCACATTTTGTTGTGAAAC C-3' (SEQ ID NO: 11) and the reverse primer 5'-AAACTCGAGTCATCCAG-CAACATTTAAAGTCTGGCAGAT-3' (SEQ ID NO: 12) for the extracellular Ig4 domain of Robo1 fused with GST (GST-Ig4); the forward primer 5'-AAAGGATCCAGCAT-CATCACAAAGGCATATTTGGAAGTTAC-3' (SEQ ID NO: 13) and the reverse primer 5'-AAACTCGAGTCACT-GAACTGGAACTCCAAATTCTTGAACTTC-3' (SEQ ID NO: 14) for the extracellular Ig5 domain of Robo1 fused with GST (GST-Ig5); the forward primer 5'-AAAGGATC-CATGCGCCGGGATAAAGAACGCC AGGCCAAAC-3' (SEQ ID NO: 15) and the reverse primer 5'-AAACTCGAG-GTCATCACCTCCACCATACATG TCAGCAAG-3' (SEQ ID NO: 16) were used to amplify the cytoplasmic CC0/1 motif of Robo1 (CC0/1); the forward primer 5'-ATTG-GATCCGGATCCTACAACAGCTCAGACCGGGGCAG-3' (SEQ ID NO: 17) and the reverse primer 5'-ATTCTC-GAGCTAGCCAGCAGCATCCTGCATTTGCCGTC-3' (SEQ ID NO: 18) for the cytoplasmic CC2 motif of Robo1 (CC2); the forward primer 5'-ATTGGATCCCGTCGA-CATTTTCATGCGTCTC-3' (SEQ ID NO: 19) and the reverse primer 5'-CCGCTCGAGTCAGCTTTCAGTTTC-CTCTAATTCTTCATTATTATC-3' (SEQ ID NO: 20) for the cytoplasmic CC3 motif of Robo1 (CC3); the forward primer 5'-AAAGGATCCATGCGGCTTGGGCTGTGTGTG-GTGGC-3' (SEQ ID NO: 21) and the reverse primer 5'-AAACTCGAGCAGCATGGTGCCATTGGCAGCTGAG-GAGCC-3' (SEQ ID NO: 22) for the amino segment of Rspo1 containing two furin repeats (Rspo1-N); the forward primer 5'-CCCGGATCCATGGAGTGCAGTAGTCCT-GCGCAATGTGAAATG-3' (SEQ ID NO: 23) and the reverse primer 5'-AAACTCGAGGGCAGGCCCTGCA-GATGTGAGTGGCCC-3' (SEQ ID NO: 24) for the carboxyl-terminus of Rspo1 containing one TSR repeat (Rspo1-C); the forward primer 5'-AAAGGATCCTACTT-TATCTGCCAGAGGATGTTGTGTCCAC-3' (SEQ ID NO: 25) and the reverse primer 5'-AAACTCGAGTCAAGA-CATTCCTGGAAGAGATCCTGACAAAG-3' (SEQ ID NO: 26) for the LRP6 M1 mutant fused with GST (GST-M1); the forward primer 5'-AAAGGATCCTATGAC-CGAGCCCATGTTACAGGAGCATCATCA-3' (SEQ ID NO: 27) and the reverse primer 5'-AAACTCGAGTCAGCT-GCAGGGTGTGGTGGGGG-3' (SEQ ID NO: 28) for the LRP6 M2 mutant fused with GST (GST-M2); and the forward primer 5'-AAAGGATCCACAGATGTTTGT-GACAGTGACTATGCTCCTAGT CGG-3' (SEQ ID NO: 29) and the reverse primer 5'-AAACTCGAGTCAGGAG-GAGTCTGTACAGGGAGAGGG TGGC-3' (SEQ ID NO: 30) for the LRP6 M3 mutant fused with GST (GST-M3). The amplified inserts were digested with BamH1/Xho1 and ligated to the PETM vector (GE Healthcare Life Sciences) for His-fusion proteins and to the PGEX6P1 vector (GE Healthcare Life Sciences) for GST-fusion proteins. All constructs were verified by DNA sequence analysis. They were expressed and purified as published before (see, e.g., Wang et al., 2007 Nat. Immunol. 8, 882-892).

Baculovirus Expression of Rspo1, Noggin and Robo1-Fc

The cDNAs of human Rspo1 and noggin (Open Biosystems) were amplified for construction of 6-His fusion proteins, using the forward primer 5'-TTGCGGCCGCATGCG-GCTTGGGCTGTG-3' (SEQ ID NO: 31) and the reverse primer 5'-GGGAATTCGGCAGGCCCTGCAGATGT-GAGTGGCC-3' (SEQ ID NO: 32) for Rspo1; and the forward primer 5'-TAGCGGCCGCATGGAGCGCTGC-CCC-3' (SEQ ID NO: 33) and the reverse primer 5'-GGGAATTCGCACGAGCACTTGCACTCGGAAT-GATGG-3' (SEQ ID NO: 34) for noggin. The inserts of Rspo1 and noggin were digested with NotI/EcoRI. They were ligated into the pVL1392 vector (BD Pharmingen).

For construction of the plasmid of Robo1-Fc, the pAc-k-CH3 plasmid that harbors the constant regions of a human immunoglobulin gene (US Biological) was used to amplify the carboxyl-terminus of human immunoglobulin heavy chain, using the forward primer 5'-AACCGTGCGGC-CGCTGTTGTGACAAAACTCACAC-3' (SEQ ID NO: 35) and the reverse primer 5'-CGCGGAGATCTTCATTTAC-CCGGAGACAGGGAGAGGC-3' (SEQ ID NO: 36). The PCR product was cleaved with NotI/BglII and ligated the pVL1393 vector (BD Pharmingen) for the plasmid of pVL1393-Fc. The human Robo1 cDNA clone (Origene) was used to amplify the extracellular five Ig domains (1-1621 bp), using the forward primer 5'-GGCGGCCTCTAGAAT-GAAATGGAAACATGTTCC-3' (SEQ ID NO: 37) and the reverse primer 5'-CTATAAGCGGCCGCCAATG-TAAGCACTCCATGTT-3' (SEQ ID NO: 38). The PCR product was cleaved with XbaI/NotI and ligated to pVL1393-hFc for pVL1393-Robo1-Fc. The construct was verified by DNA sequence analysis.

Rspo1, noggin and Robo1-Fc were expressed in Sf9 insect cells using a baculovirus expression system (Baculo-Gold; BD Pharmingen) and purified to homogeneity from the serum-free supernatant of Sf9 cells infected with their respective viral stocks (MOI ~2×10$^8$/ml) by Talon metal affinity chromatography (BD Clontech) or Protein A affinity chromatography (GE Healthcare Life Sciences). Endotoxin levels of these isolated recombinant proteins were <0.1 unit/mg of proteins measured by limulus amoebocyte lysate (LAL) from Cape Cod.

Construction of Adenoviral CC3

The forward primer 5'-AAGAATTCATGCGA-CATTTTCATGCGTCTCAGTGC-3' (SEQ ID NO: 39) and the reverse primer 5'-AACTCGAGTCAGCTTTCA-GTTTCCTCTAATTCTTC-3' (SEQ ID NO: 40) were used to amplify the cytoplasmic CC3 motif of human Robo1 encoding amino acid sequence 1,492-1,651, which was then digested with BamH1/Xho1 and ligated into the vector of DUALGFP-CCM (Vector Biolabs) for construction of adenoviral CC3 plasmid (Ad-CC3). The construct was verified by DNA sequence analysis. The high titers of custom-made Ad-CC3 and its control adenoviral GFP (Ad-GFP) were purchased from Vector Biolabs.

Transfection and Determination of TCF/LEFT Promoter Activity

To determinate β-catenin transcriptional activity, the plasmids encoding wild-type LEF/LEF luciferase reporter (TOP-Flash) and β-galactosidase, in the absence or presence of the plasmids of Robo1 and its mutants, were co-transfected into 293 cells using Lipofectamine 2000 (Invitrogen). Transfectants were incubated with recombinant Rspo1, Slit2 and/or Wnt3a (R&D Systems; all at 0.5 µg/ml) for 24 hours or infected with Ad-CC3 (1×10$^8$ PFU/ml) for 24 hours. Luciferase activity was determined in cell lysates using the Luciferase Assay System (Promega) and transfection efficiency was normalized with β-galactosidase activity determined using the Luminescent β-galactosidase Detection Kit II (BD Clontech).

Example 12

This example demonstrates that the intestinal crypts are more resistant to IR-induced apoptosis than the intestinal villi. Fast cycling adult stem cells in the bone marrow (see, e.g., Mohrin et al., 2010 Cell Stem Cell, Volume 7, Issue 2, 174-185), the skin bulge (see, e.g., Sotiropoulou, P. A., et al., 2010 Nature Cell Biol. 12, 572-582), the brain cortex (see, e.g., Roque, T., et al., 2012 Stem Cells 30, 537-547) and the small intestine (see, e.g., Hua, G., et al., 2012 Gastroenterology 143, 1266-1276), are reportedly resistant to chemoradiation. As this may mechanistically relate to previous observations (Zhou et al., 2013 Nature 501, 107-111), the effect of ionizing radiation (IR) on the wild-type small intestine at the crypt-villus axis, as visualized by immunofluorescent staining of p53 and active caspase 3 (a marker for cell apoptosis; see, e.g., Haimovitz-Friedman et al., 2012 Radiat. Res. 177, 467-482), was investigated. In the dose response experiments using whole body IR, it was found that the expression of p53 and active caspase 3 in the crypts appeared ~2-4 Gy lower than those in the villi (FIGS. 25A and 25D). The expression of p53 and caspase 3 peaked at ~10-12 Gy in the crypts, whereas it peaked earlier at ~6-8 Gy in the villi. Similar delays for the expression of p53 mRNA (FIG. 25B) and the transcriptional activity of p53 (FIG. 25C) were evident in the crypts as compared to the villi. These observed differences between the crypts and the villi disappeared at ~10-12 Gy when the expression of p53 and active caspase 3 was maximal. Correlated with the evidence for the fast physiologic recycling of intestinal epithelial cells (see, e.g., Clevers and Nusse, 2012 Cell 149, 1192-1205; Clevers, H. 2013 Cell 154, 274-284), the expression of active caspase 3 was also detected in the tips of several untreated intestinal villi (see the image at 0 Gy in FIG. 25D). These findings confirm the previous reports (see, e.g., Mohrin et al., 2010 Cell Stem Cell, Volume 7, Issue 2, 174-185; Sotiropoulou, P. A., et al., 2010 Nature Cell Biol. 12, 572-582; Roque, T., et al., 2012 Stem Cells 30, 537-547;

Hua, G., et al., 2012 Gastroenterology 143, 1266-1276; Zhou et al., 2013 Nature 501, 107-111; Metcalfe, C., et al., 2013 Cell Stem Cell Vol. 14 Issue 2 149-159), implicating that the intestinal crypts, where ISCs, Paneth cells and transient amplifying cells reside, are indeed more resistant to IR-induced damage than the intestinal villi.

Example 13

Figure 26:
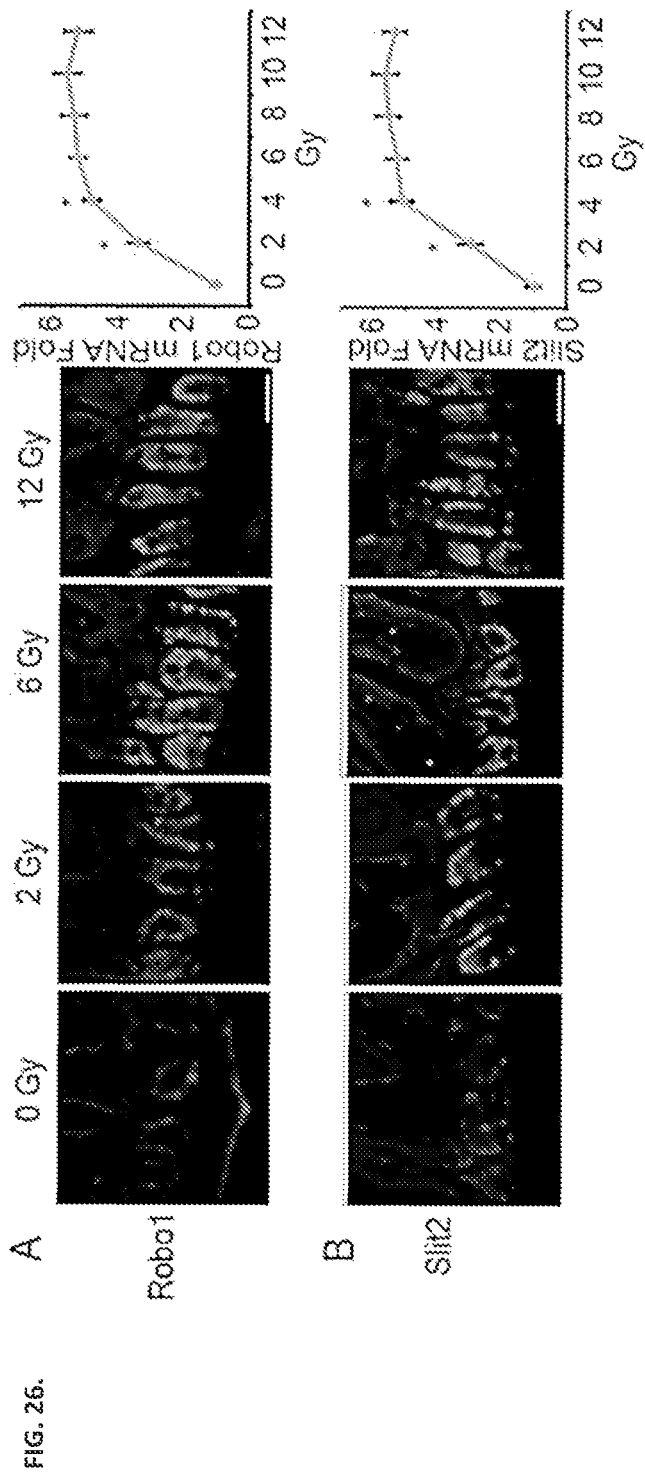
FIG. 26 presents a dose-response of IR-induced Robo1 and Slit2 mRNA expression in the small intestine. Wild-type C57 mice received whole body IR (12 Gy) and the small intestines were harvested 2 days later. Robo1 and Slit2 mRNAs were detected with the DIG- or biotin-conjugated antisense mRNA probes for Robo1 and Slit2 (A and B; left panels) and with their respective qPCR primer pairs (A and B; right panels). Slides were counterstained with DAPI. Results are representative images and the mean±S.D. of 10 tissue sections/mouse (8 weeks old; 3 mice/group). Bars, 50 μm for A and B. *, p<0.05 (Kruskal-Wallis test).
Figure 27:
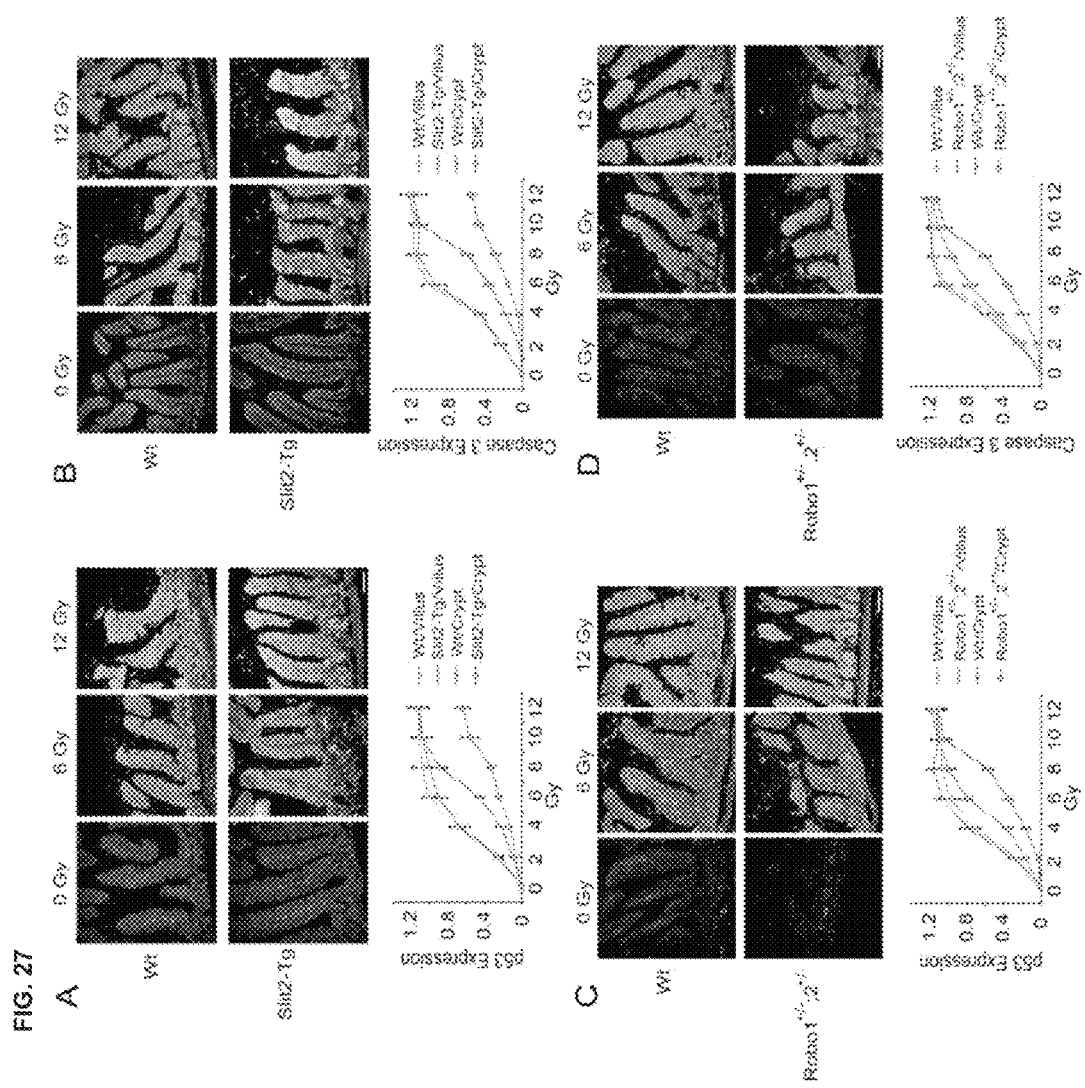
FIG. 27 shows genetic modulation of IR-mediated apoptosis of the intestinal crypts. (A and B) Slit2 transgene suppresses p53-mediated intestinal crypt apoptosis. Wild-type C57 (Wt) and Slit2-Tg mice received whole body IR at 0, 2, 4, 6, 8, 10 or 12 Gy. They were euthanized 2 day later and the small intestines were stained for p53 (A) and active caspase 3 (B). (C and D) Partial genetic deletion of Robo1/2 accelerates IR-induced intestinal crypt apoptosis. The littermate control (Wt) mice and Robo1/2 mutants received whole body IR at 0, 2, 4, 6, 8, 10 or 12 Gy. They were euthanized 2 days later and the small intestinal tissues were stained for p53 (C) and active caspase 3 (D). Results represent fifty tissue specimens in each group (n=5) and the mean±S.D. values. Bars, 50 μm for A and D. *, p<0.05 (Kruskal-Wallis test).
Figure 28:
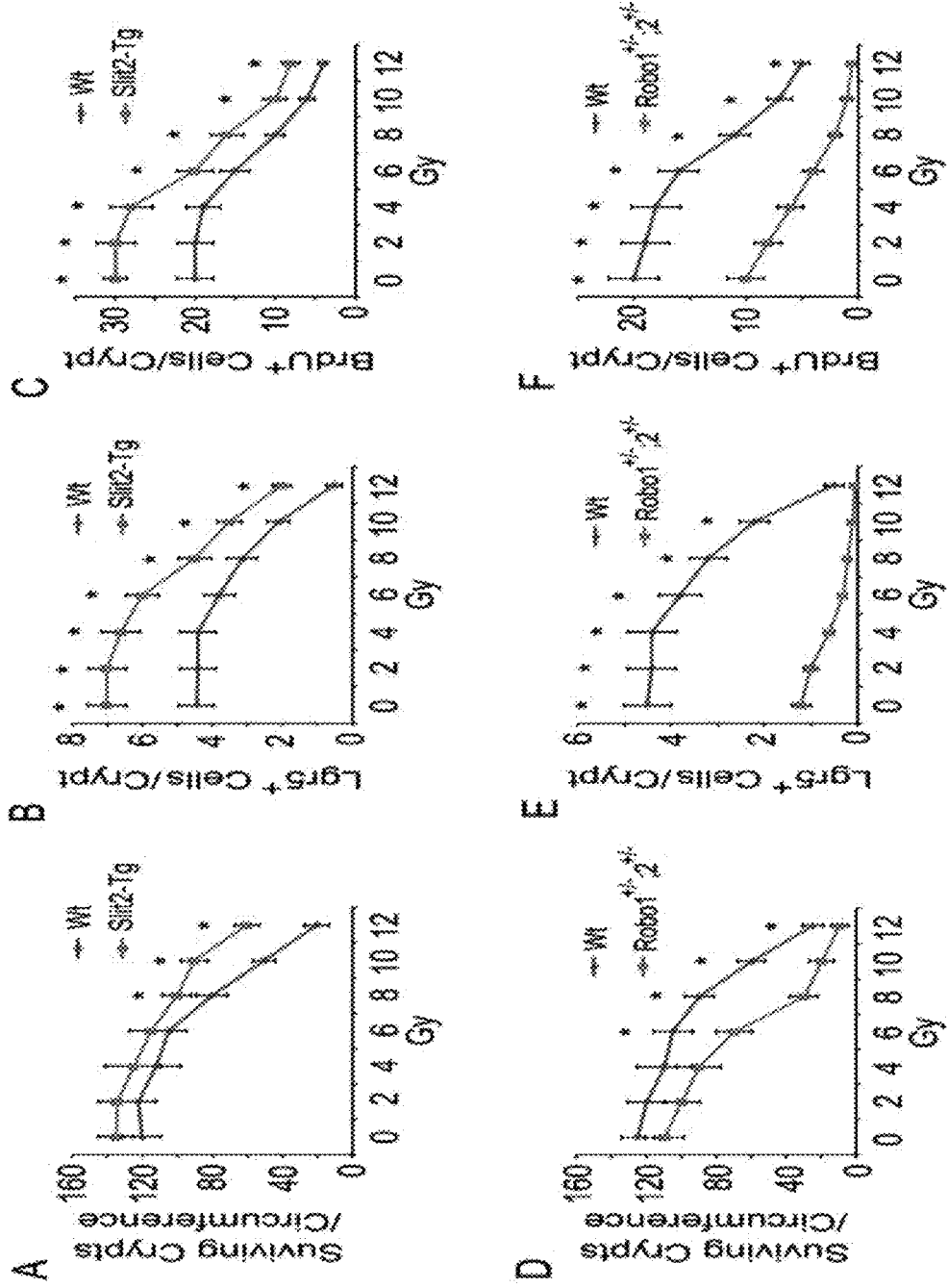
FIG. 28 shows the effects of Slit2 transgene, Robo1/2 mutants and rRspo1/rSlit2 on the numbers of surviving crypts, Lgr5+ cells and BrdU+ crypt cells. Wild-type C57 and Slit2-Tg mice (A to C), the littermate controls and Robo1/2 mutants (D to E), and Lgr5-GFP mice treated with saline and rRspo1/rSlit2 (G to I) received whole body IR (12 Gy). Mice were euthanized two days post IR (A to F) or at the indicated day after IR (G to I). The numbers of surviving crypts/circumference were counted. In addition, the specimens of small intestine were immunohistologically stained for Lgr5 for counting Lgr5+ cells/crypt1. For measurement of crypt cell proliferation, mice were injected with BrdU (1 mg per 100 g of body weight) for 2 h before euthanization for determining BrdU+ cells in the intestinal crypts. Furthermore, Lgr5-GFP mice were injected intravenously with rRspo1 plus rSlit2 (0.1 mg per mouse per day for three consecutive days). Results represent fifty tissue specimens in each group (8 weeks old; n=5) and the mean±S.D. values. *, p<0.05 (Kruskal-Wallis test).

This example demonstrates IR-induced intestinal expression of Slit2 and Robo1. The Lgr5$^+$ ISCs and Ki67$^+$ transient amplifying cells, but not lysozyme$^+$ Paneth cells, express Robo1 and Slit2 in the crypts of small intestine (Zhou et al., 2013 Nature 501, 107-111). With the fluorescent in situ hybridization (FISH), it was found that IR drastically induced the expression of Robo1 and Slit2 mRNAs, which were restricted in the crypts, but not in the villi (FIGS. 26A and B; left panels). Notably, the Robo1$^+$ and Slit2$^+$ fluorescent staining signals at the unchallenged state (0 Gy) (Zhou et al., 2013 Nature 501, 107-111) was purposefully filtered out for the purpose of better illustrating IR-induced Robo1 and Slit2 up-regulation. The dose-responses of IR-induced up-regulation of Robo1 and Slit2 mRNAs, quantified by real-time polymerase chain reaction (qPCR), were also evident in the isolated intestinal crypts (FIGS. 26A and B; right panels). Importantly, the IR-induced expression of Robo1 and Slit2 mRNAs peaked as low as ~4 Gy in the crypts, which was in sharp contrast to the observed peak staining of p53 and active caspase 3 at ~10-12 Gy (FIG. 25A to D). Considering that IR up-regulated Robo1 and Slit2 expression in the IR-resistant intestinal crypts, but not in the IR-sensitive intestinal villi (FIG. 26), and that the expression of Robo1 and Slit2 preceded the p53 expression and its apoptotic activity (FIG. 25A to F), it was suspected that Slit-Robo signaling could contribute to the observed radio-protection of the intestinal crypt cells, especially those within the stem cell clonogen (SCC) compartment of intestinal crypts (Hua, G., et al., 2012 Gastroenterology 143, 1266-1276; Zhou et al., 2013 Nature 501, 107-111).

Example 14

This example demonstrates regulation of p53-mediated apoptosis by genetic modulation of Slit2 and Robo1. To test this, whether genetic manipulation of Slit2 or Robo1 might alter the IR-induced p53 expression and its apoptotic activity in the intestinal crypts was examined. With the same dose-response regime of whole body IR using wild-type C57 and Slit2 transgenic (Slit2-Tg) mice (Zhou et al., 2013 Nature 501, 107-111), it was found that Slit2 transgene delayed and attenuated p53 expression (FIG. 27A) and p53-mediated apoptosis in the SCC compartment (FIG. 27B). Consistently, ectopic expression of Slit2 transgene also protected IR-induced loss of Lgr5$^+$ ISCs and BrdU$^+$ cells in the intestinal crypts (FIG. 28A-C). As complete or partial genetic deletion of Robo1 is embryonically-lethal, while mice with partial genetic deletion of both Robo1 and 2 are viable, Robo1$^{+/-}$; Robo2$^{+/-}$ double heterozygotes (Robo1/2 mutants; Grieshammer, U., et al., 2004 Dev. Cell 6, 709-717; Long, H., 2004 Neuron 42, 213-223) were also employed. Notably, no intestinal expression of Robo2 mRNA was detected after whole body IR (12 Gy). Compared to their littermate controls, partial genetic deletion of Robo1/2 prompted p53 expression (FIG. 27C), accelerated p53-mediated apoptosis (FIG. 27D), and exaggerated loss of Lgr5$^+$ ISCs and BrdU$^+$ crypt cells (FIG. 28D-F). These findings support the functional significance of Slit-Robo signaling in modulating IR-induced p53 expression and consequently p53-mediated apoptosis of the intestinal crypts in the SCC compartment of intestinal crypts.

Example 15

This example demonstrates that Rspo1 binds to the extracellular segment of Robo1 while the cytoplasmic tail of Robo1 binds to Lrp6. To investigate whether and how Rspo1 and Slit2 acted coordinately to enhance ISC chemoradioprotection, whether Rspo1 binds to Robo1 at the intestinal crypt was tested. Indeed, endogenous Robo1, immunoprecipitated from the lysates of wild-type intestinal crypts, was found to associate with native Rspo1 and vice versa (FIG. 29A), suggesting an interaction between these two proteins. Biochemically, it was found that the NH$_2$ portion of Rspo1 containing two furin-like domains interacts directly with the extracellular Ig-like 3 and 4 domains of Robo1.

As Wnt3a and Rspo1 induce the Frizzled (Fzd)-low-density lipoprotein receptor-related protein 6 (Lrp6) complex for activation of canonical Wnt signaling (Clevers and Nusse, 2012 Cell 149, 1192-1205; Clevers, H. 2013 Cell 154, 274-284), it was asked whether Robo1 could bind to Lrp6. To test this, Robo1 was immunoprecipitated from the lysates of wild-type intestinal crypts, followed by immunoblotting for Lrp6. Endogenous Robo1 was found to associate with native Lrp6 and vice versa (FIG. 29B). It was further demonstrated that the cytoplasmic CC3 motif of Robo1 directly interacts with the cytoplasmic segment of Lrp6 at its COOH-terminus.

Given that leucine-rich repeat-containing G protein-coupled receptor 4/5 (Lgr4/5) associates with the Fzd/Lrp5/6 complex (de Lau et al., 2011 Nature 476, 293-297), whether the newly identified intracellular Robo1-Lrp6 complex could modulate the association of Lgr4/5 with the Fzd/Lrp5/6 complex was investigated. Using the intestinal crypts isolated from wild-type littermates and Robo1/2 mutants, it was found that endogenous Lrp6 associated with Lgr5 and vice versa (FIG. 29C). Importantly, partial genetic deletion of Robo1/2 clearly reduced the association of endogenous Lrp6 with Lgr5, indicating that Robo1 not only binds directly to the carboxyl segment of cytoplasmic Lrp6, but also enhances the formation of Lrp6-Lgr5 complex.

Example 16

This example demonstrates that Robo1 binding to Lrp6 activates Wnt/β-catenin signaling. It was next tested whether Slit-Robo signaling affects Lrp6 phosphorylation in vivo. Compared to the littermate counterparts, the Robo1/2 mutant intestinal crypts manifested decreased pS1490Lrp6 phosphorylation (FIG. 30A), whereas the Slit2-Tg intestinal crypts displayed increased pS1490Lrp6 phosphorylation (FIG. 30B). Infection of isolated wild-type intestinal crypts with Ad-CC3, but not Ad-GFP, also prevented pS$^{1490}$Lrp6 phosphorylation (FIG. 30C). As Lrp6 phosphorylation induced by Rspo1 activates Wnt/β-catenin signaling (Glinka et al., 2011 EMBO Rep. 12, 1055-1061; Carmon et al., 2011 Proc. Natl. Acad. Sci. USA. 108, 11452-11457; Gong et al., 2012 PLoS One 7, e37137), it was tested whether engagement of Robo1 by Rspo1 and Slit2 could modulate Rspo1-induced Lrp6 phosphorylation and Tcf/Lef promoter activity. Incubation of Robo1-negative 293 cells with rRspo1, but not rSlit2, elicited pS$^{1490}$ Lrp6 phosphorylation (FIG. 30D). However, both rRspo1 and rSlit2 induced pS$^{1490}$Lrp6 phosphorylation following transient transfection of 293 cells with the plasmid of Robo1. Importantly, rSlit2 potentiated Rspo1- elicitated pS$^{1490}$Lrp6 phosphorylation. Consistently, incubation of Robo1-negative 293 cells with rRspo1 triggered the Tcf/Lef promoter luciferase activity (~2-3-fold; FIG. 30E). rWnt3a, but not rSlit2, acted synergistically with rRspo1 for increasing the Tcf/Lef promoter activity (~13-fold). However, transfection of 293 cells with the Robo1 plasmid augmented the Tcf/Lef promoter activity (~2-3-fold). Importantly, the Tcf/Lef promoter activity in Robo1-expressing 293 cells was induced by rRspo1 or rSlit2 alone (~6-7-fold), further induced by rRspo1 plus rSlit2 (~22-fold) or rRspo1 plus Wnt3a (~26-fold), and maximally induced by a combination of rRspo1, rSlit2 and rWnt3a (~40-fold). As predicted, transfection of 293 cells with the plasmids of Robo1 and Poβo1-Ig, but not the plasmids of Robo1-FN and Robo1-dCC3, increased the Tcf/Lef promoter activity in the presence or absence of rRspo1 (FIG. 30F). Compared to Ad-GFP, Ad-CC3 attenuated rRspo1 and/or rSlit2-induced pS$^{1490}$Lrp6 phosphorylation (FIG. 30G) and Tcf/Lef promoter activity (FIG. 30H) in transfected 293 cells. The interaction of cytoplasmic Robo1 with Lrp6 is thus indispensable for the Rspo1/Slit2-mediated pS$^{1490}$Lrp6 phosphorylation and Tcf/Lef promoter activation. Notably, such findings are consistent with the previous reports that Slit-Robo signaling suppresses cadherin-mediated cell-cell adhesion (Rhee et al., 2002 Nat. Cell Biol. 4, 798-805; Qian et al., 2005 Curr. Biol. 15, 2271-2278; MacMullin and Jacobs, 2006 Dev. Biol. 293, 154-164; Santiago-Martinez et al., 2006 Proc. Natl. Acad. Sci. USA 103, 12441-12446; Rhee et al., 2007 Nat. Cell Biol. 9, 883-892; Santiago-Martinez et al., 2008 J. Cell Biol. 182, 241-248; Medioni et al., 2008 J. Cell Biol. 182, 249-261; Fish et al., 2011 Development 138, 1409-1419; Zhou et al., 2011 Cell Res. 21, 609-626), thus inactivating GSK3β (Byun et al., 2012 PLoS One 7, e51895) and activating β-catenin (Rhee et al., 2002 Nat. Cell Biol. 4, 798-805).

The in vivo effects of Slit-Robo signaling on the cellular localization of β-catenin and the expression of Wnt targeting genes in the small intestine were next examined. When the cytoplasmic and nuclear fractions of the mouse small intestinal crypts were separated, it was found that Robo1/2 mutants and R5 (a monoclonal antibody that binds to Robo1 and neutralizes Slit2 binding to Robo1; Wang et al., 2003 Cancer Cell 4, 19-29)-treated wild-type mice had decreased β-catenin in their cytoplasmic and nuclear fractions, as compared to their Wt counterparts, with or without mIgG treatment (FIG. 30I, upper panel). In contrast, Slit2-Tg mice displayed increased β-catenin in their cytoplasmic and nuclear fractions. Immunoblotting of the cytoplasmic marker α-tubulin (tub; FIG. 30I, middle panels) and Sp1 (a marker for the nucleus; FIG. 30I, lower panels) served as controls. As the control for the observed β-catenin translocation, total lysates of the small intestinal crypts without the cytoplasmic and nuclear fractionation were also immunoblotted for β-catenin (FIG. 30J). Additionally, the protein expression of Wnt targeting genes, including c-Myc, ephB2 and ephB3 proteins, was down-regulated in the intestines of Robo1/2 mutants and R5-treated Wt mice when compared to their Wt counterparts, with or without mIgG treatment (FIG. 30K, L). The data collectively indicate that the interaction of the cytoplasmic CC3 motif of Robo1 with the carboxyl portion of cytoplasmic Lrp6 induces Lrp6 phosphorylation and Tcf/Lef promoter activation, downstream of Slit2-Robo1 and Rspo1-Robo1 signaling pathways, for critical activation of canonical Wnt signaling during physiologic maintenance of intestinal homeostasis. This conclusion is substantiated by the finding that Rspo1 fails to rescue the intestinal impairment in Robo1/2 mutant mice (Zhou et al., 2013 Nature 501, 107-111).

Example 17

This example demonstrates Wnt/β-catenin activation suppresses p53 expression in Lgr5$^{high}$ ISCs at the transcriptional level. It was next tested whether Rspo1/Slit2-induced Robo1-Lrp6-Lgr5 complex could regulate the IR-induced p53 expression. As expected, treatment of Robo1-negative 293 cells with rRspo1/rSlit2 failed to affect the IR-induced expression of p53 protein and mRNA (FIG. 31A, B). In contrast, rRspo1/rSlit2 potently inhibited these following transfection of 293 cells with the plasmid of Robo1. Infection of Robo1-expressing 293 cells with Ad-GFP or Ad-CC3 had limited effects on the IR-induced expression of p53 protein and mRNA (FIG. 31C, D) in the absence of rRspo1 plus Slit2. However, compared to Ad-GFP, Ad-CC3 significantly neutralized the inhibitory action of rRspo1/rSlit2 on the IR-induced p53 protein and mRNA expression in Robo1-expressing 293 cells. Following co-transfection of 293 cells with the plasmids of p53 promoter luciferase reporter (pGL2-2.4 kb and pGL2-356 bp), it was found that IR induced p53 promoter activity reported by both constructs regardless of the promoter lengths (FIG. 31E). In contrast, rRspo1/rSlit2 abolished ~70-80% IR-induced p53 promoter activity in the Robo1-expressing cells co-transfected with the pGL2-2.4 kb plasmid, but not the pGL2-356 bp plasmid. Consistent with the biochemical findings (FIG. 29), rRspo1/rSlit2 failed to affect the IR-induced p53 promoter luciferase activities in Robo1-negative 293 cells (FIG. 31F). As 293 cells constitutively secretes endogenous Slit2, co-transfection with the plasmids of Robo1 and Robo1-Ig, but not Robo1-FN and Robo1-dCC3, partially inhibited the IR-induced p53 promoter luciferase activities. Importantly, rRspo1/rSlit2 further suppressed the IR-induced p53 promoter luciferase activities in the Robo1 and Robo1-Ig expressing 293 cells, but not in the Robo1-FN and Robo1-dCC3 expressing 293 cells. Again, Ad-CC3, but not Ad-GFP, neutralized the inhibitory effect of rRspo1/rSlit2 on the IR-induced p53 promoter activity in Robo1-expressing 293 cells (FIG. 31G).

Using Lgr5$^{high}$ ISCs isolated from Lgr5-GFP mice (Barker et al., 2007 Nature 449, 1003-1007) and sorted by flow cytometry (Sato et al., 2009 Nature 459, 262-265), it was found that treatment with rRspo1/rSlit2 potently prevented the expression of endogenous p53 (FIG. 31H, I) and active caspase 3 (FIG. 31J) in IR-treated Lgr5$^{high}$ ISCs, but not in resting Lgr5$^{high}$ ISCs. Compared to Ad-GFP, Ad-CC3 neutralized the suppressive action of rRspo1/rSlit2 on the IR-induced expression of p53 (FIG. 31K, L) and active caspase 3 (FIG. 31M). Consistently, IR abolished in vitro formation of intestinal organoids, which was partially rescued by adding additional amounts of rRspo1/rSlit2 (FIG. 31N). Interestingly, the intestinal organoids rescued by additional rRspo1/rSlit2 following IR were capable of forming intestinal organoids during second passage. These data support the hypothesis that Wnt/β-catenin agonists Rspo1 and Slit2 regulate the p53 expression mainly at the transcriptional level in IR-treated Lgr5$^{high}$ ISCs.

Example 18

This example demonstrates isolation of recombinant Fc-fusion chimeras. To prolong the serum half-life (Kontermann, 2011 Curr. Opin. Biotechnol. 22, 868-876;

Czajkowsky et al., 2012 EMBO Mol. Med. 4, 1015-1028), the baculovirus expression plasmids of human Robo1 fused with the Fc segment of human $IgG_4$ (Robo1-Fc) and human Rspo1 and Slit2 fused with the Fc segment of human $IgG_4$ (Rspo1-Fc and Slit2-Fc) were constructed. Notably, rRobo1-Fc contains all five extracellular immunoglobulin (Ig)-like domains of human Robo1, in which Slit2 binds to the Ig-like 1 domain (Morlot et al., 2007 Proc. Natl. Acad. Sci. USA 104, 14923-14928) while Rspo1 binds to the Ig-like 3 and 4 domains. Generation of the corresponding high-titer viral stocks were completed, which allowed isolation of large amounts of recombinant Robo1-Fc (rRobo1-Fc), Rspo1-Fc (rRspo1-Fc) and Slit2-Fc (rSlit2-Fc; FIG. 32) from the serum-free supernatants of the infected Sf9 insect cells, using Protein A affinity chromatography (Wang et al., 2007 Nat. Immunol. 8, 882-892).

Example 19

This example pertains to experiments that will demonstrate chemoradiation-induced gut injury protection by Wnt agonists.

Rspo1/Slit2 Promotes Gut Injury Repair Following Chemoradiation.

It has been previously discovered that rRspo1/rSlit2 reduces $Lgr5^{high}$ ISC loss, mitigates gut injury and protects mice from death caused by the lethal doses of chemoradiation (Zhou et al., 2013 Nature 501, 107-111). In support of these findings, $Lgr5^+$ ISCs are recently found to be indispensable to radiation-mediated gut injury repair (Metcalfe, C., et al., 2013 Cell Stem Cell Vol. 14 Issue 2 149-159). Along this line of investigation, it was also found that Slit2 transgene suppressed IR-mediated apoptosis in the SCC compartment (FIGS. 27A, B and 28A-C). Furthermore, rRspo1/rSlit2 potently prevented the expression of p53 and the p53-mediated apoptosis of IR-treated $Lgr5^{high}$ ISCs (FIG. 31). To substantiate these findings, whether a 3-day pulse with rRspo1/rSlit2 (Zhou et al., 2013) attenuates the expression of p53 and reduces the p53-mediated apoptosis in the SCC compartment of C57 and Lgr5-GFP mice following IR will be tested. In this set of experiments, C57 and tamoxifen-treated Lgr5-GFP mice (8 weeks old) will receive rRspo1/rSlit2 (intravenous administration of 0.1 mg/mouse/day for 3 consecutive days). On day 2, they will receive whole body IR (10.4 or 12 Gy). On day 4, they will be euthanized. The villus length, the surviving $Lgr5^+$ ISCs, the crypt numbers, the expression of Wnt targeting genes such as c-Myc, the expression of p53 and active caspase 3, the p53 apoptotic activity, and the rate of BrdU incorporation will be determined as described in our abovementioned preliminary studies or the previous publication (Zhou et al., 2013 Nature 501, 107-111).

As the in vivo serum half-life of rRspo1 or rSlit2 was short (1 hour), a large amount of rRspo1-Fc (FIG. 32A) and rSlit2-Fc (FIG. 32B) were constructed, expressed and isolated. Following removing their endotoxin (Wang et al., 2007 Nat. Immunol. 8, 882-892), rRspo1-Fc and rSlit2-Fc were administered into mice through the tail vein and determined their in vivo serum half-life, using the ELISA kit for human IgG4 (88-50590-22; eBioscience). Consistent with previous reports (Kontermann, 2011 Curr. Opin. Biotechnol. 22, 868-876; Czajkowsky et al., 2012 EMBO Mol. Med. 4, 1015-1028), the in vivo serum half-life for rRspo1-Fc or rSlit2-Fc was ~5 days. To confirm this preliminary finding, this set of experiments using at least three separate preparations of isolated rRspo1-Fc and rSlit2-Fc will be repeated.

The dose course experiments will be performed using a single dose of 0, 1, 3, 10 or 30 μg/mouse (equivalent to 0.05, 0.15, 0.5 or 1.5 mg/kg if assuming the body weight of each mouse being 20 g) either rRspo1-Fc and rSlit2-Fc individually or in combination, one day prior to the lethal dose of chemoradiation (one single dose of 300 mg/kg 5-FU or 10.4 Gy whole body IR once; Zhou et al., 2013 Nature 501, 107-111). Again, rRspo1-Fc and rSlit2-Fc from at least three separate preparations will be tested. Human intact $IgG_4$ (ab90286; abcam) will be used in parallel as the isotype-matched control. Lgr5-GFP mice (Barker et al., 2007 Nature 449, 1003-1007) pretreated with tamoxifen will be used to facilitate the identification of $Lgr5^{high}$ ISCs. These mice will be euthanized on day 3 and the villus length, the surviving $Lgr5^+$ ISCs, the crypt numbers, the expression of c-Myc, p53 and active caspase 3, the p53 apoptotic activity, and the rate of BrdU incorporation will be determined. It is expected that pretreatment of mice with rRspo1/rSlit2 (a 3-day pulse) or rRspo1-Fc/rSlit2-Fc (one single dose) will repress p53 expression and inhibit p53-mediated apoptosis of $Lgr5^{high}$ ISCs, leading to accelerated repair of chemoradiation-induced gut injury.

Neutralization of Rspo1 and Slit2 by rRobo1-Fc Exaggerates Chemoradiation-Induced Gut Injury.

It was found that partial genetic deletion of Robo1/2 up-regulated p53 expression and exaggerated p53-mediated apoptosis in the SCC compartment following IR (FIGS. 27C, D; 28D-F). To confirm this finding, a large amount of rRobo1-Fc (FIG. 32) were constructed, expressed and isolated. As administration of rRobo1-Fc may bind and consequently "sink" endogenous Rspo1 and Slit2, it was hypothesized whether rRobo1-Fc accelerates the expression of p53 and exaggerates the p53-mediated apoptosis in the SCC compartment of wild-type and tamoxifen-treated Lgr5-GFP mice following whole body IR.

To test this hypothesis, the dose course experiments using a single dose of 0, 1, 3, 10 or 30 μg rRobo1-Fc/mouse (equivalent to 0.05, 0.15, 0.5 or 1.5 mg/kg if assuming the body weight of each mouse being 20 g) in C57 and tamoxifen-treated Lgr5-GFP mice without chemoradiation will be performed. Human intact $IgG_1$ (15154; Sigma-Aldrich) will be used in parallel as the isotype-matched control. In analog to R5 neutralizing monoclonal antibody (Zhou et al., 2013 Nature 501, 107-111), rRobo1-Fc should affect the intestinal homeostasis. After obtaining the optimal dose for rRobo1-Fc, the mice will then be treated with rRobo1-Fc followed by whole body IR. Again, the intestinal tissues will be examined for the villus length, the surviving $Lgr5^+$ ISCs, the crypt numbers, the expression of c-Myc, p53 and active caspase 3, the p53 apoptotic activity, and the rate of BrdU incorporation.

Possible Replacement of Rspo1/Slit2 with a Small Molecule Wnt Agonist CHIR-99021.

To speed up the possible translational application, whether CHIR-99021, a small molecule inhibitor for glycogen synthase kinase (GSK)-3α/β (Ring et al., 2003 Diabetes 52, 588-595; Ying et al., 2008 Nature 453, 519-523) for Wnt/β-catenin activation, could replace Rspo1 and/or Slit2 in the models will be tested. Whether CHIR-99021, in analog to rRspo1/rSlit2 (FIG. 31N), could rescue IR-treated $Lgr5^{high}$ ISCs in vitro will be tested. Whether compared to the 3-day pulse of rRspo1/rSlit2 (Zhou et al., 2013 Nature 501, 107-111) or the single usage of rRspo1-Fc/rSlit2-Fc, CHIR-99021 (oral gavage of 30 mg/kg/day until 5 days after chemoradiation challenge; Ring et al., 2003 Diabetes 52, 588-595) could protect chemoradiation-treated $Lgr5^{high}$ ISCs in Lgr5-GFP mice (Barker et al., 2007 Nature 449, 1003-1007) will be tested. As Slit-Robo signaling is known to modulate multiple key cellular targets (Zhou et al., 2011 Cell Res. 21, 609-626; Borrell et al., 2012 Neuron 76, 338-352), it is postulated that CHIR-99021 might replace rRspo1, but not rSlit2. If so, it could be interesting to test whether CHIR-99021 could act synergistically with rSlit2.

Expected Results, Interpretation and Anticipated Problems.

Although these proposed experiments seem straightforward, caution should be exercised when explaining these experimental data. To complement the findings, an alternative approach in the opposite direction should be performed in parallel. Specifically, the effects of Wnt/β-catenin antagonist PKF118-301, a small molecule inhibitor for β-catenin interaction with Tcf (Lepourcelet et al., 2004 Cancer Cell 5, 91-102), will be tested for its comparison with CHIR-99021. To further confirm the findings that Wnt agonists induce Lgr5$^{high}$ ISCs in response to IR, R26R-Confetti conditional allele (Stock No. 017492, Jax Mice) will be crossed with Lgr5-GFP mice and perform the lineage tracing experiments (Snippert et al., 2010 Cell 143, 134-44) following IR, with or without rRspo1-Fc/rSlit2-Fc and/or CHIR-99021.

It should be pointed out that the hypothalamus is recently found to express Lgr4-6 (Li et al., 2014 Acta Neurologica Scandinavica DOI: 10.1111/ane.12209). Interestingly, injection of Rspo1 or 3 into the third brain ventricle inhibits food intake. Notably, Slit2 transgene induces cerebral angiogenesis and opens up the blood-brain barrier (Han and Geng, 2011 Acta Pharmacologica Sinica 32: 1327-1336). If so, rSlit2 or rSlit2-Fc may facilitate the brain entry of rRspo1 or rRspo1-Fc following systemic administration. As the result, the food intake in our Rspo1/Slit2-treated mice in our experiments designed above will be closely monitored.

Example 20

This example pertains to experiments that will discern the differential effects of Wnt agonists on ISCs versus ICSCs following chemoradiation.

Differential Effects of Rspo1/Slit2 on Chemoradiation-Treated ISCs Versus ICSCs.

It was speculated whether in response to chemoradiotherapy, Wnt agonist-induced Wnt/β-catenin activation and p53 down-regulation could induce ISCs for gut repair, but not ICSCs carrying aberrant β-catenin activation and p53 inactivation for tumor growth, chemoradiation resistance or relapse. To test this hypothesis, a successful crossing of Trp53 floxed mice (Stock No. 008462; Jax Mice) with Lgr5-GFP mice (Stock No. 008875; Jax Mice) to delete Trp53 in Lgr5$^{high}$ ISCs by tamoxifen administration was observed. These mice will be further treated with AOM/DSS (Katoh et al., 2013 Cancer Cell 24, 631-644) to induce transformation of Trp53-null Lgr5$^{high}$ ISCs into neoplastic ICSCs. If needed, the multiple cycles of AOM/DSS could be carried out. Using this chemical-induced ICSC model, whether rRspo1-Fc/rSlit2-Fc and/or CHIR-99021 induces ISCs and repair gut injury, but will not adversely affect ICSCs for promoting tumor growth, chemoradiation resistance or relapse following standard chemoradiotherapy will be tested.

To mimic clinical setting, the chemical-induced ICSC model mice described above will receive the therapeutic doses of chemoradiotherapy; that is, 30 mg/kg 5-FU/day or 1.5 Gy abdominal IR/day for 5 consecutive days; rest for one week and then start another 5-day treatment; up to 3 to 6 cycles. In parallel, these mice will receive rRspo1-Fc/rSlit2-Fc and/or CHIR-99021 at the optimal time and dose as determined above. Again, human intact IgG$_4$ will be used as the isotype-matched control. Importantly, these mice will be examined again 3 and 6 months after these regimens of chemoradiotherapy to determine whether treatment with rRspo1-Fc and/or rSlit2-Fc would adversely elicit tumor relapse.

For all the "rescue" experiments, the villus length, the surviving Lgr5 ISCs, the crypt numbers, the expression of c-Myc, p53 and active caspase 3, the p53 apoptotic activity, and the rate of BrdU incorporation will be determined. In addition, the Lgr5 ICSC-derived tumors will be closely monitored. It is predicted that treatment with rRspo1-Fc/ rSlit2-Fc and/or CHIR-99021 will enhance host tolerance to chemoradiotherapy without concomitantly promoting tumor growth, chemoradiation resistance and relapse derived from p53-inactivated ICSCs.

Distinctive Actions of Slit2 Transgene on Chemoradiation-Treated ISCs Versus ICSCs.

To verify this hypothesis, Slit2-Tg mice (Yang et al., 2010 Biochem. Biophys. Res. Commun. 396, 571-577; Ye et al., 2010 J. Immunol. 185, 6294-6305; Han and Geng, 2011 Acta Pharmacologica Sinica 32: 1327-1336); Guo et al., 2013 Reprod. Sci. 20, 285-298; Zhou et al., 2013 Nature 501, 107-111) will be crossed with Trp53$^{-/-}$; Lgr5-GFP mice. As Slit2 transgene constitutively activates canonical Wnt signaling and induces Lgr5$^{high}$ ISC proliferation (Zhou et al., 2013 Nature 501, 107-111), it is interesting to examine whether Wnt/β-catenin activation induced by Slit2 transgene could exaggerate transformation of Trp53-null Lgr5$^{high}$ ISCs into neoplastic ICSCs, in the presence or absence of AOM/ DSS (Katoh et al., 2013 Cancer Cell 24, 631-644), following tamoxifen-mediated deletion of Trp53 in Lgr5$^{high}$ ISCs. The constitutive canonical Wnt activation and p53 inactivation induced by Slit2 transgene in this compound strain of mice may vividly mimic those concurrent Wnt-activated and p53-inactivated ICSCs in CRC (Kinzler and Vogelstein, 1996 Cell 87, 159-170; Vogelstein et al., 2013 Science 339, 1546-1558; Holland et al., 2013 Curr. Opin. Cell Biol. 25, 254-264). It should be emphasized that the temporal activation of Wnt/β-catenin by treatment with rRspo1/rSlit2 could be very different from the constitutive Wnt/β-catenin activation induced by Slit2 transgene for colorectal tumorigenesis.

Using this compound mutant mouse strain, whether Slit2 transgene could enhance host tolerance to chemoradiotherapy without concomitantly promoting tumor growth, chemoradiation resistance and relapse derived from Lgr5$^+$ ICSCs, in which Wnt/β-catenin is already activated and Trp53 is genetically deleted will next be tested. Again, the therapeutic doses of chemoradiotherapy will be employed as above. In addition, these mice will be examined again 3 and 6 months after these regimens of chemoradiotherapy to determine whether Slit2 transgene would trigger tumor relapse. The villus length, the surviving Lgr5$^+$ ISCs, the crypt numbers, the expression of c-Myc, p53 and active caspase 3, the p53 apoptotic activity, and the rate of BrdU incorporation will be determined as above.

Expected Results, Interpretation and Anticipated Problems.

As an alternative approach, Robo1/2 mutants (Grieshammer et al., 2004 Dev. Cell 6, 709-717; Long et al., 2004 Neuron 42, 213-223), as compared to Slit2-Tg mice, will be crossed with Trp53$^{-/-}$; Lgr5-GFP mice. It should be mentioned that Slit-Robo signaling regulates leukocyte chemotaxis (Wu et al., 2001 Nature 410(6831) 948-952; Guan et al., 2003 J. Immunol. 171, 6519-6526; Kanellis et al., 2004 Am. J. Pathol. 165, 341-352; Chen et al., 2004 J. Immunol.

173, 5914-5917; Prasad et al., 2007 J. Leukoc. Biol. 82, 465-476; Altay et al., 2007 Exp. Neurol. 207, 186-194; Ye et al., 2010 J. Immun. 185(10) 6294-6305) and angiogenesis and/or angiostasis (Wang et al., 2003 Cancer Cell 4, 19-29; Bedell et al., 2005 Proc. Natl. Acad. Sci. USA 102, 6373-6378; Suchting et al., 2005 FASEB J. 19, 121-123; Wang et al., 2008 Cancer Sci. 99, 510-517; Jones et al., 2008 Nat. Med. 14, 448-453; Jones et al., 2009 Nat. Cell Biol. 11, 1325-1331; Zhang et al., 2009 Blood 114, 4300-4309; Urbich et al., 2009 Blood 113, 5669-5679; Dunaway et al., 2011 Mol. Cell. Biol. 31, 404-416; Han and Geng, 2011 Acta Pharmacologica Sinica 32: 1327-1336; Guo et al., 2013 Reprod. Sci. 20, 285-298; Seth 2005 Biochem. Biophys. Res. Commun. 332, 533-541). Accordingly, the distribution of neutrophils, macrophages and T lymphocytes and vascular endothelial cells within the gut tissues will need to be examined, which will allow detection of their possible involvements in the proposed studies.

Example 21

This examples pertains to experiments to selectively target Wnt/β-catenin-activated and p53-inactivated CRC by Wnt agonist-mediated tissue repair during chemoradiotherapy.

Combination Therapy of Wnt/β-Catenin Agonists and Chemoradiation for Preferential Targeting of Wnt/β-Catenin-Activated and p53-Inactivated CRC.

In a previous study, it was found that human colorectal cancer cell lines, SW620, SW480, Caco2 and LS174T cells, express endogenous Slit2 and Robo1 (Zhou et al., 2011 Nature 501, 107-111). Notably, SW620, SW480 and Caco2 cells, but not LS174T cells, are featured with simultaneous APC and TP53 loss-of-function mutations (Rodrigues et al., 1990 Proc. Natl. Acad. Sci. USA 87, 7555-7559). It is thus suspected whether Rspo1/Slit2 and/or CHIR-99021 preferentially protect LS174T cells, as compared to SW620, SW480 and Caco2 cells in response to chemoradiation. To test this hypothesis, the in vitro assay established and used in FIG. 31N will be employed. Briefly, these cells will first receive 12 Gy IR and then transfer to tissue culture dishes in the presence or absence of rRspo1/rSlit2 and/or CHIR-99021. The numbers of survival cells will be counted afterwards on the daily basis. To substantiate these cell number measurements, we will also determine pS1490Lrp6 phosphorylation, β-catenin cellular translocation, Wnt targeting gene expression including p53 and p53-mediated apoptotic activity, and the BrdU incorporation rate as described above.

Protection of ISCs by Wnt/β-Catenin Agonists while Targeting Wnt/β-Catenin-Activated and p53-Inactivated CRC.

On the basis of the aforementioned in vitro findings, the hypothesis will be tested in vivo, using the xenograft model in which athymus nude mice will be subcutaneously inoculated with SW620, SW480 or Caco2 cells (Zhou et al., 2011 Cell Res. 21, 609-626). Whether treatment with rRspo1-Fc/rSlit2-Fc and/or CHIR-99021 induces ISCs, reduces gut injury and enhances host tolerance to the multiple cycles of standard chemoradiotherapy, but does not accelerate tumor growth, metastasis and relapse will be tested. For the purpose of comparison, whether rRspo1-Fc/rSlit2-Fc and/or CHIR-99021, in the presence or absence of chemoradiotherapy, would adversely affect tumor growth, metastasis and relapse of LS174T cell-derived xenograft tumors in this murine model will also be tested. Human intact IgG$_4$ will be used as the isotype-matched control. Again, the villus length, the surviving Lgr5$^+$ ISCs, the crypt numbers, the expression of c-Myc, p53 and active caspase 3, the p53 apoptotic activity, and the rate of BrdU incorporation will be determined.

Expected Results, Interpretation and Anticipated Problems.

These proposed experiments are quite straightforward, as almost all methods and protocols have been established in the published and preliminary studies. However, as soon as the hypothesis has been verified using these CRC cell lines the hypothesis using the human CRC specimens available through the core facility of the University of Michigan Comprehensive Cancer Center will be tested. The human CRC specimens will be divided by the criteria as to whether they have the concurrent loss-of-function mutations of APC and TP53 or not, followed by treatment with the combination modality of rRspo1/rSlit2 and/or CHIR-99021 and standard chemoradiotherapy (5-FU and/or IR) in vitro. Using the orthotopic transplantation model (Shen et al., 2013 Transplantation 95, 663-670), they can also be treated with the combination regimen of rRspo1-Fc/rSlit2-Fc and/or CHIR-99021 and standard chemoradiotherapy in vivo.

Experiments with human crypts and ISCs have revealed that similar high levels of Wnt agonists are required for in vitro growth and maintenance of mouse and human intestinal organoids (Sato et al., 2009 Nature 459, 262-265; Ootani et al., 2009 Nat. Med. 15, 701-706; Spence et al., 2011 Nature 470, 105-109). However, growth of human intestinal organoids requires the inhibition of p38 MAP kinase and the inhibition of Tgfβ/Activin/Nodal signaling receptors (Sato et al., 2009 Nature 459, 262-265; Wang et al., 2013 Gastroenterology 145, 383-395; Gracz et al., 2013 Stem Cells 31, 2024-2030). Due to these potential differences between human and mouse ISCs, whether in analog to mouse Lgr5$^{high}$ ISCs (FIG. 31), Wnt agonists reduce p53 expression, inhibit p53-mediated apoptosis and protect human ISCs in response to IR will be tested. The results from these experiments will further verify the hypothesis as to whether Wnt/β-catenin agonists are beneficial to standard chemoradiation treatment of CRC carrying the concurrent loss-of-function mutations of APC and TP53.

Using DSS-treated Apc$^{MIN/+}$ mice, it was previously reported that the 3-day treatment with rRspo1/rSlit2 did not decrease the sensitivity of small intestinal adenomas to 5-FU (see FIG. 4C in Zhou et al., 2013 Nature 501, 107-111). In addition, this modality of rRspo1/rSlit2, in the absence of 5-FU, also potently inhibited large intestinal adenomas. Notably, the "just right" model of canonical Wnt predicts that there is an optimal window of Wnt signaling required for tumorigenesis and that very high Wnt signaling is actually cytotoxic and kills transformed cells (Albuquerque et al., 2002 Hum. Mol. Genet. 11, 1549-1560; Phesse 2013 Cancer Stem Cell Vol. 31(5) 512-514). This provocative hypothesis is apparently enforced by the finding that Rspo2-Lgr5 signaling suppresses colorectal cancer (Wu et al., 2014 Nat. Commun. 5, 3149). It is thus imperative to identify "the therapeutic window" for the degrees of Wnt/β-catenin activation and p53 inactivation that are optimal for chemoradioprotection of ISCs, but not ICSCs.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method for treating and/or preventing intestinal tissue damage resulting from exposure to an intestinal stem cell damaging event, comprising administering to a subject in need thereof a composition comprising a R-spondin 1 (Rspo1) agent and a Slit guidance ligand 2 (Slit2) agent, wherein said Rspo1 agent is a human Rspo1 protein, wherein said Slit2 agent is a human Slit2 protein,
   wherein said intestinal tissue comprises Roundabout 1 (Robo1) expression,
   wherein said Rspo1 agent is capable of binding the location on Robo1 where endogenous Rspo1 binds Robo1,
   wherein said Slit2 agent is capable of binding the location on Robo1 where endogenous Slit2 binds Robo1,
   wherein said administering of said composition comprising a Rspo1 agent and a Slit2 agent results in binding of said Rspo1 agent with Robo1 and binding of said Slit2 agent with Robo1 within said intestinal tissue,
   wherein said administering of said composition results in induction of intestinal stem cell homeogenesis and/or regeneration,
   wherein said subject is a human,
   wherein said intestinal stem cell damaging event is radiation therapy and/or chemotherapy, and
   wherein said composition comprising a Rspo1 agent and a Slit2 agent is administered prior to, concurrently with, and/or after exposure to the intestinal stem cell damaging event.

2. The method of claim 1, wherein said human has cancer and is undergoing radiation treatment.

3. The method of claim 1,
   wherein said binding of said Rspo1 agent with Robo1 and said binding of said Slit2 agent with Robo1 results in binding of Robo1 with lipoprotein receptor-related protein 6 (LRP6),
   wherein said binding of Robo1 with LRP6 occurs at the CC3 motif within Robo1, and
   wherein said binding of Robo1 with LRP6 results in phosphorylation of said LRP6.

4. The method of claim 3, wherein said binding of said Rspo1 agent with Robo1 and said binding of said Slit2 agent with Robo1 results in at least one of the following:
   association of Robo1 with leucine-rich repeat-containing G-protein coupled receptor 5 (LRG5),
   β-catenin translocation, and
   Wnt/β-catenin activation within said intestinal tissue, wherein said Wnt/β-catenin activation within said intestinal tissue transcriptionally represses p53 expression and inhibits p53-mediated intestinal stem cell (ISC) apoptosis.

5. The method of claim 1, wherein said intestinal tissue is small intestinal tissue.

6. The method of claim 1, wherein said intestinal tissue is the crypt region of a small intestine.

7. The method of claim 1, wherein said intestinal stem cell damaging event is an exposure to a medical procedure involving radiation.

8. The method of claim 7, wherein the medical procedure involving radiation is selected from the group consisting of photon radiotherapy, particle beam radiation therapy, brachytherapy, interstitial irradiation, intracavity irradiation, radioimmunotherapy, and ionizing (electromagnetic) radiotherapy.

9. A method for treating a human subject having a disorder, comprising administering to said subject a medical procedure involving radiation, and further administering during the course of said medical procedure a composition comprising a R-spondin 1 (Rspo1) agent and a Slit guidance ligand 2 (Slit2) agent, wherein said Rspo1 agent is a human Rspo1 protein, wherein said Slit2 agent is a human Slit2 protein,
   wherein said intestinal tissue comprises Roundabout 1 (Robo1) expression,
   wherein said Rspo1 agent is capable of binding the location on Robo1 where endogenous Rspo1 binds Robo1,
   wherein said Slit2 agent is capable of binding the location on Robo1 where endogenous Slit2 binds Robo1,
   wherein said administering of said composition comprising a Rspo1 agent and a Slit2 agent results in binding of said Rspo1 agent with Robo1 and binding of said Slit2 agent with Robo1 within said intestinal tissue,
   wherein said binding of said Rspo1 agent with Robo1 and said binding of said Slit2 agent with Robo1 results in binding of Robo1 with lipoprotein receptor-related protein 6 (LRP6), wherein said binding of Robo1 with LRP6 occurs at the CC3 motif within Robo1, wherein said binding of Robo1 with LRP6 results in phosphorylation of said LRP6,
   wherein said administration of said composition treats and/or prevents intestinal tissue damage resulting from said medical procedure,
   wherein said administering of said composition results in induction of intestinal stem cell homeogenesis and/or regeneration,
   wherein said disorder is cancer,
   wherein said medical procedure involving radiation is selected from the group consisting of photon radiotherapy, particle beam radiation therapy, brachytherapy, interstitial irradiation, intracavity irradiation, radioimmunotherapy, and ionizing (electromagnetic) radiotherapy, and wherein said composition comprising a Rspo1 agent and a Slit2 agent is administered prior to, concurrently with, and/or after administration of said medical procedure involving radiation.

10. The method of claim 9, wherein said binding of said Rspo1 agent with Robo1 and said binding of said Slit2 agent with Robo1 results in one or more of the following:
   association of Robo1 with leucine-rich repeat-containing G-protein coupled receptor 5 (LRG5),
   β-catenin translocation, and
   Wnt/β-catenin activation within said intestinal tissue, wherein said Wnt/β-catenin activation within said intestinal tissue transcriptionally represses p53 expression and inhibits p53-mediated intestinal stem cell (ISC) apoptosis.

11. The method of claim 9, wherein said intestinal tissue is small intestinal tissue.

12. The method of claim 9, wherein said intestinal tissue is the crypt region of a small intestine.

* * * * *